(12) United States Patent
Kent et al.

(10) Patent No.: US 7,674,881 B2
(45) Date of Patent: Mar. 9, 2010

(54) CONVERGENT SYNTHESIS OF PROTEINS BY KINETICALLY CONTROLLED LIGATION

(75) Inventors: Stephen Kent, Chicago, IL (US); Brad Pentelute, Chicago, IL (US); Duhee Bang, Boston, MA (US); Erik Johnson, Chicago, IL (US); Thomas Durek, Chicago, IL (US)

(73) Assignee: The University of Chicago, Chicago, IL (US)

( * ) Notice: Subject to any disclaimer, the term of this patent is extended or adjusted under 35 U.S.C. 154(b) by 109 days.

(21) Appl. No.: 11/545,923

(22) Filed: Oct. 10, 2006

(65) Prior Publication Data
US 2007/0082378 A1 Apr. 12, 2007

Related U.S. Application Data

(60) Provisional application No. 60/724,480, filed on Oct. 7, 2005.

(51) Int. Cl.
*C07K 1/06* (2006.01)
*C07K 1/107* (2006.01)

(52) U.S. Cl. ...................... 530/339; 530/345
(58) Field of Classification Search ........................ None
See application file for complete search history.

(56) References Cited

U.S. PATENT DOCUMENTS

| | | | | |
|---|---|---|---|---|
| 4,668,476 A | 5/1987 | Bridgham et al. | ............ | 422/62 |
| 4,816,513 A | 3/1989 | Bridgham et al. | ........ | 525/54.11 |
| 5,186,898 A | 2/1993 | Bridgham et al. | ........... | 422/102 |
| 5,854,389 A | 12/1998 | Kent et al. | ................... | 530/334 |
| 6,184,344 B1 | 2/2001 | Kent et al. | ................... | 530/323 |
| 6,307,018 B1 | 10/2001 | Kent et al. | ................... | 530/333 |
| 6,326,468 B1 | 12/2001 | Canne et al. | ................ | 530/333 |
| 6,476,190 B1 | 11/2002 | Kent et al. | ................... | 530/333 |
| 6,642,357 B1 | 11/2003 | Kent et al. | ................... | 530/332 |
| 2003/0149234 A1* | 8/2003 | Botti et al. | ................. | 530/300 |
| 2005/0113563 A1 | 5/2005 | Botti et al. | ................. | 530/350 |

FOREIGN PATENT DOCUMENTS

WO   WO 03/106615 A2 * 12/2003

OTHER PUBLICATIONS

International Search Report and Written Opinion, issued in International Application No. PCT/US2006/039455, dated Aug. 30, 2007.

Pentelute and Kent, "Selective Desulfurization of Cysteine in the Presence of Cys(Acm) in Polypeptides Obtained by Native Chemical Ligation," *Organic Letters*, 9:687-690, 2007.

(Continued)

*Primary Examiner*—Jeffrey E Russel
(74) *Attorney, Agent, or Firm*—Fulbright & Jaworski LLP

(57) ABSTRACT

The present invention concerns methods and compositions for synthesizing a polypeptide using kinetically controlled reactions involving fragments of the polypeptide for a fully convergent process. In more specific embodiments, a ligation involves reacting a first peptide having a protected cysteyl group at its N-terminal and a phenylthioester at its C-terminal with a second peptide having a cysteine residue at its N-termini and a thioester at its C-termini to form a ligation product. Subsequent reactions may involve deprotecting the cysteyl group of the resulting ligation product and/or converting the thioester into a thiophenylester.

25 Claims, 22 Drawing Sheets

OTHER PUBLICATIONS

Aguilar, "Chapter 1: HPLC of Peptides and Proteins, Basic Theory and Methodology," In: *Hplc of Peptides and Proteins: Methods and Protocols*, Methods in Molecular Biology, Humana Press, pp. 3-8, 2004.

Bang and Kent, "A One-Pot Total Synthesis of Crambin," *Angew. Chem., Int. Ed.*, 43:2534-2538, 2004.

Bang and Kent, "His6 tag-assisted chemical protein synthesis," *Proc. Natl. Acad. Sci. USA*, 102:5014-5019, 2005.

Bang et al., "Direct On-Resin Synthesis of Peptide-alphaThiphenylesters for Use in Native Chemical Ligation," *Organic Ltrs.*, 8(6):1049-1052, 2006.

Bang et al., "Total Chemical Synthesis and X-ray Crystal Structure of a Protein Diastereomer: [D-Gln35]Ubiquitin," *Agnew Chem. Int. Ed.*, 44:3852-3856, 2005.

Bang et al., "Total chemical synthesis of crambin," *J. Am. Chem. Soc.*, 126:1377-1383, 2004.

Bode et al., "Chemoselective Amide Ligations by Decarboxylative Condensations of N-Alkylhydroxylamines and alpha-Ketoacids," *Angew. Chem. Int. Ed.*, 45(8):1248-1252, 2006.

Bycroft et al., "A Novel Amino Protection-Deprotection Procedure and its Application in Solid Phase Peptide Synthesis," *J. Chem. Soc. Chem, Comm.*, 776-777, 1993.

Canne et al., "Chemical Protein Synthesis by Solid Phase Ligation of Unprotected Peptide Segments," *J. Am. Chem. Soc.*, 121:8720-8727, 1999.

Canne et al., "Extending the Applicability of Native Chemical Ligation," *J. Am. Chem. Soc.*, 118:5891-5896, 1996.

Canne et al., "Total Chemical Synthesis of a Unique Transcription Factor-Related Protein: cMyc-Max," *J. Am. Chem. Soc.*, 117:2998-3007, 1995.

Casi and Hilvert, "Convergent protein synthesis," *Curr. Opin. Struc. Biol.*, 13:589-594, 2003.

Cutler, "Protein arrays: the current state-of-the-art," *Proteomics*, 3(1):3-18, 2003.

Davis, "Synthesis of Gycoproteins," *Chem. Rev.*, 102:579-601, 2002.

Dawson and Kent, "Synthesis of native proteins by chemical ligation," *Annu. Rev. Biochem.*, 69:923-960, 2000.

Dawson et al., "Modulation of Reactivity in Native Chemical Ligation through the Use of Thiol Additives," *J. Am. Chem. Soc.*, 119:4325-4329, 1997.

Dawson et al., "Synthesis of Proteins by Native Chemical Ligation," *Science*, 266:776-779, 1994.

Evans Jr. et al., "The cyclization and polymerization of bacterially expressed proteins using modified self-splicing inteins," *J. Biol. Chem.*, 274:18359-18363, 1999.

Gaertner et al., "Synthesis of a thioester linker precursor for a general preparation of peptide C-terminal thioacids," *Tetrahedron Letts.*, 45:2239-2241, 2004.

Gentle et al., "Direct Production of Proteins with N-Terminal Cysteine for Site-Specific Conjugation," *Bioconjugate Chem.*, 15:658-663, 2004.

Green and Wuts, In: *Protective Groups in Organic Synthesis*, 2d Ed., 293-294, 318-319, 1991.

Hackeng et al., "Protein synthesis by native chemical ligation: expanded scope by using straightforward methodology," *Proc. Natl. Acad. Sci. USA*, 96:10068-10073, 1999.

Jelsch et al., "Accurate protein crystallography at ultra-high resolution: valence electron distribution in crambin," *Proc. Natl. Acad. Sci. USA*, 97:3171-3176, 2000.

Jencks, In: Catalysis in Chemistry and Enzymology (Dover Publications, Inc), pp. 537-542, 1987.

Johnson and Kent, "Insights into the Mechanism and Catalysis of the Native Chemical Ligation Reaction," *J. Am. Chem. Soc.*, 128:6640-6646, 2006.

Johnson et al., "Total Chemical Synthesis, Folding, and Assay of a Small Protein on a Water-Compatible Solid Support," *Angew. Chem. Int.. Ed.*, 45:3283-3287, 2006.

Kochendoerfer et al., "Design and Chemical Synthesis of a Homogeneous Polymer-Modified Erythropoiesis Protein," *Science*, 299:884-887, 2003.

Low et al., "Total synthesis of cytochrome b562 by native chemical ligation using a removable auxiliary," *Proc. Natl. Acad. Sci. USA*, 98:6554-6559, 2001.

Merrifield and Bach, "9-(2-Sulfo)fluorenylmethyloxycarbonyl Chloride, a New Reagent for the Purification of Synthetic Peptides," *J. Org. Chem.*, 43:4808-4816, 1978.

Miller and Scanlan, "Site-Selective N-Methylation of Peptides on Solid Support," *J. Am. Chem. Soc.*, 119:2301-2302, 1997.

Muir et al., "Protein synthesis by chemical ligation of unprotected peptides in aqueous solution," *Methods Enzymol.*, 289:266-298, 1997.

Muir, "Semisynthesis of proteins by expressed protein ligation," *Ann. Rev. Biochem.*, 72:249-289, 2003.

Nilsson et al., "Chemical Synthesis of Proteins," *Annu. Rev. Biophys. Biomol. Struc.*, 34:91-118, 2005.

Offer et al., "Extending Synthetic Access to Proteins with a Removable Acyl Transfer Auxiliary," *J. Am. Chem. Soc.*, 124:4642-4646, 2002.

Pratt and Bertozzi, "Synthetic glycopeptides and glycoproteins as tools for biology," *Chem. Soc. Rev.*, 34:58-68, 2005.

Royo et al., "S-2-(2,4-Dinitrophenyl)Ethyl-L-Cysteine: A New Derivative for Solid-Phase Peptide Synthesis," *Tetrahedron Lett.*, 33:2391-2394, 1992.

Samukov et al., "2-(4-Nitrophenyl)sulfonylethoxycarbonyl (Nsc) Group As a Base-Labile alpha-Amino Protection for Solid Phase Peptide Synthesis," *Tetrahedron Lett.*, 35:7821-7824, 1994.

Schnolzer and Kent, "Constructing Proteins by Dovetailing Unprotected Synthetic Peptides: Backbone-Engineered HIV Protease," *Science*, 256:221-225, 1992.

Schnolzer et al., "In situ neutralization in Boc-chemistry solid phase peptide synthesis," *Int. J. Peptide Protein Res.*, 40:.180-193, 1992.

Teeter et al., "Primary Structure of the Hydrophobic Plant Protein Crambin," *Biochemistry*, 20:5437-5443, 1981.

Villain, "Chemical Ligation of Multiple Peptide Fragments Using a New Protection Strategy," *Proc. Second Int. Seventeenth Am. Peptide Symp.*, 107-108, 2001.

Warren et al., "Toward Fully Synthrtic Glycoproteins by Ultimately Convergent Routes: A Solution to a Long-Standing Problem," *J. Am. Chem. Soc.*, 126:6576-6578, 2004.

Yan and Dawson, "Synthesis of Peptides and Proteins without Cysteine Residues by Native Chemical Ligation Combined with Desulfurization," *J. Am. Chem. Soc.*, 123:526-533, 2001.

Zhang and Tam, "Synthesis and Application of Unprotected Cyclic Peptides as Building Blocks for Peptide Dendrimers," *J. Am. Chem. Soc.*, 119:2363-2370, 1997.

\* cited by examiner

SEQUENCE LISTING

```
<160> NUMBER OF SEQ ID NOS: 41

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:   Synthetic
      Peptide

<400> SEQUENCE: 1

Tyr Lys Met Asp Phe His Ile Ala Ala
 1               5

<210> SEQ ID NO 2
<211> LENGTH: 9
<212> TYPE: PRT
<213> ORGANISM: Artificial Sequence
<220> FEATURE:
```

```
<223> OTHER INFORMATION: Description of Artificial Sequence:  Synthetic
      Peptide

<400> SEQUENCE: 2

Tyr Lys Met Asp Phe His Ile Ala Ala
  1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 3

Cys Asn Val Arg Ser Gly Thr Glu Pro Trp Gln Leu
  1               5                  10

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 4

Cys Pro Ser Ile Val Ala Arg Ser Asn Phe Asn Ala Cys Arg Leu Pro
  1               5                  10                  15

Gly Thr Pro Glu Ala Leu
            20

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 5

Asp Lys Leu Leu Met
  1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 6

Leu Tyr Arg Ala Leu
  1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 7

Cys Leu Tyr Leu Ala Ala
```

-continued

```
                1               5

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 8

Cys Pro Ser Ile Val Ala Arg Ser Asn Phe Asn Ala
  1               5                  10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 9

Cys Arg Leu Pro Gly Thr Pro Glu Ala Leu
  1               5                  10

<210> SEQ ID NO 10
<211> LENGTH: 32
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 10

Cys Pro Ser Ile Val Ala Arg Ser Asn Phe Asn Ala Cys Arg Leu Pro
  1               5                  10                  15

Gly Thr Pro Glu Ala Leu Cys Arg Leu Pro Gly Thr Pro Glu Ala Leu
             20                  25                  30

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 11

Cys Pro Ser Ile Val Ala Arg Ser Asn Phe Asn Ala
  1               5                  10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 12

Cys Arg Leu Pro Gly Thr Pro Glu Ala Leu
  1               5                  10

<210> SEQ ID NO 13
<211> LENGTH: 10
<212> TYPE: PRT
```

```
<213> ORGANISM: Artificial Sequence
<220> FEATURE:
<223> OTHER INFORMATION: Description of Artificial Sequence:  Synthetic
      Peptide

<400> SEQUENCE: 13

Leu Tyr Arg Ala Cys Phe Gly Cys Lys Ile
 1               5                  10

<210> SEQ ID NO 14
<211> LENGTH: 37
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 14

Lys Cys Asn Thr Ala Thr Cys Ala Thr Gln Arg Leu Cys Asn Phe Leu
 1               5                  10                  15

Val His Ser Ser Asn Asn Phe Gly Pro Ile Leu Pro Pro Thr Asn Val
             20                  25                  30

Gly Ser Asn Thr Tyr
             35

<210> SEQ ID NO 15
<211> LENGTH: 37
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 15

Lys Cys Asn Thr Ala Thr Cys Ala Thr Gln Arg Leu Ala Asn Phe Leu
 1               5                  10                  15

Val His Ser Ser Asn Asn Phe Gly Pro Ile Leu Pro Pro Thr Asn Val
             20                  25                  30

Gly Ser Asn Thr Tyr
             35

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 16

Lys Cys Asn Thr Ala Thr Cys Ala Thr Gln Arg Leu
 1               5                  10

<210> SEQ ID NO 17
<211> LENGTH: 25
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 17

Cys Asn Phe Leu Val His Ser Ser Asn Asn Phe Gly Pro Ile Leu Pro
 1               5                  10                  15

Pro Thr Asn Val Gly Ser Asn Thr Tyr
```

<210> SEQ ID NO 18
<211> LENGTH: 28
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: misc_feature
<222> LOCATION: (7)..(7)
<223> OTHER INFORMATION: Xaa = Nle

<400> SEQUENCE: 18

Gly Cys Pro Ala Ile Leu Xaa Arg Cys Lys Gln Asp Ser Asp Cys Leu
 1               5                  10                  15

Ala Gly Cys Val Cys Gly Pro Asn Gly Phe Cys Gly
            20                  25

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: misc_feature
<222> LOCATION: (7)..(7)
<223> OTHER INFORMATION: Xaa = Nle

<400> SEQUENCE: 19

Gly Cys Pro Arg Ile Leu Xaa Arg Cys Lys Gln Asp Ser Asp Cys Leu
 1               5                  10                  15

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 20

Cys Gly Cys Val Cys Gly Pro Asn Gly Phe Cys Gly
 1               5                  10

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 21

Leu Ala Cys Ala Pro Met Leu Phe
 1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 22

-continued

```
Leu Ala Ala Ala Pro Met Leu Phe
 1               5

<210> SEQ ID NO 23
<211> LENGTH: 30
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 23

Gly Cys Pro Arg Ile Leu Met Arg Cys Lys Gln Asp Ser Asp Cys Leu
 1               5                  10                  15

Ala Gly Cys Val Cys Gly Pro Asn Gly Phe Cys Gly Ser Pro
            20                  25                  30

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 24

Gly Cys Pro Arg Ile Leu Met Arg Cys Lys Gln Asp Ser Asp Cys Leu
 1               5                  10                  15

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 25

Leu Leu Leu Pro
 1

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 26

Lys Thr Tyr Gln Cys Gln Tyr Cys Glu Tyr Arg Ser
 1               5                  10

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 27

Cys Ala Thr Tyr Thr Gly
 1               5

<210> SEQ ID NO 28
```

<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 28

Cys Ile Ile Ile Pro Gly Ala Thr
  1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 29

Cys Pro Gly Asp Tyr Ala Asn
  1               5

<210> SEQ ID NO 30
<211> LENGTH: 46
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 30

Thr Thr Cys Cys Pro Ser Ile Val Ala Arg Ser Asn Phe Asn Ala Cys
  1               5                  10                  15

Arg Leu Pro Gly Thr Pro Glu Ala Leu Cys Ala Thr Tyr Thr Gly Cys
             20                  25                  30

Ile Ile Ile Pro Gly Ala Thr Cys Pro Gly Asp Tyr Ala Asn
         35                  40                  45

<210> SEQ ID NO 31
<211> LENGTH: 25
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 31

Thr Thr Cys Cys Pro Ser Ile Val Ala Arg Ser Asn Phe Asn Ala Cys
  1               5                  10                  15

Arg Leu Pro Gly Thr Pro Glu Ala Leu
             20                  25

<210> SEQ ID NO 32
<211> LENGTH: 21
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 32

Cys Ala Thr Tyr Thr Gly Cys Ile Ile Ile Pro Gly Ala Thr Cys Phe
  1               5                  10                  15

Gly Asp Tyr Ala Asn
             20

```
<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 33

Cys Gly Cys Val Cys Gly Pro Asn Gly Phe Cys Gly Ser Asp
  1               5                  10

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 34

Arg Arg Arg Arg

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 35

Arg Arg Arg Arg Arg
  1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 36

Arg Arg Arg Arg Arg Arg
  1               5

<210> SEQ ID NO 37
<211> LENGTH: 28
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: misc_feature
<222> LOCATION: (7)..(7)
<223> OTHER INFORMATION: Xaa = Nle

<400> SEQUENCE: 37

Gly Cys Pro Arg Ile Leu Xaa Arg Cys Lys Gln Asp Ser Asp Cys Leu
  1               5                  10                  15

Cys Gly Cys Val Cys Gly Pro Asn Gly Phe Cys Gly
                 20                  25

<210> SEQ ID NO 38
```

-continued

```
<211> LENGTH: 12
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 38

Lys Cys Asn Thr Ala Thr Cys Ala Thr Gln Arg Leu
  1               5                  10

<210> SEQ ID NO 39
<211> LENGTH: 25
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 39

Cys Asn Phe Leu Val His Ser Ser Asn Asn Phe Gly Pro Ile Leu Pro
  1               5                  10                  15

Pro Thr Asn Val Gly Ser Asn Thr Tyr
             20                  25

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 40

Leu Tyr Arg Ala Cys Phe Gly Ala Lys Ile
  1               5                  10

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 41

Cys Ala Thr Tyr Thr Gly Cys Ile Ile Pro Gly Ala Thr
  1               5                  10
```

CONVERGENT SYNTHESIS OF PROTEINS BY KINETICALLY CONTROLLED LIGATION

This application claims the benefit of U.S. Provisional Application Ser. No. 60/724,480 filed Oct. 7, 2005, the entire disclosure of which is specifically incorporated herein by reference.

This invention was made with government support under grant number DE-FG02-04ER63786 awarded by the Department of Energy and grant number DMR-0213745 awarded by the National Science Foundation MRSEC. The government has certain rights in the invention.

BACKGROUND OF THE INVENTION

1. Field of the Invention

The invention relates generally to chemistry and protein science. More specifically, it concerns methods and compositions for synthesizing polypeptides and proteins, and more particularly, a convergent, kinetically-controlled method and intermediates for covalently assembling multiple peptide fragments into a full length polypeptide.

2. Description of Related Art

In the past decade total chemical synthesis has proved to be a robust and reproducible method for using amino acid sequence data predicted from genome sequencing to make high purity polypeptide chains that fold with great efficiency to give proteins of defined tertiary structure and full biological activity (Dawson and Kent, 2000; Kochendoerfer et al., 2003; Bang and Kent, 2004). This success has been made possible by the introduction of 'chemical ligation' methods, based on the chemoselective reaction of unprotected peptides under mild conditions in aqueous solution. Chemical synthesis gives precise atom-by-atom control over the structure of the protein molecule. Chemistry has been used to make analogue protein molecules containing multiple non-coded amino acids, fixed elements of secondary structure, backbone-modified polypeptide chains, or non-linear peptide chain topologies (Dawson and Kent, 2000). By correlating defined changes in the chemical structure of the protein molecule with the effects on folding and function, the inventors can gain new insights into the principles governing the biological activities of proteins.

Recent improvements in synthetic methods have been focused on the preparation of proteins by sequential ligation of three or four peptide segments (Bang and Kent, 2004; Canne et al., 1999; Bang and Kent, 2005, which are incorporated by reference). See also U.S. Pat. No. 6,184,344 (in solution); Canne et al. (1999) and U.S. Pat. No. 6,326,468 (in solid phase); and U.S. Pat. Publication 2005/0113563, all of which are hereby incorporated by reference.

Although syntheses of large proteins have been reported, these are regarded as exceptional 'tours de force' (Casi and Hilvert, 2003); in general, synthesis of larger molecules is laborious, time-consuming, and gives low yields, and for these reasons is not widely practiced. Ultimately, there is a need to extend routine total chemical synthesis to proteins more typical of the average size found in nature (approximately 35 kilodaltons, approximately 300 amino acids). The present invention addresses this need.

SUMMARY OF THE INVENTION

The present invention is based on the concept of synthesizing a polypeptide using a fully convergent approach. Such an approach refers to a process in which the a polypeptide is constructed by joining fragments of the polypeptide, which can be done in any order. While one or more fragments can be sequentially added, the approach is not limited in this way as prior methods have been. Moreover, the approach is also not limited by the number of different fragments that can ultimately be joined. Therefore, the present invention provides methods, compositions, and other apparatuses for implementing polypeptide synthesis, which may also be fully convergent.

In some embodiments of the invention, there are methods for synthesizing polypeptide comprising reacting a first C-activated peptide, having a N-terminal-protected cysteyl residue, with a first N-activated peptide, having a N-terminal cysteyl residue, to form a first ligation product containing an amide bond between the α-carbon of the C-terminal of the first C-activated peptide and the α-carbon of the N-terminal of the first N-activated peptide; both peptides having leaving groups on both terminal residues, with the first C-activated peptide having a better leaving group on the residue at the C terminal end than the residue at the C-terminal end of the first N-activated peptide.

A "C-activated peptide" refers to a peptide that has a more reactive residue at its C-terminus, by virtue of a leaving group on the residue, than the C-terminal residue of other peptides present in the reaction mixture. An "N-activated peptide" refers to a peptide that has a more reactive residue at its N-terminus, by virtue of the functional group on the residue, than the N-terminal residue of other peptides present in the reaction mixture. The terms "N-terminus" (noun) and "N-terminal" (adjective) are used according to their ordinary and plain meanings to refer to the residue at the amino-terminus of a peptide or polypeptide. Similarly, terms "C-terminus" (noun) and "C-terminal" (adjective) are used according to their ordinary and plain meaning to refer to the residue at the carboxy terminus of a peptide or polypeptide.

The term "N-terminal cysteyl residue" refers to a cysteyl residue at the amino-terminus of a peptide or polypeptide. In certain embodiments, the cysteyl residue is in a reduced state. A reaction between two peptides that results in the formation of a ligation product refers to a chemical reaction that forms a peptide bond between two peptides to form a single, longer peptide or polypeptide.

The invention contemplates that the N-terminus and/or C-terminus may be modified with respect to a native polypeptide, or it may be unmodified. Generally, the modification include, but are not limited to, activating, deactivating, protecting, or deprotecting one or both terminal ends. The invention also contemplates modifications that make the terminus more or less reactive.

In the different embodiments of the invention, the term "better leaving group" refers to a chemical group that in the context of the synthesis possesses the ability to be substituted more readily than the group to which it is being compared. In the context of the present invention, the ability of a leaving group to be substituted more readily is relative to another leaving group on the same terminus of a different peptide or polypeptide. In other words, a better C-terminal leaving group means better with respect to the C-terminus leaving group of another peptide or polypeptide. This is likewise true for a better N-terminal functional group. Moreover, it is contemplated that the ability to act as a leaving group can be assessed using a number of different assays, such as comparable ligation reaction conditions and assessments employed with respect to FIG. 7.

In certain embodiments of the invention, a C-activated peptide has a leaving group at its C-terminus. In particular embodiments, the structure of the leaving group is —S—Ar, wherein "Ar" represents an alkyl, aralkyl, aryl, or heterocyclic group. In other embodiments, the leaving group is —SCH$_2$CH$_2$SO$_3$Na.

In the context of the present invention, the C-activated peptide has an N-terminal protected cysteyl residue, which means that the cysteyl residue is less reactive than it would otherwise be under the reaction conditions. In certain cases, the N-terminal protected cysteyl residue is a cysteyl residue with a linking group connecting its thiol group to its amino group.

An N-activated peptide in some embodiments of the invention has a leaving group with the structure —S—R, wherein "R" represents a hydrogen atom, an alkyl, an aralkyl, or an aliphatic heterocyclic group. In particular embodiments, R is —CH$_2$CH$_2$CONHCH(CH$_2$CH(CH$_3$)$_2$)COOH. In others, R is a hydrogen atom.

The present invention also concerns methods for synthesizing a polypeptide comprising: a) reacting a first N—C$^a$ peptide with a first N$^a$—C peptide to form a first N—C ligation product, wherein: N and N$^a$ represent N-terminal groups, C and C$^a$ represent C-terminal groups, C$^a$ is more reactive than C, and N$^a$ is more reactive than N. In the context of terminal groups, the term "more reactive" means that the described group is more likely to undergo a chemical change, the result being the formation of a ligation product, such as is described in the Examples section, for instance the reaction concerning FIG. 7. For example, C$^a$ is more reactive than C with respect to a chemical reaction with an N-terminal group of another peptide. In further embodiments, the method includes one or more of the following: b) reacting a second N—C$^a$ peptide with a second N$^a$—C peptide to form a second N—C ligation product, c) converting the first N—C ligation product into a first N—C$^a$ ligation product, d) converting the second N—C ligation product into a first N$^a$—C ligation product, and e) reacting the first N—C$^a$ ligation product with the first N$^a$—C ligation product to form a third N—C ligation product. The term "converting" is used to indicate a chemical change in a composition to alter its reactivity. The superscript "a" notation indicates that the end of a molecule is activated in terms of reactive ability as compared to the end of another molecule lacking the notation.

In certain embodiments of the invention, a first modified peptide is reacted with a second modified peptide to form a first ligation product containing an amide bond between the α-carbon of the C-terminal of the first modified peptide and the α-carbon of the N-terminal of the second modified peptide. The first modified peptide having the following formula:

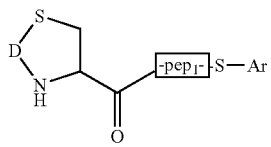

wherein "D" represents an alkyl, aryl, aralkyl, or heterocyclic group and "Ar" represents an alkyl, aryl, aralkyl, or heterocyclic group. The second modified peptide has the following formula:

wherein "R" represents a hydrogen atom, an alkyl, an aralkyl, or heterocyclic group. In this method, the chemical structure Ar and R are different, so as to provide a first ligation product having the following formula:

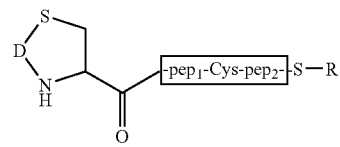

The term "pep" represents an unbranched chain of amino acid residues linked by peptide bonds. The term "modified peptide" refers to a peptide that has a chemical structure that differs from a native peptide having the same amino acid sequence, such as by having a different chemical group at one or both ends of the peptide.

In certain embodiments of the invention, R is an alkyl group. In still further embodiments, R is a hydrogen atom, while in others R is —CH$_2$CH$_2$CONHCH(CH$_2$CH(CH$_3$)$_2$)COOH. Moreover, in specific embodiments Ar is an aryl group. It is contemplated that Ar can be a substituted or unsubstituted: phenyl, pyridyl, or pyrimidyl group. In particular embodiments, the phenyl group is unsubstituted. Alternatively, the phenyl group can have one or more substituents. The substituents include but are not limited to a carboxylic acid, chloro, nitro, methyl, hydroxyl, acetic acid, methoxy, or amino. In certain cases, Ar is —CH$_2$CH$_2$SO$_3$Na, while in others Ar is a benzyl group. Furthermore, in particular cases D is a methylene group. Consequently, the present invention specifically contemplates a method involving peptides in which R is —CH$_2$CH$_2$CONHCH(CH$_2$CH(CH$_3$)$_2$)COOH, Ar is a phenyl group, and D is a methylene group.

In addition, in some embodiments the amino acid sequence represented by the term "pep" does not contain any protected amino acid residues. Further embodiments discussed with respect to upstream and downstream peptides can be implemented in the context of this method.

In certain embodiments, the present invention involves two peptides in a reaction to form a ligation product. Methods of the invention may involve, involve at least, or involve at most a first, second, third, fourth, fifth, sixth, seventh, eighth, ninth, tenth, eleventh, twelfth, thirteenth, fourteenth, fifteenth, sixteenth, seventeenth, eighteenth nineteenth, twentieth, twenty-first, twenty-second, twenty-third, twenty-fourth, twenty-fifth or more (or any range derivable therein) ligation product.

The peptide that will end up upstream or on the N-terminal portion of the ligation product with respect to the other peptide can be generally referred to as the "upstream peptide." In certain embodiments, this peptide may also be referred to more specifically as a C-activated peptide, an N—C$^a$ peptide, or a modified peptide in which the α-carbon on its C-terminal is involved in the ligation reaction. Methods of the invention may involve, involve at least, or involve at most a first, second, third, fourth, fifth, sixth, seventh, eighth, ninth, tenth, eleventh, twelfth, thirteenth, fourteenth, fifteenth, sixteenth, seventeenth, eighteenth nineteenth, twentieth, twenty-first, twenty-second, twenty-third, twenty-fourth, twenty-fifth or more (or any range derivable therein) C-activated peptide, N—C$^a$ peptide, or modified peptide, including an upstream modified peptide.

Similarly, the peptide that will end up downstream or on the C-terminal portion of the ligation product with respect to the other peptide can be generally referred to as the "downstream peptide." In certain embodiments, this peptide may also be referred to more specifically as an N-activated peptide, an $N^\alpha$—C peptide, or a modified peptide in which the α-carbon on its N-terminal is involved in the ligation reaction. Methods of the invention may involve, involve at least, or involve at most a first, second, third, fourth, fifth, sixth, seventh, eighth, ninth, tenth, eleventh, twelfth, thirteenth, fourteenth, fifteenth, sixteenth, seventeenth, eighteenth nineteenth, twentieth, twenty-first, twenty-second, twenty-third, twenty-fourth, twenty-fifth or more (or any range derivable therein) N-activated peptide, $N^\alpha$—C peptide, or modified peptide, including a downstream modified peptide.

In embodiments of the invention, reactions are kinetically controlled, which means that of the various possible reactions that may occur, the fastest reaction leading to a stable product will predominate. This provides better yields to make convergent synthesis practical and efficient. It is contemplated that in embodiments of the invention, the yield from a ligation reaction is about, at least about, or at most about 40, 45, 50, 55, 60, 65, 70, 75, 80, 85, 90, 95 or more percent (or any range derivable therein) with respect to the reaction components. In certain embodiments, the yield is at least about 45%.

In some aspects of the invention, the upstream peptide has at its C-terminal end a chemical group that can react with a chemical group at the N-terminal end of a downstream peptide. In certain embodiments, the chemical group of the upstream peptide has the chemical structure —S—Ar, wherein "Ar" represents an alkyl, aralkyl, aryl, or heterocyclic group. The Ar may be a substituted or unsubstituted phenyl, substituted or unsubstituted pyridyl, or substituted or unsubstituted pyrimidyl group. When the Ar is substituted, it can have one or more substituents. Depending on the group, the Ar can be substituted with, with at least, or with at most 1, 2, 3, 4, 5, 6, 7, 8, 9, 10 or more substituents, or any range derivable therein. In certain embodiments, a substituent is selected from the group consisting of a carboxylic acid, chloro, nitro, methyl, hydroxyl, acetic acid, methoxy, and amino. In some embodiments, the Ar is benzyl. In others the chemical group at the C-terminal end of the upstream peptide has the formula —S—Ph, where "Ph" refers to an unsubstituted phenyl group.

In other embodiments, the chemical group of the upstream peptide has the chemical structure —$SCH_2CH_2SO_3Na$. It is contemplated that the sodium ion may be replaced by a proton, a potassium ion, or other monovalent cation.

Moreover, it is contemplated that the conjugate acid of the leaving group or chemical group at the C-terminal end of an upstream peptide has a pKa of about, at least about, or at most about 4, 5, 6, 7, 8, 9, or any range derivable therein. In some embodiments, the pKa is from about 4 to about 9 or from about 6 to about 8. The conjugate acid of the leaving group is a thiol or a mercaptan in some cases.

The present invention also concerns an upstream peptide having an N-terminal protected cysteyl residue. In some embodiments, the cysteyl residue has a linking group connecting its thiol group to its amino group. Moreover, the linking group is an alkyl or aralkyl group in further embodiments, while it is a methylene in others.

In some aspects of the invention, the downstream peptide has at its N-terminal end a chemical group that can react with a chemical group at the C-terminal end of a upstream peptide. In certain embodiments, the chemical group of the downstream peptide has the chemical structure —S—R, wherein "R" represents a hydrogen atom, an alkyl, an aralkyl, or an aliphatic heterocyclic group. In some embodiments, R has the specific chemical structure —$CH_2CH_2CONHCH(CH_2CH(CH_3)_2)COOH$, or a salt thereof. In certain other embodiments, R is a hydrogen atom.

A reaction to form a ligation product between two peptides is referred to as a "ligation reaction." In certain other embodiments an upstream peptide and/or a downstream peptide is a prior ligation product. This means that the peptide itself is the product of a previous reaction between a prior upstream peptide and a prior downstream peptide. In this situation, the resulting ligation product is then chemically modified (converted) to be more reactive in a ligation reaction. The ligation product can be converted or chemically modified into a more reactive compound to act as an upstream peptide or as a downstream peptide, depending on the change to it. Moreover, this means in some embodiments, the upstream peptide or downstream peptide is a prior C-activated peptide or a prior N-activated peptide.

In further embodiments of the invention, methods include a step of deprotecting a chemical group at the N-terminal residue of peptide. In many embodiments, the peptide is also a ligation product. The term "deprotecting" refers to a chemical modification of the residue at the N-terminal end of the peptide to render one or more chemical groups on the residue more reactive than it was prior to the deprotection. This is done in some embodiments of the invention so the protected peptide can subsequently be used as a downstream peptide in a ligation reaction. The peptide may or may not be a prior ligation product. Another term frequently used in the art for this process is "unmasking."

The deprotection can result in the creation of a downstream peptide that has a more reactive chemical group at its N-terminus than before the deprotection. In certain embodiments, this deprotection step of a ligation product results in the formation of downstream peptide having a N-terminal cysteyl residue. Methods for deprotecting may involve incubating the protected peptide with methoxyamine-hydrochloride. In certain embodiments, the deprotection occurs in a reaction mixture having a pH of about, at least about, or at most about 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0 in aqueous buffer, or any range derivable therein, such as from about 3 to about 5. It is contemplated that any peptide with a protected chemical group may be deprotected. In certain embodiments, the peptide has a residue at its N-terminal end that is protected. It is contemplated that any peptide that was used in a ligation reaction as a peptide with a protected terminus or that will be used in a ligation reaction as a downstream peptide may be deprotected. A peptide that is deprotected may also be the result of multiple ligation reactions. In other words, in the context of the present invention the peptide may be what is referred to as a first, second, third, fourth, fifth, sixth, seventh, eighth, ninth, tenth or more peptide, modified peptide, N-activated peptide, or ligation product.

Methods of the invention may also include a step in which a chemical group on the residue at the C-terminal end of a peptide is replaced or modified. In embodiments of the invention, the chemical group is modified into or replaced by a chemical group that renders the peptide more reactive as an upstream peptide in a ligation reaction with a downstream peptide (referred to a "C-terminal activation step"). It is contemplated that any peptide that was used in a ligation reaction as a peptide with a relatively non-reactive (non-reactive with respect to the upstream peptide in a ligation reaction) chemical group on the C-termini residue or that will be used in a ligation reaction as the upstream peptide may undergo a reaction to render the chemical group more reactive.

In certain embodiments, the chemical group attached to the carbonyl group of the C-terminal residue has the structure —SH. The replacement of this chemical group with a better leaving group involves, in some embodiments, alkylating the peptide or ligation product with an electrophile. In some cases, the electrophile is an α-halocarbonyl. In others, it may be methyl-triflate. The α-halocarbonyl can be iodoacetic acid. Furthermore, in some embodiments, the peptide or ligation product is alkylated with an electrophile in a pH of about, at least about, or at most about 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, and 5.0, or any range derivable therein, in an aqueous buffer. In specific embodiments, the pH is between about 2 and about 5 in aqueous buffer.

A peptide that is modified for use as an upstream peptide in a ligation reaction may also be the result of multiple ligation reactions itself. In other words, in the context of the present invention, the peptide may be what is referred to as a first, second, third, fourth, fifth, sixth, seventh, eighth, ninth, tenth or more peptide, modified peptide, C-activated peptide, or ligation product. In some embodiments, the C-terminal leaving group of a peptide is replaced with a better leaving group to form a C-activated ligation product.

It is contemplated that embodiments of the invention include iterations of steps to synthesize a polypeptide from fragments of the polypeptide. This means that to achieve kinetically controlled reactions, a ligation product (or a peptide) may be modified or converted as discussed above, depending upon whether it will be in a subsequent ligation reaction as a downstream or upstream peptide. Subsequently, the modified or converted peptide can be reacted with another peptide (or ligation product) in a ligation reaction to form another ligation product. It is contemplated that the synthesis can involve, involve at least, or involve at most 1, 2, 3, 4, 5, 6, 7, 8, 9, 10, 11, 12, 13, 14, 15, 16, 17, 18, 19, 20 or more (or any range derivable therein) ligation reactions, deprotection reactions, and/or C-terminal activations. A synthesis may also involve, involve at least, or involve at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 32, 33, 34, 35, 36, 37, 38, 39, 40 or more (or any range derivable therein) different peptides and/or ligation products, which differ by amino acid sequence.

Using the reactions described herein, it is contemplated that the synthesis can occur through any ordering of different ligation reactions. For example, the synthesis may be fully convergent, as illustrated by example in FIG. 1. Moreover, it is contemplated that the synthesis is not required to be only sequential at any point (except for the last ligation); this means that the polypeptide synthesis does not require that addition of a peptide to a ligation product be in one direction only.

Moreover, in embodiments of the invention, there is no requirement for the use of any cleavable linkers to monitor reactions, as discussed in U.S. Pat. No. 6,326,468, which is hereby incorporated by reference, though such linkers can be used.

Any synthesis method will involve some form of sequential synthesis in which adjacent peptides are ligated to one another. The extent to which a synthesis is sequential may differ, however. For example, the synthesis of a polypeptide X with the following general sequence and chemical structure

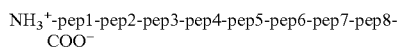

may occur by any number of ways in terms of the order of reactions. In one example, a fully convergent synthesis could occur by first having the following ligation reactions: (1) pep1 and pep2 (to form pep1-pep2); (2) pep3 and pep4 (to form pep3-pep4); (3) pep5 and pep6 (to form pep5-pep6); and (4) pep7 and pep8 (to form pep7-pep8). Then the following ligation reactions may follow: (5) the ligation product of (1) with the ligation product of (2) to form pep1-pep2-pep3-pep4 and (6) the ligation product of (3) with the ligation product of (4) to form pep5-pep6-pep7-pep8. Finally, the ligation product of (5) may be reacted with the ligation product of (6) to form the desired polypeptide X.

Another example of different reactions of a synthesis method is provided. In each of the methods, the invention contemplates that any modified peptide can be the product of one or more ligation reactions between other modified peptides. The reactions are intended to be exemplary. Any one method need not include all of these different reactions or peptides. The numbering of peptides and products is intended to distinguish different entities and does not mean, for example, that a synthesis having a reaction described with a "fourteenth modified product", as discussed below, actually has fourteen modified products.

In methods of the invention, a first modified peptide is reacted with a second modified peptide to form a first ligation product containing an amide bond between the α-carbon of the C-terminal of the first modified peptide and the α-carbon of the N-terminal of the second modified peptide. The first modified peptide having the following formula:

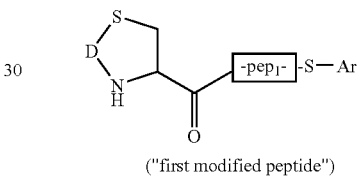

("first modified peptide")

wherein "D" represents an alkyl, aryl, aralkyl, or heterocyclic group and "Ar" represents an alkyl, aryl, aralkyl, or heterocyclic group. The second modified peptide has the following formula:

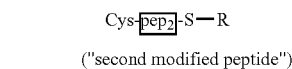

("second modified peptide")

wherein "R" represents a hydrogen atom, an alkyl, an aralkyl, or heterocyclic group. In this method, the chemical structure Ar and R are different, so as to provide a first ligation product having the following formula:

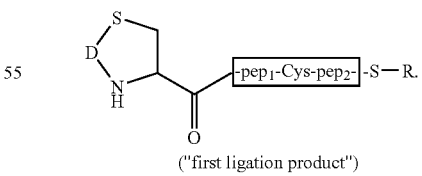

("first ligation product")

This first ligation product, or any other ligation product, may be converted into a modified product for use as a downstream modified peptide or an upstream modified peptide, depending on the type and location of the chemical group being modified. For example, if the ligation product is modified so that it has a better leaving group on the amino acid residue at its carboxy end, this ligation product can be employed as an upstream modified peptide. Alternatively, if a protected chemical group at the amino terminal end of the peptide is modified to unmask that residue, the modified ligation product can be used as a downstream peptide.

Therefore, in additional embodiments, this method has a step of converting the first ligation product into a first modified product that is a downstream modified product having the following formula:

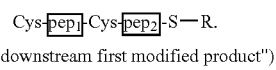

("downstream first modified product")

The term "downstream modified product" refers to a modified product that can be employed subsequently as a downstream peptide in a ligation reaction. This modified peptide can then be used in any ligation with any upstream modified peptide or ligation product.

This first modified product may then be reacted with a third modified peptide to form a second ligation product containing an amide bond between the α-carbon of the C-terminal of the third modified peptide and the α-carbon of the N-terminal of the first modified product. The third modified peptide may have the following formula:

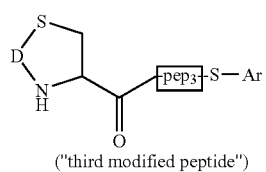

("third modified peptide")

and the second ligation product will have the following formula:

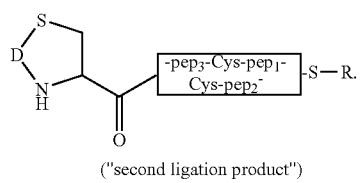

("second ligation product")

The second ligation product can be converted into a downstream peptide as a second modified product having the following formula:

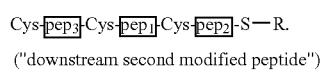

("downstream second modified peptide")

This modified peptide can then be used in any ligation with any upstream modified peptide or ligation product. For example, this second modified product can then be reacted with a fourth modified peptide to form a third ligation product containing an amide bond between the α-carbon of the C-terminal of the fourth modified peptide and the α-carbon of the N-terminal of the second modified product. The fourth modified peptide may have the following formula:

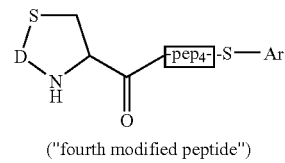

("fourth modified peptide")

and the third ligation product will have the following formula:

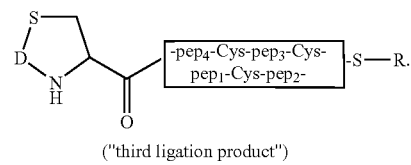

("third ligation product")

It is possible for the method to have an additional step of converting the third ligation product into a third modified product for use as a downstream peptide having the following formula:

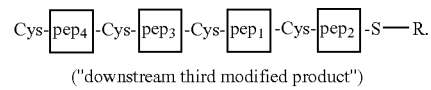

("downstream third modified product")

This modified peptide can then be used in any ligation with any upstream modified peptide or ligation product.

Alternatively, instead of converting the first ligation product into a downstream first modified product, it could be converted into a third modified product that is an upstream modified product having the following formula:

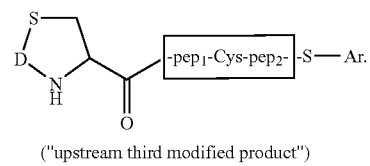

("upstream third modified product")

The term "upstream modified product" refers to a modified product that can be employed subsequently as an upstream peptide in a ligation reaction. This modified peptide can then be used in any ligation with any downstream modified peptide or ligation product.

The upstream third modified product can be reacted with a fifth modified peptide to form a fourth ligation product containing an amide bond between the α-carbon of the C-terminal of the upstream third modified product and the α-carbon of the N-terminal of the fifth modified peptide. The fifth modified peptide may have the following formula:

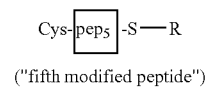

("fifth modified peptide")

and the fourth ligation product will then have the following formula:

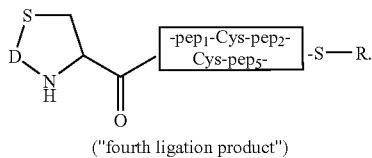

("fourth ligation product")

The fourth ligation product can be converted into a fourth modified product that is an upstream modified product with the following formula:

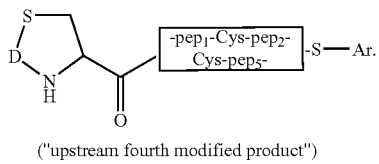

("upstream fourth modified product")

This modified peptide can then be used in any ligation with any downstream modified peptide or ligation product. For example, the upstream fourth modified product can be reacted with a sixth modified peptide to form a fifth ligation product containing an amide bond between the α-carbon of the C-terminal of the fourth modified product and the α-carbon of the N-terminal of the sixth modified peptide; the sixth modified peptide having the following formula:

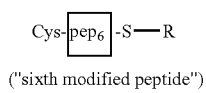

("sixth modified peptide")

and the fifth ligation product having the following formula:

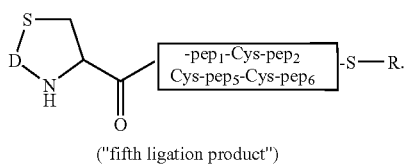

("fifth ligation product")

The method may involve converting the fifth ligation product to form an upstream fifth modified product having the following formula:

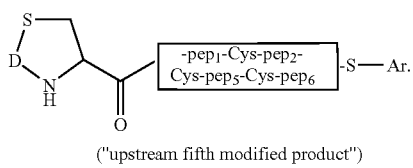

("upstream fifth modified product")

This modified peptide can then be used in any ligation with any downstream modified peptide or ligation product.

In other embodiments, a seventh modified peptide can be reacted with an eighth modified peptide to form a sixth ligation product containing an amide bond between the α-carbon of the C-terminal of the seventh modified peptide and the α-carbon of the N-terminal of the eighth modified peptide, where the seventh modified peptide has the following formula:

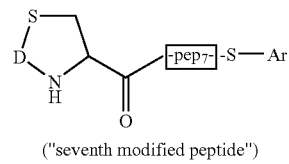

("seventh modified peptide")

and the eighth modified peptide has the following formula:

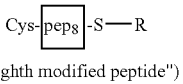

("eighth modified peptide")

to produce the sixth ligation product having the following formula:

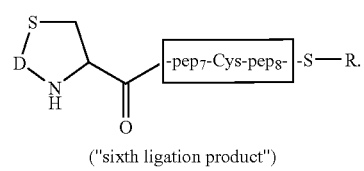

("sixth ligation product")

In additional embodiments, the sixth ligation product can be converted into a sixth modified product for use as an upstream peptide having the following formula:

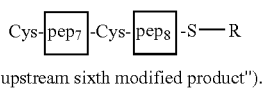

("upstream sixth modified product").

This modified peptide can then be used in any ligation with any downstream modified peptide or ligation product. The upstream sixth modified product can be reacted, for example, with the downstream first modified product.

Alternatively or additionally, the first modified product can be reacted as the downstream peptide with the fourth modified product acting as an upstream peptide to form a seventh ligation product containing an amide bond between the α-carbon of the C-terminal of the first modified product and the α-carbon of the N-terminal of the fourth modified product. The seventh ligation product will have the following formula:

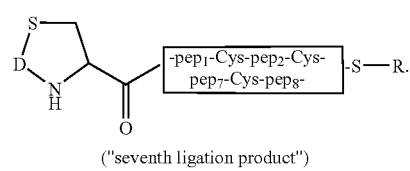

("seventh ligation product")

In further embodiments, the seventh ligation product can be converted into a seventh modified product for use as a downstream peptide having the following formula:

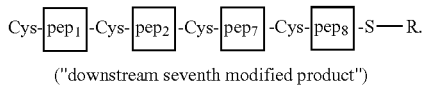

("downstream seventh modified product")

This modified peptide can then be used in any ligation with any upstream modified peptide or ligation product.

Additional synthesis strategies may include reacting a ninth modified peptide with an tenth modified peptide to form an eighth ligation product containing an amide bond between the α-carbon of the C-terminal of the ninth modified peptide and the α-carbon of the N-terminal of the tenth modified peptide, where the ninth modified peptide has the following formula:

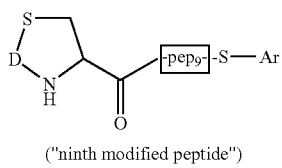

("ninth modified peptide")

and the tenth modified peptide has the following formula:

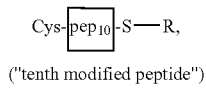

("tenth modified peptide")

which forms the eighth ligation product having the following formula:

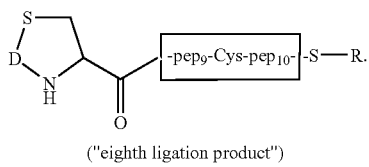

("eighth ligation product")

The eighth ligation product may be converted for use as a downstream peptide into an eighth modified product having the following formula:

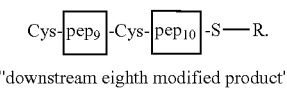

("downstream eighth modified product")

This modified peptide can then be used in any ligation with any upstream modified peptide or ligation product. The eighth modified product may or may not be reacted, for instance, with an eleventh modified peptide to form a ninth ligation product containing an amide bond between the α-carbon of the C-terminal of the eleventh modified peptide and the α-carbon of the N-terminal of the eighth modified product, where the eleventh modified peptide has the following formula:

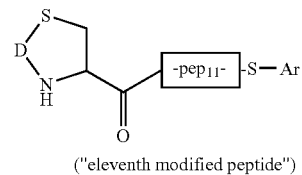

("eleventh modified peptide")

and the ninth ligation product has the following formula:

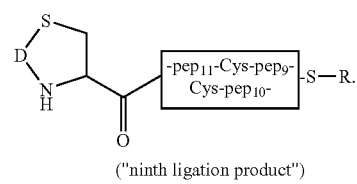

("ninth ligation product")

In further embodiments, the ninth ligation product is converted into a ninth modified product for use as a downstream peptide having the following formula:

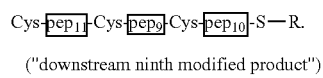

("downstream ninth modified product")

This modified peptide can then be used in any ligation with any upstream modified peptide or ligation product. For example, other embodiments may include, for example, reacting the fourth modified product as an upstream peptide with the ninth modified product as a downstream peptide to form a tenth ligation product containing an amide bond between the α-carbon of the C-terminal of the fourth modified product and the α-carbon of the N-terminal of the ninth modified product, where the tenth ligation product has the following formula:

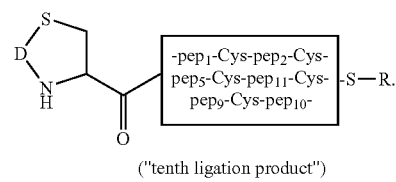

("tenth ligation product")

The tenth ligation product may then be converted into a modified product for use as downstream peptide having the following formula:

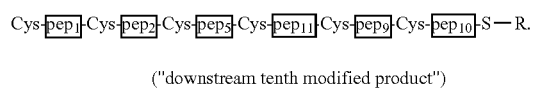

("downstream tenth modified product")

Other variations of the synthesis include reacting the first modified product with a twelfth modified peptide to form an eleventh ligation product containing an amide bond between the α-carbon of the C-terminal of the first modified product and the α-carbon of the N-terminal of the twelfth modified peptide, where the twelfth modified peptide has the following formula:

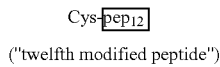

("twelfth modified peptide")

to produce the eleventh ligation product having the following formula:

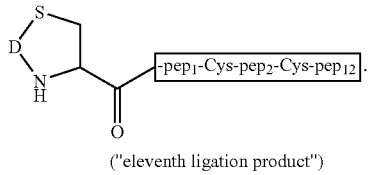

("eleventh ligation product")

In some embodiments, the eleventh ligation product is converted into an eleventh modified product having the following formula for use as a downstream modified product:

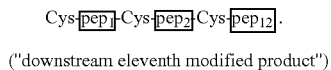

("downstream eleventh modified product")

This modified peptide can then be used in any ligation with any upstream modified peptide or ligation product.

A thirteenth modified peptide acting as an upstream peptide can then be reacted with the downstream eleventh modified product to form a thirteenth ligation product containing an amide bond between the α-carbon of the C-terminal of the thirteenth modified peptide and the α-carbon of the N-terminal of the eleventh modified product; the thirteenth modified peptide having the following formula:

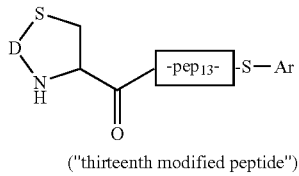

("thirteenth modified peptide")

and the twelfth ligation product having the following formula:

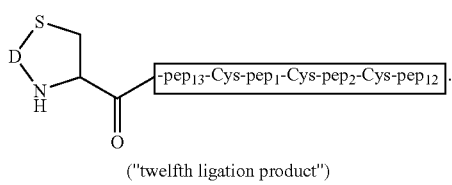

("twelfth ligation product")

The twelfth ligation product can be converted into a downstream peptide to form a twelfth modified product having the following formula:

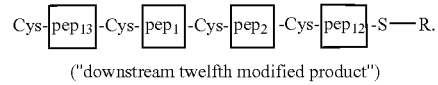

("downstream twelfth modified product")

This modified peptide can then be used in any ligation with any upstream modified peptide or ligation product.

In other embodiments, the fourth ligation product can be converted into an upstream peptide to form a modified product having the following formula:

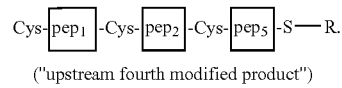

("upstream fourth modified product")

The fourth modified product acting as an upstream peptide can then be reacted with a fourteenth modified peptide to form a thirteenth ligation product containing an amide bond between the α-carbon of the C-terminal of the fourteenth modified peptide and the α-carbon of the N-terminal of the fourth modified product; where the fourteenth modified peptide has the following formula:

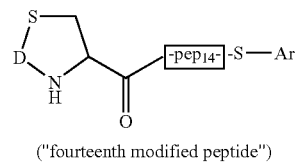

("fourteenth modified peptide")

and the thirteenth ligation product has the following formula:

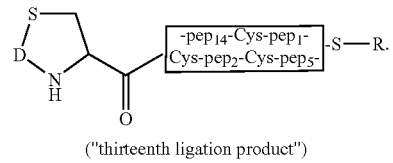

("thirteenth ligation product")

The thirteenth ligation product may then be converted into a thirteenth modified product having the following formula for use as a downstream peptide:

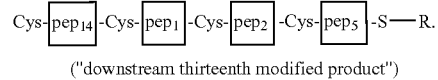

("downstream thirteenth modified product")

This modified peptide can then be used in any ligation with any upstream modified peptide or ligation product.

In other alternatives, the second ligation product can be converted into an upstream peptide having the following formula:

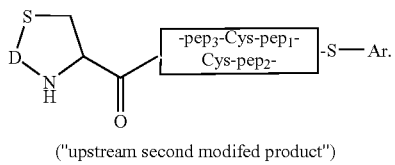

("upstream second modifed product")

The second modified product that can be used as an upstream peptide may be reacted with a fifteenth modified peptide to form a fourteenth ligation product containing an amide bond between the α-carbon of the C-terminal of the upstream second modified product and the α-carbon of the N-terminal of the fifteenth modified peptide; where the fifteenth modified peptide has the following formula:

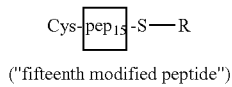

("fifteenth modified peptide")

and the fourteenth ligation product has the following formula:

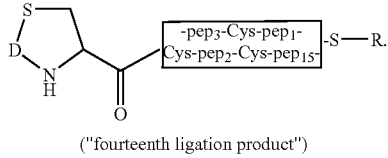

("fourteenth ligation product")

The fourteenth ligation product may be converted into a fourteenth modified product having the following formula, which can be used as a downstream peptide:

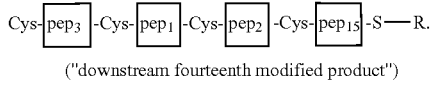

("downstream fourteenth modified product")

This modified peptide can then be used in any ligation with any upstream modified peptide or ligation product.

Additional possible reactions include reacting a sixteenth modified peptide with the second modified product acting as a downstream peptide to form a fifteenth ligation product containing an amide bond between the α-carbon of the C-terminal of the sixteenth modified peptide and the α-carbon of the N-terminal of the second modified product; where the sixteenth modified peptide has the following formula:

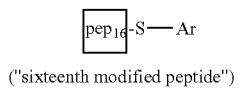

("sixteenth modified peptide")

and the fifteenth ligation product has the following formula:

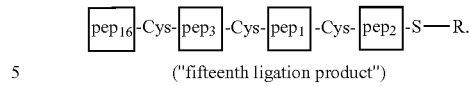

("fifteenth ligation product")

It is possible that the fifteenth ligation product can be converted into a fifteenth modified product having the following formula, so that it may be used as an upstream peptide:

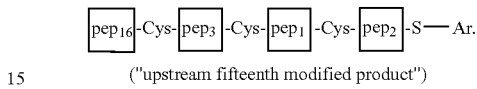

("upstream fifteenth modified product")

In other reactions a seventeenth modified peptide may be reacted with the first modified product acting as a downstream peptide to form a sixteenth ligation product containing an amide bond between the α-carbon of the C-terminal of the seventeenth modified peptide and the α-carbon of the N-terminal of the first modified product, where the seventeenth modified peptide has the following formula:

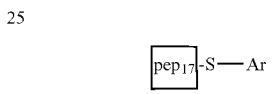

("seventeenth modified peptide")

and the sixteenth ligation product has the following formula:

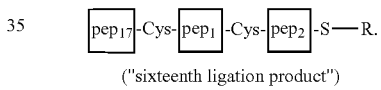

("sixteenth ligation product")

This sixteenth ligation product may be converted into an upstream peptide to form a sixteenth modified product having the following formula:

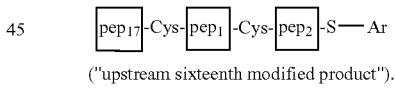

("upstream sixteenth modified product").

This modified peptide can then be used in any ligation with any downstream modified peptide or ligation product.

In other embodiments, an eighteenth modified peptide may be reacted with the fourth ligation product that has alternatively been converted into a downstream peptide ("downstream fourth modified peptide") to form a seventeenth ligation product containing an amide bond between the α-carbon of the C-terminal of the eighteenth modified peptide and the α-carbon of the N-terminal of the downstream fourth modified product, where the eighteenth modified peptide having the following formula:

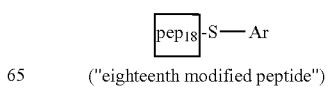

("eighteenth modified peptide")

and the fifteenth ligation product having the following formula:

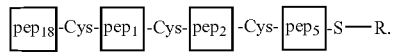

("seventeenth ligation product")

It is contemplated that the seventeenth ligation product can be converted into a peptide for use as an upstream peptide to form a seventeenth modified product having the following formula:

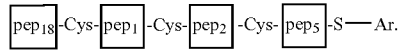

("upstream seventeenth modified product")

This modified peptide can then be used in any ligation with any downstream modified peptide or ligation product.

Other alternatives include reacting the upstream fourth ligation product with a nineteenth modified peptide to form an eighteenth ligation product containing an amide bond between the α-carbon of the C-terminal of the fourth ligation product and the α-carbon of the N-terminal of the nineteenth modified peptide, where the nineteenth modified peptide has the following formula:

("nineteenth modified peptide")

and the eighteenth ligation product has the following formula:

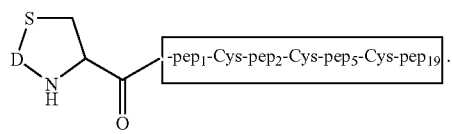

("eighteenth ligation product")

The present invention includes converting the eighteenth ligation product to form an eighteenth modified product for use as a downstream peptide having the following formula:

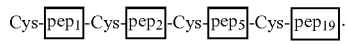

("downstream eighteenth modified product")

This modified peptide can then be used in any ligation with any upstream modified peptide or ligation product.

In other embodiments, the upstream fourth modified product may be reacted with a twentieth modified peptide to form a nineteenth ligation product containing an amide bond between the α-carbon of the C-terminal of the fourth modified product and the α-carbon of the N-terminal of the twentieth modified peptide, where the twentieth modified peptide has the following formula:

("twentieth modified peptide")

and the nineteenth ligation product having the following formula:

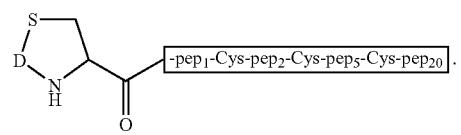

("nineteenth ligation product")

In certain cases, the nineteenth ligation product is modified into a downstream peptide to form a nineteenth modified product having the following formula:

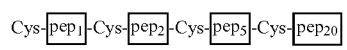

("downstream nineteenth modified product").

Other reactions include reacting a twenty-first modified peptide with the eleventh modified product acting as a downstream peptide to form a twentieth ligation product containing an amide bond between the α-carbon of the C-terminal of the twenty-first modified peptide and the α-carbon of the N-terminal of the eleventh modified product, where the twenty-first modified peptide has the following formula:

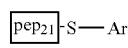

("twenty-first modified peptide")

and the twentieth ligation product has the following formula:

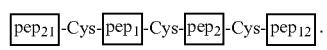

("twentieth ligation product")

In other embodiments, the sixteenth modified product acting as an upstream peptide may be reacted with a twenty-second modified peptide to form a twenty-first ligation product containing an amide bond between the α-carbon of the C-terminal of the sixteenth modified product and the α-carbon of the N-terminal of the twenty-second modified peptide, where the twenty-second modified peptide has the following formula:

("twenty-second modified peptide")

and the twenty-first ligation product has the following formula:

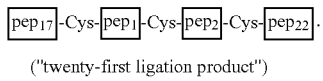

("twenty-first ligation product")

Other reactions include reacting the sixteenth modified product as an upstream peptide with a twenty-third modified peptide to form a twenty-second ligation product containing an amide bond between the α-carbon of the C-terminal of the sixteenth ligation product and the α-carbon of the N-terminal of the twenty-third modified peptide, where the twenty-third modified peptide has the following formula:

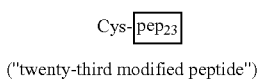

("twenty-third modified peptide")

and the twenty-second ligation product having the following formula:

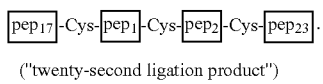

("twenty-second ligation product")

In another example of the invention, the upstream first modified product can be reacted with a twenty-fourth modified peptide to form a twenty-third ligation product containing an amide bond between the α-carbon of the C-terminal of the upstream first modified product and the α-carbon of the N-terminal of the twenty-fourth modified peptide, where the twenty-fourth modified peptide has the following formula:

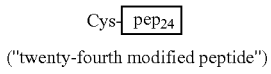

("twenty-fourth modified peptide")

and where the twenty-third ligation product has the following formula:

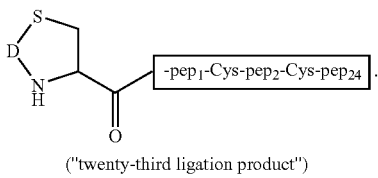

("twenty-third ligation product")

This reaction is similar to the reaction forming the fourth ligation product.

The twenty-third ligation product can be modified into a downstream peptide to form a downstream twenty-third modified product having the following formula:

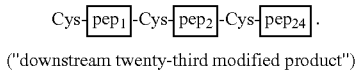

("downstream twenty-third modified product")

This modified peptide can then be used in any ligation with any upstream modified peptide or ligation product.

In a different embodiment, a twenty-fifth modified peptide can be reacted with the second modified product serving as a downstream peptide to form a twenty-fourth ligation product containing an amide bond between the α-carbon of the C-terminal of the twenty-fifth modified peptide and the α-carbon of the N-terminal of the downstream second modified product, where the twenty-fifth modified peptide has the following formula:

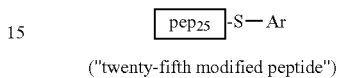

("twenty-fifth modified peptide")

and the twentieth ligation product has the following formula:

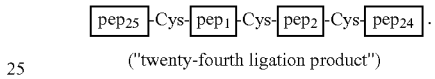

("twenty-fourth ligation product")

Generally, any ligation product can be modified into an upstream modified product or a downstream modified product. Subsequently, an upstream modified product can be reacted with a downstream peptide or a downstream modified product in a ligation reaction to form another ligation product. Likewise, a downstream modified product can be reacted with an upstream peptide or an upstream modified product in a ligation reaction to form another ligation product. Each resulting ligation product may then undergo subsequent modification so that it can be involved in another ligation reaction. Each of these steps may be repeated multiple times. As discussed herein, during the synthesis, the proper chemical group at each of the ultimate ends of the polypeptide will either be added by a ligation reaction or by chemical conversion of the group on the existing polypeptide.

Other methods of the invention involve a method comprising a reaction step, wherein a first modified peptide reacts with a second modified peptide in the presence of an exogenous catalyst that is not a thiophenol to form a first ligation product containing an amide bond between the α-carbon of the C-terminal of the first modified peptide and the α-carbon of the N-terminal of the second modified peptide; the first modified peptide having the following formula:

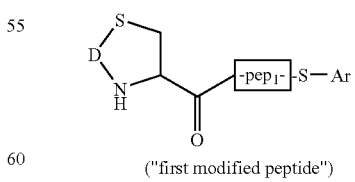

("first modified peptide")

wherein "D" represents an alkyl, aryl, aralkyl, or heterocyclic group, "Ar" represents a hydrogen atom, an alkyl, aryl, aralkyl, or heterocyclic group; and, the second modified peptide having the following formula:

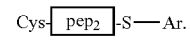

("second modified peptide")

The first ligation product will have the following formula:

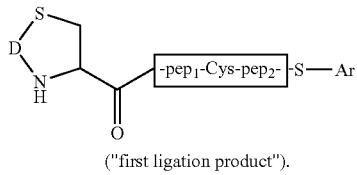

("first ligation product").

This method specifically involves an exogenous catalyst that is not a certain catalyst, such as thiophenol. In certain embodiments, it can be a catalyst listed in Table 3, or a derivative thereof.

For the different methods and compositions of the invention, in certain embodiments, R is an alkyl group. In still further embodiments, R is a hydrogen atom, while in others R is —$CH_2CH_2CONHCH(CH_2CH(CH_3)_2)COOH$. Moreover, in specific embodiments Ar is an aryl group. It is contemplated that Ar can be a substituted or unsubstituted: phenyl, pyridyl, or pyrimidyl group. In particular embodiments, the phenyl group is unsubstituted. Alternatively, the phenyl group can have one or more substituents. The substituents include but are not limited to a carboxylic acid, chloro, nitro, methyl, hydroxyl, acetic acid, methoxy, or amino. In certain cases, Ar is —$CH_2CH_2SO_3Na$, while in others Ar is a benzyl group. Furthermore, in particular cases D is a methylene group. Consequently, the present invention specifically contemplates a method involving peptides in which R is —$CH_2CH_2CONHCH(CH_2CH(CH_3)_2)COOH$, Ar is a phenyl group, and D is a methylene group.

At some point during the synthesis, the chemical groups of the N- and C-terminal residues of an end product polypeptide can be addressed so that they reflect the chemical groups observed in a native protein. These groups are referred to as the "proper" groups. The proper N- or C-terminal ends can be achieved by a number of ways. These include, but are not limited to, employing as an upstream peptide a peptide with a proper N-terminal end in a ligation reaction or employing as a downstream peptide a peptide with a proper C-terminal end in a ligation reaction. In some embodiments, the proper chemical group at each of the ultimate ends of the polypeptide will either be added by a ligation reaction or by chemical conversion of the group on the existing polypeptide. In the former case, any modified peptide may differ with respect to the chemical group at a terminal residue not involved in a ligation reaction. For example, a peptide employed as a downstream peptide may have a carboxylate on the C-terminal residue or a peptide employed as an upstream peptide may have a residue at the N-terminal end that is not a cysteine (protected or unprotected). A downstream peptide with a native residue on the C-terminal end is considered to lack a leaving group. Alternatively or additionally, a ligation product can be converted into a polypeptide with the proper chemical groups. A ligation product with a protected chemical group on the N-terminal residue can be converted into an unprotected chemical group so that the residue has the same chemical structure as a native polypeptide. Similarly, a ligation product with a chemical group that is not a carboxylic acid or carboxylate and that has a leaving group on the C-terminal residue can be converted to have a COOH or COO⁻ chemical structure.

Therefore, methods of the invention can involve 1) reacting an upstream peptide having an α-amino group (—$NH_3^+$) at its N-terminal with a downstream peptide to form a ligation product; 2) reacting a downstream peptide having an α-carboxylic acid (—COOH) or carboxylate group (—COO⁻) at the C-terminal with an upstream peptide to form a ligation product; 3) converting a protected amino acid at the N-terminal end of a ligation product into an unprotected amino acid; and/or 4) converting a chemical group on C-terminal residue of a ligation product into a carboxylate group. It is specifically contemplated that with respect to 1), the residue at the N-terminal end of the upstream peptide is not a cysteyl residue.

Peptides and ligation products used in ligation reactions will, in most embodiments, contain unprotected amino acid residues with the exception of a residue at the N-terminal end (particularly at the N-terminal end of an upstream peptide).

In methods of the invention a ligation product may be formed under reaction conditions that include an exogenous catalyst. A "catalyst" refers to a compound that initiates or accelerates the reaction but is not affected itself by the reaction. An "exogenous catalyst" refers to one that is separately added to the reaction, in contrast to one that may be present as the result of the chemical reaction itself. It is contemplated that in some cases the exogenous catalyst is not a thiophenol. In certain embodiments, the ligation reaction specifically does not contain an exogenous catalyst.

In addition, in certain embodiments, the upstream peptide is added to a reaction mixture containing the downstream peptide or the downstream peptide is added to a reaction mixture containing the upstream peptide. In some cases, one peptide is added to a reaction mixture containing the other peptide at a rate of at least about, at most about, or about 1, 5, 10, 15, 20, 25, 30, 35, 40, 45, 50, 55, 60, 65, 70, 75, 80, 85, 90, 95, 100, 200, 300, 400, 500, 600, 700, 800, 900, 1000 μl/min, or any range derivable therein into a reaction volume on the order of milliliters (0.1-1000). Alternatively, these rates may be scaled-up for manufacturing large quantities of polypeptides or proteins on a multi-gram, multi-kilogram, or multi-ton scale. Furthermore, it is contemplated that reaction components may be added to a reaction mixture by a fed-batch process. Alternatively, the reaction may be done in batch, meaning all of the reaction components are mixed together.

The reaction mixture may contain an aqueous buffer. Moreover, it may have an initial pH of about, at least about, or at most about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0 or more (or any range derivable therein).

Methods of the invention may further involve purifying a compound. The term "purify" is used according to its ordinary and plain meaning in the chemical arts. It is contemplated that a peptide component in a ligation reaction may first be purified prior to reacting it with another peptide. For example, the peptide component may be a modified peptide component that is purified with respect to either unmodified peptides and/or any other compound in the reaction mixture. Moreover, a ligation product that is the result of a ligation reaction may be purified. It may be purified with respect to a downstream and/or upstream peptide, as well as with respect to any other reaction component.

In some embodiments of the invention, it is contemplated that the extent of homogeneity is specified. The desired polypeptide may be contained in a composition that is about, at least about, or at most about 40, 45, 50, 55, 60, 65, 70, 75, 80, 85, 90, 95, 96, 97, 98, 99 or more percent (or any range derivable therein) homogeneous or pure.

The present invention also concerns compositions. In some embodiments the composition is a peptide having the following formula:

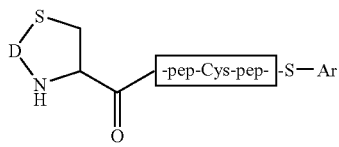

wherein: "D" represents an alkyl, aryl, aralkyl, or heterocyclic group, "Ar" represents an alkyl, aryl, aralkyl, or heterocyclic group, and "pep" represents an unbranched chain of at least four amino acid residues linked by peptide bonds. The term "Cys" is understood to refer to a cysteine residue. It is contemplated that the amino acid sequences on each side of the recited cysteine may be different or the same. Moreover, it is contemplated that in some embodiments, the peptide composition has at least one cysteine that is flanked by amino acid sequences that are at least 10 residues in length.

In specific embodiments, a peptide composition has Ar that is a phenyl, a D that is a methylene, and a cysteine flanked by amino acid sequences that are at least 10 residues in length.

One of the embodiments of the invention comprises a method of synthesizing a polypeptide using a kinetically controlled fully convergent approach. For example, a polypeptide can be synthesized in the following procedure.

First, four peptides are obtained: (1) a first C-activated peptide, having an N-terminal-protected cysteinyl residue or an N-terminal non-cysteinyl residue and a good C-terminal thiol-based leaving group, (2) a first N-deprotected peptide, having an N-terminal unprotected cysteinyl residue and a weak C-terminal thiol-based leaving group, (3) a second C-activated peptide, having an N-terminal-protected cysteinyl residue and a good C-terminal thiol-based leaving group, and (4) a second N-deprotected peptide, having an N-terminal unprotected cysteinyl residue and a C-terminal α-carboxylate, α-carboxamide, or a weak C-terminal thiol-based leaving group. These four peptides can be obtained in any order. Furthermore, the invention contemplates that part or all of this first step can be accomplished in-situ. For example, one or more of the above peptides may be "obtained" without that peptide being isolated or purified. In some embodiments, the four peptides are obtained at the same time. In other embodiments, the four peptides are obtained in 1, 2, 3, 4, 5, 6, 7, 8, 9, 10, or more discrete steps. In some embodiments, the additional discrete steps can involve chemical ligation, recombinant synthesis, purification, work-up, neutralization, filtration, lyophilization, chromatography, washing, extraction, salt-exchange, protection, deprotection, sampling, and analysis.

Second, the first C-activated peptide is combined with the first N-deprotected peptide to form a first ligation product having an amide bond between the α-carbon of the C-terminal residue of the first C-activated peptide and the α-carbon of the N-terminal of the first N-deprotected peptide. Either before, during, or after the above reaction, the second C-activated peptide is combined with the second N-deprotected peptide to form a second ligation product having an amide bond between the α-carbon of the C-terminal residue of the second C-activated peptide and the α-carbon of the N-terminal of the second N-deprotected peptide. In certain embodiments of the invention, the two ligation reactions occur in physically separated reaction vessels. In other embodiments, the two combination reactions occur in the same reaction vessel, whereby the two ligation products are formed in a one-pot synthesis. In some of these embodiments, the two combination reactions occur in a one-pot reaction when the first C-activated peptide and the second C-activated peptide are chemically identical. In some embodiments, one or both of the ligation reactions occur in one discrete step. In other embodiments, one or both of the ligation reactions occur in 1, 2, 3, 4, 5, 6, 7, 8, 9, 10, or more discrete steps. In some embodiments the additional discrete steps can involve purification, work-up, neutralization, filtration, lyophilization, chromatography, washing, extraction, salt-exchange, protection, deprotection, sampling, and analysis.

Third, the weak C-terminal thiol-based leaving group of the first ligation product or the second ligation product is replaced with a good C-terminal thiol-based leaving group to form a C-activated ligation product. Either before, during, after, or independent of the above replacement, the N-terminal-protected cysteinyl residue of the first ligation product or the second ligation product is deprotected to form an N-deprotected ligation product. In some embodiments, one or both of the replacement reaction and the deprotection reaction occurs in one discrete step. In other embodiments, one or both of the replacement reaction and the deprotection reaction occurs in 1, 2, 3, 4, 5, 6, 7, 8, 9, 10, or more discrete steps. In some embodiments, the additional discrete steps can involve purification, work-up, neutralization, filtration, lyophilization, chromatography, washing, extraction, salt-exchange, protection, deprotection, sampling, and analysis.

Fourth, the C-activated ligation product is combined with the N-deprotected ligation product to form a third ligation product having an amide bond between the α-carbon of the C-terminal residue of the C-activated ligation product and the α-carbon of the N-terminal of the N-deprotected ligation product, whereby the third ligation product is a polypeptide. In some embodiments, the ligation reaction occurs in one discrete step. In other embodiments, the ligation reactions occur in 1, 2, 3, 4, 5, 6, 7, 8, 9, 10, or more discrete steps. In some embodiments the additional discrete steps can involve purification, work-up, neutralization, filtration, lyophilization, chromatography, washing, extraction, salt-exchange, protection, deprotection, sampling, and analysis.

In certain embodiments, the four step synthesis of a polypeptide, outlined above, may be accomplished in less than four steps or more than four steps. One, two, three, or four of the steps may occur in a one-pot reaction.

In some embodiments, the third ligation product may undergo further deprotections, replacements, ligations, derivatizations, or purifications. Furthermore, in some embodiments, the synthesized polypeptide can then be used in any additional convergent and non-convergent synthetic schemes to produce larger polypeptides and/or proteins.

In some embodiments where different weak thiol-based leaving groups are used, the weak C-terminal thiol-based leaving group of the first ligation product or the second ligation product is replaced with a good C-terminal thiol-based leaving group is omitted. This step can be omitted when the differential reactivity between the two different weak thiol-based leaving groups is sufficient for a kinetically controlled ligation reaction to take place. For example, in certain embodiments, the first or the second ligation product can be combined with the N-deprotected ligation product to form the third ligation product. In certain of these embodiments, the first of the second ligation product has a less weak C-terminal thiol-based leaving group than the N-deprotected ligation product. In certain embodiments, all three ligation reactions occur in the same reaction vessel. In some embodiments the third ligation product is formed in a one-pot synthesis.

In certain embodiments, the first C-activated peptide and the second C-activated peptide can be chemically identical. In other embodiments, they may be chemically different. In some embodiments, the first N-deprotected peptide and the second N-deprotected peptide can be chemically identical. In other embodiments, they may be chemically different. In certain embodiments, two or more of the first C-activated peptide, the second C-activated peptide, the first N-deprotected peptide, and the second N-deprotected peptide can have the same residue sequence.

The term "N-deprotected" is used synonymously with the term "N-activated." The term "cysteinyl" is used synonymously with the term "cysteyl." The term "thiol-based leaving group" refers to a leaving group that has the structure —SH, —SR, wherein "R" represents a $C_1$-$C_{10}$-alkyl, $C_2$-$C_{10}$-alkenyl, $C_2$-$C_{10}$-alkynyl, $C_6$-$C_{10}$-aryl, $C_7$-$C_{10}$-aralkyl, $C_1$-$C_{10}$-heteroaryl, $C_2$-$C_{10}$-heteroaralkyl, $C_1$-$C_{10}$-acyl, alkyl, aralkyl, aryl, or heterocyclic group.

In some embodiments of the present invention, the term "leaving group" may be modified with the adjectives "good" or "weak." The adjectives are relative terms; when they modify "leaving group," they qualify the ease with which one leaving group can be substituted relative to another leaving group. In the context of the present invention, a "good leaving group" is more easily substituted than a "weak leaving group." Similarly, in the context of the present invention, a "good leaving group" is more reactive than a "weak leaving group." In some embodiments, the "weak" C-terminal thiol-based leaving groups are the same. Similarly, in some embodiments, the "good" C-terminal thiol-based leaving groups of the first C-activated peptide and the second C-activated peptide are the same. An embodiment in which there were only two types of leaving groups, e.g. "good leaving groups" and "weak leaving groups," would be considered a system having two levels of leaving group reactivity.

In other embodiments, the good C-terminal thiol-based leaving groups of the first C-activated peptide and the second C-activated peptide are different. In the case where the good C-terminal thiol-based leaving groups are different, one leaving group will be more reactive than the other. That is, one leaving group may be substituted more readily than the other. Similarly, in some embodiments, the weak C-terminal thiol-based leaving groups are different. In the case where the weak C-terminal thiol-based leaving groups are different, one leaving group will be more reactive than the other. That is, one leaving group may be substituted more readily than the other one. An embodiment in which there are only three types of leaving groups would be considered a system having three-levels of leaving group reactivity.

In certain embodiments, having different weak thiol-based leaving groups allows for a kinetically controlled convergent method of synthesizing a polypeptide not requiring a step of replacing the weak thiol-based leaving group of any of the ligation products. Furthermore, the invention contemplates a reactivity series of leaving groups which would allow a synthetic approach whereby not only four peptides are convergently ligated to form a polypeptide without requiring a step of replacing the weak thiol-based leaving group of any of the ligation products, but also an approach whereby 3, 4, 5, 6, 7, 8, 9, 10, 11, 12, 13, 14, 15, or 16 peptides are convergently or nonconvergently ligated to form a polypeptide without requiring a step of replacing the weak thiol-based leaving group of any of the ligation products. In certain embodiments, the invention contemplates using one or more "very weak," "weak," "less weak," "less good," "good," or "very good" thiol-based or thioester-based leaving groups.

In some embodiments of the invention, the first C-activated peptide, the first N-deprotected peptide, the second C-activated peptide, the second N-deprotected peptide, the first ligation product, the second ligation product, the N-deprotected ligation product, the C-activated ligation product, the third ligation product, or the polypeptide each independently contain one or more internal residues with protected side chains. In certain embodiments, the internal residues with protected side chains are protected cysteinyl residues. For example, in certain embodiments, the protected cysteinyl residues are protected with a protection group selected from the group consisting of acetamidomethyl (Acm), trimethylacetamidomethyl (Tacm), and phenylacetamidomethyl (Phacm). In certain of these embodiments, the protection group is Acm.

The invention contemplates additional steps to allow for the native chemical ligation of polypeptides having inconveniently-spaced cysteinyl residues. Cysteinyl residues may be rare or absent in many proteins; however, the native chemical ligation method of this invention may be extended to the synthesis of these polypeptides by combining selective desulfurization with native-chemical ligation. Such a process can be used to convert cysteinyl residues in a polypeptide into alanyl residues, which occur more frequently in most proteins. The desulfurization is selective in that it would not convert those cysteinyl residues that had been protected prior to being subjected to the selective desulfurization conditions. In other embodiments, for example where the target polypeptide doesn't contain any cysteinyl residues, a non-selective desulfurization procedure can be used.

In some embodiments, one or more of the first C-activated peptide, the first N-deprotected peptide, the second C-activated peptide, the second N-deprotected peptide, the first ligation product, the second ligation product, the N-deprotected ligation product, the C-activated ligation product, the third ligation product, or the polypeptide is selectively desulfurized to convert cysteinyl residues into alanyl residues, whereby neither the internal residues with protected side chains nor the thiol-based leaving groups are desulfurized. In certain embodiments some protected cysteinyl residues are converted into alanyl residues. For example, under certain selective desulfurization conditions, thiazolidine-protected cysteinyl residues are converted into alanyl residues. In some of these embodiments, Acm-protected cysteinyl residues are not converted into alanyl residues. In further of these embodiments, thiol-based leaving groups are not desulfurized under selective desulfurization conditions. In certain embodiments, selective desulfurization is accomplished using Raney nickel as a catalyst.

In other embodiments, any of the internal residues with protected side chains from one or more of the first C-activated peptide, the first N-deprotected peptide, the second C-activated peptide, the second N-deprotected peptide, the first ligation product, the second ligation product, the N-deprotected ligation product, the C-activated ligation product, the third ligation product, or the polypeptide can be deprotected, regardless of whether the protected residues are protected cysteinyl groups or other protected residues.

In some embodiments of the invention, the good C-terminal thiol-based leaving group is a substituted or unsubstituted thiophenol. In non-limiting embodiments, the good C-terminal thiol-based leaving groups can have the structure —$SR_1$, wherein $R_1$ is a substituted or unsubstituted $C_6$-$C_{15}$-aryl. The term "unsubstituted $C_6$-$C_{15}$-aryl" refers to a radical having an aromatic carbon atom as the point of attachment, further having a total of 6 to 15 aromatic or nonaromatic carbon atoms, 5 or more hydrogen atoms, and no heteroatoms. The term "substituted $C_6$-$C_{15}$-aryl" refers to a radical having an aromatic carbon atom as the point of attachment; further having a total of 6 to 15 aromatic or non-aromatic carbon atoms, 0, 1, or more than one hydrogen atom, and at least one nonaromatic heteroatom, wherein each heteroatom is independently selected from the group consisting of N, O, F, Cl, Br, I, Si, P, and S. In certain embodiments, the good C-terminal thiol-based leaving group is —$SR_1$, wherein $R_1$ is chosen from the group consisting of —$C_6H_4COOH$, —$C_6H_4COO^-$, —$C_6H_4Cl$, —$C_6H_4NO_2$, —$C_6H_4CH_3$, —$C_6H_4OH$, —$C_6H_4OCOCH_3$, —$C_6H_4COOCH_3$, —$C_6H_4CH_2COOH$, —$C_6H_4CH_2COO^-$, —$C_6H_4CONH_2$, and —$C_6H_4CH_2CONH_2$. In certain of these embodiments, at least one of the good C-terminal thiol-based leaving groups is —$C_6H_4CH_2COOH$ or —$C_6H_4CH_2COO^-$. The group "—$C_6H_4CH_2COO^-$" is the deprotonated form of "—$C_6H_4CH_2COOH$." A person of skill in the art will recognize that a wide variety of counterions will be compatible with the "—$C_6H_4CH_2COO^-$" group. For example, in certain embodiments, the counterion will be monovalent or divalent. Non-limiting examples of counterions include $Na^+$, $K^+$, $Mg^{+2}$, and quaternary ammonium ions. In certain embodiments, $R_1$ is an aryl group.

In some embodiments of the invention, the weak C-terminal thiol-based leaving group is —SH, —$S^-$ or —$SR_2$, wherein $R_2$ represents a substituted or unsubstituted version of $C_1$-$C_{15}$-alkyl or $C_1$-$C_{15}$-aralkyl. The group "—$S^-$" is the deprotonated form of "—SH." A person of skill in the art will recognize that a wide variety of counterions will be compatible with the "—$S^-$" group. For example, in certain embodiments, the counterion will be monovalent or divalent. Non-limiting examples of counterions include $Na^+$, $K^+$, $Mg^{+2}$, and quaternary ammonium ions. In certain embodiments, $R_2$ is an alkyl or an alkaryl group.

The term "unsubstituted $C_1$-$C_{15}$-alkyl" refers to a radical that may be linear or branched, cyclic or acyclic, containing 1 to 15 nonaromatic saturated carbon atoms, 3 or more hydrogen atoms, and no heteroatoms. The term "substituted $C_1$-$C_{15}$-alkyl" refers to a radical having a saturated carbon atom as the point of attachment, no carbon-carbon double or triple bonds; further having a linear or branched, cyclic or acyclic structure; further having a total of 1 to 15 nonaromatic carbon atoms, 0, 1, or more than one hydrogen atom, at least one heteroatom, wherein each heteroatom is independently selected from the group consisting of N, O, F, Cl, Br, I, Si, P, and S. The term "unsubstituted $C_7$-$C_{15}$-aralkyl" refers to a radical having a saturated carbon atom as the point of attachment, further having a total of 7 to 15 aromatic or nonaromatic carbon atoms, wherein at least 6 of the carbon atoms form an aromatic ring, 7 or more hydrogen atoms, and no heteroatoms. The term "substituted $C_7$-$C_{15}$-aralkyl" refers to a radical having a saturated carbon atom as the point of attachment; further having a total of 7 to 15 aromatic or nonaromatic carbon atoms, wherein at least 6 of the carbon atoms form an aromatic ring, 0, 1, or more than one hydrogen atom, and at least one nonaromatic heteroatom, wherein each heteroatom is independently selected from the group consisting of N, O, F, Cl, Br, I, Si, P, and S.

In certain of these embodiments, $R_2$ is —$CH_2CH_2SO_3Na$, —$CH_2SO_3Na$, —$CH_2CH_2CONHCH(R_3)COOH$, $CH_2CONHCH(R_3)COOH$, —$CH_2CH_2CONHCH(R_3)COO^-$, —$CH_2CONHCH(R_3)COO^-$, —$CH_2CH_2CONHCH(R_3)CONH_2$, —$CH_2CONHCH(R_3)CONH_2$, $CH_2CH_2CO(Arg)_nOH$ or —$CH_2CH_2CO(Arg)_nNH_2$, wherein $R_3$ is H, amino, hydroxyl, halo, —$NHR_4$, $NR_4R_5$, —$OR_4$, or a substituted or unsubstituted version of $C_1$-$C_{10}$-alkyl, $C_2$-$C_{10}$-alkenyl, $C_2$-$C_{10}$-alkynyl, $C_6$-$C_{10}$-aryl, $C_7$-$C_{10}$-aralkyl, $C_1$-$C_{10}$-heteroaryl, $C_2$-$C_{10}$-heteroaralkyl, or $C_1$-$C_{10}$-acyl; wherein $R_1$ and $R_5$ are independently H or a substituted or unsubstituted version of $C_1$-$C_{10}$-alkyl, $C_2$-$C_{10}$-alkenyl, $C_2$-$C_{10}$-alkynyl, $C_6$-$C_{10}$-aryl, $C_7$-$C_{10}$-aralkyl, $C_1$-$C_{10}$-heteroaryl, $C_2$-$C_{10}$-heteroaralkyl, or $C_1$-$C_{10}$-acyl; further wherein Arg is an arginyl residue, and n is an integer from 1 to 6 and $(Arg)_{4-6}$ is SEQ ID NO:34, SEQ ID NO:35, or SEQ ID NO:36, respectively. In some embodiments, $R_3$, $R_4$, or $R_5$ is an alkyl, aryl, or aralkyl, or heterocyclic group.

The term "unsubstituted $C_1$-$C_{10}$-alkyl" refers to a radical that may be linear or branched, cyclic or acyclic, containing 1 to 10 nonaromatic saturated carbon atoms, 3 or more hydrogen atoms, and no heteroatoms.

The term "substituted $C_1$-$C_{10}$-alkyl" refers to a radical having a saturated carbon atom as the point of attachment, no carbon-carbon double or triple bonds; further having a linear or branched, cyclic or acyclic structure; further having a total of 1 to 10 nonaromatic carbon atoms, 0, 1, or more than one hydrogen atom, at least one heteroatom, wherein each heteroatom is independently selected from the group consisting of N, O, F, Cl, Br, I, Si, P, and S.

The term "unsubstituted $C_2$-$C_{10}$-alkenyl" refers to a radical that may be linear or branched, cyclic or acyclic, containing at least one carbon-carbon double bond, 2 to 10 nonaromatic carbon atoms, 3 or more hydrogen atoms, and no heteroatoms.

The term "substituted $C_2$-$C_{10}$-alkenyl" refers to a radical having a nonaromatic carbon atom as the point of attachment and at least one nonaromatic carbon-carbon double bond, but no carbon-carbon triple bonds; further having a linear or branched, cyclic or acyclic structure; further having a total of 2 to 10 aromatic or nonaromatic carbon atoms, 0, 1, or more than one hydrogen atom, at least one heteroatom, wherein each heteroatom is independently selected from the group consisting of N, O, F, Cl, Br, I, Si, P, and S.

The term "unsubstituted $C_2$-$C_{10}$-alkynyl" refers to a radical that may be linear or branched, cyclic or acyclic, containing at least one carbon-carbon triple bond, 2 to 10 nonaromatic carbon atoms, at least one hydrogen atoms, and no heteroatoms.

The term "substituted $C_2$-$C_{10}$-alkynyl" refers to a radical having a nonaromatic carbon atom as the point of attachment and at least one nonaromatic carbon-carbon triple bond, further having a linear or branched, cyclic or acyclic structure, and having a total of 2 to 10 aromatic or nonaromatic carbon atoms, 0, 1, or more than one hydrogen atom, and at least one heteroatom, wherein each heteroatom is independently selected from the group consisting of N, O, F, Cl, Br, I, Si, P, and S.

The term "unsubstituted $C_6$-$C_{10}$-aryl" refers to a radical having an aromatic carbon atom as the point of attachment, further having a total of 6 to 10 aromatic or nonaromatic carbon atoms, 5 or more hydrogen atoms, and no heteroatoms.

The term "substituted $C_6$-$C_{10}$-aryl" refers to a radical having an aromatic carbon atom as the point of attachment; further having a total of 6 to 10 aromatic or non-aromatic carbon atoms, 0, 1, or more than one hydrogen atom, and at least one nonaromatic heteroatom, wherein each heteroatom is independently selected from the group consisting of N, O, F, Cl, Br, I, Si, P, and S.

The term "unsubstituted $C_7$-$C_{10}$-aralkyl" refers to a radical having a saturated carbon atom as the point of attachment, further having a total of 7 to 10 aromatic or nonaromatic carbon atoms, wherein at least 6 of the carbon atoms form an aromatic ring, 7 or more hydrogen atoms, and no heteroatoms.

The term "substituted $C_7$-$C_{10}$-aralkyl" refers to a radical having a saturated carbon atom as the point of attachment; further having a total of 7 to 10 aromatic or nonaromatic carbon atoms, wherein at least 6 of the carbon atoms form an aromatic ring, 0, 1, or more than one hydrogen atom, and at least one nonaromatic heteroatom, wherein each heteroatom is independently selected from the group consisting of N, O, F, Cl, Br, I, Si, P, and S.

The term "unsubstituted $C_1$-$C_{10}$-heteroaryl" refers to a radical having an aromatic atom as the point of attachment, further having a total of 1 to 10 aromatic or non-aromatic carbon atoms, at least one hydrogen atom, at least one aromatic heteroatom, and no nonaromatic heteroatoms; wherein each heteroatom is independently selected from the group consisting of N, O, F, Cl, Br, I, Si, P, and S.

The term "substituted $C_1$-$C_{10}$-heteroaryl" refers to a radical having an aromatic atom as the point of attachment, further having a total of 1 to 10 aromatic or non-aromatic carbon atoms, 0, 1, or more than one hydrogen atom, at least one aromatic heteroatom, and at least one nonaromatic heteroatom; wherein each heteroatom is independently selected from the group consisting of N, O, F, Cl, Br, I, Si, P, and S.

The term "unsubstituted $C_2$-$C_{10}$-heteroaralkyl" refers to a radical having, a saturated carbon atom as the point of attachment, further having a total of 2 to 10 aromatic or non-aromatic carbon atoms, at least 3 hydrogen atoms, at least one aromatic heteroatom, and no nonaromatic heteroatoms, wherein each heteroatom is independently selected from the group consisting of N, O, F, Cl, Br, I, Si, P, and S; wherein at least 3 of the atoms form an aromatic ring.

The term "substituted $C_2$-$C_{10}$-heteroaralkyl" refers to a radical having a saturated carbon atom as the point of attachment, further having a total of 2 to 10 aromatic or non-aromatic carbon atoms, 0, 1, or more than one hydrogen atom, at least one aromatic heteroatom, and at least one nonaromatic heteroatom, wherein each heteroatom is independently selected from the group consisting of N, O, F, Cl, Br, I, Si, P, and S; wherein at least 3 of the atoms form an aromatic ring.

The term "unsubstituted $C_1$-$C_{10}$-acyl" refers to a radical having one carbonyl group, wherein the carbon atom of the carbonyl group is the point of attachment, further having a linear or branched, cyclic or acyclic structure; further having a total of 1 to 10 aromatic or nonaromatic carbon atoms, 1 or more hydrogen atoms, one oxygen atom, and no additional heteroatoms.

The term "substituted $C_1$-$C_{10}$-acyl" refers to a radical having one carbonyl group, wherein the carbon atom of the carbonyl group is the point of attachment, further having a linear or branched, cyclic or acyclic structure; further having a total of 1 to 10 aromatic or nonaromatic carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S.

In some embodiments of the invention, the N-terminal protected cysteinyl residue has a linking group connecting its thiol group to its amino group. In certain of these embodiments, the linking group is —$CH_2$—, —$CH(R_6)$—, or —$C(R_6)(R_7)$—, wherein $R_6$ and $R_7$ are each independently amino, hydroxyl, halo, —$NHR_8$, —$NR_8R_9$, —$OR_8$, or a substituted or unsubstituted version of $C_1$-$C_{10}$-alkyl, $C_2$-$C_{10}$-alkenyl, $C_2$-$C_{10}$-alkynyl, $C_6$-$C_{10}$-aryl, $C_7$-$C_{10}$-aralkyl, $C_1$-$C_{10}$-heteroaryl, $C_2$-$C_{10}$-heteroaralkyl, or $C_1$-$C_{10}$-acyl; wherein $R_8$ and $R_9$ are each independently H or a substituted or unsubstituted version of $C_1$-$C_{10}$-alkyl, $C_2$-$C_{10}$-alkenyl, $C_2$-$C_{10}$-alkynyl, $C_6$-$C_{10}$-aryl, $C_7$-$C_{10}$-aralkyl, $C_1$-$C_{10}$-heteroaryl, $C_2$-$C_{10}$-heteroaralkyl, or $C_1$-$C_{10}$-acyl. In certain embodiments, the N-terminal protected cysteinyl residue contains a thiazolidine ring structure. In some embodiments, $R_6$, $R_7$, $R_9$, or $R_{10}$ is an alkyl, aryl, or aralkyl, or heterocyclic group.

The invention contemplates elongating the polypeptide formed from a convergent or sequential synthesis by means of additional ligation reactions. Such an elongation may be accomplished in either direction along the peptide backbone. That is, the polypeptide may be elongated by ligating an additional peptide upstream of the polypeptide, or ligating an additional peptide downstream of the polypeptide. For example, a polypeptide may be elongated in the C to N direction by means of additional steps. In certain embodiments, a third C-activated peptide having an N-terminal-protected cysteinyl residue and a good C-terminal thiol-based leaving group is obtained. The N-terminal-protected cysteinyl residue of the third ligation product is deprotected to form a further N-deprotected ligation product. The third C-activated peptide is combined with the further N-deprotected ligation product to form a fourth ligation product, having an amide bond between the α-carbon of the C-terminal residue of the third C-activated peptide and the α-carbon of the N-terminal of the further N-deprotected ligation product. The fourth ligation product is a polypeptide.

The methods of this invention can also be used to elongate a polypeptide in the N to C direction. For example, the invention contemplates obtaining a third N-deprotected peptide, having an N-terminal unprotected cysteinyl residue and one of the weak C-terminal thiol-based leaving groups, replacing the weak C-terminal thiol-based leaving group of the third ligation product with a good C-terminal thiol-based leaving group to form a further C-activated ligation product, and combining the further C-activated ligation product with the third N-deprotected peptide to form a fifth ligation product, having an amide bond between the α-carbon of the C-terminal residue of the further C-activated ligation product and the α-carbon of the N-terminal of the third N-deprotected peptide, whereby the fifth ligation product is a polypeptide.

In other embodiments, one or both of the first C-activated peptide and the second C-activated peptide is a C-activated ligation product, formed prior to its use in a convergent or sequential synthesis of a polypeptide. It is contemplated that the convergent and sequential methods of this reaction can be repeated with peptides, polypeptides, and ligation products formed in a previous application of the methods of this invention. That is, the weak C-terminal thiol-based leaving group of the third ligation product can be replaced with a good C-terminal thiol-based leaving group, thereby forming a polypeptide that would function as a first C-activated peptide or a second C-activated peptide in a subsequent kinetically-controlled convergent or non-convergent synthesis of a larger polypeptide or protein.

In other embodiments, the N-terminal-protected cysteinyl residue of the third ligation product can be deprotected, thereby forming a peptide that would function as a first N-deprotected peptide or a second N-deprotected peptide in a subsequent kinetically controlled convergent or non-convergent synthesis of a polypeptide. In certain embodiments, one or both of the first N-deprotected peptide and the second N-deprotected peptide is a N-deprotected ligation product, formed prior to its use in the method of convergent or sequential synthesis of a polypeptide.

In non-limiting embodiments, the combining of any of the C-activated peptides or ligation products with any of the N-deprotected peptides or ligation products to form any ligation product or polypeptide occurs in an aqueous buffer having a pH between 6 and 8. In certain embodiments, the combining occurs in a reaction mixture having a pH of about, at least about, or at most about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0 in aqueous buffer, or any range derivable therein, such as from about 6 to about 8.

In certain embodiments, the N-terminal protected cysteinyl residue of the first ligation product, the second ligation product, or the third ligation product is deprotected with methoxyamine-hydrochloride, carboxymethoxylamine-hemihydrochloride, o-phenylhydroxylamine-hydrochloride, o-benzylhydroxylamine-hydrochloride, o-4-nitro-benzylhydroxylamine-hydrochloride, and hydroxylamine-hydrochloride. In certain embodiments, the deprotecting with methoxyamine-hydrochloride occurs in a reaction mixture having a pH of about, at least about, or at most about 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0 in aqueous buffer, or any range derivable therein, such as from about 3 to about 5.

Certain embodiments of the invention provide a method of convergent synthesis of a polypeptide. The following provides a non-limiting example of such an embodiment: A first $N$—$C^a$ peptide is reacted with a first $N^a$—$C$ peptide to form a first $N$—$C$ ligation product; a second $N$—$C^a$ peptide is reacted with a second $N^a$—$C$ peptide to form a second $N$—$C$ ligation product; the first $N$—$C$ ligation product is converted into a $N$—$C^a$ ligation product; the second $N$—$C$ ligation product is converted into a $N^a$—$C$ ligation product, and the $N$—$C^a$ ligation product reacts with the $N^a$—$C$ ligation product to form a third $N$—$C$ ligation product, whereby the third $N$—$C$ ligation product is a polypeptide. The terms "N" and "$N^a$" represent the N-terminal residue; "C" and "$C^a$" represent the C-terminal residue, wherein $C^a$ is more reactive C-terminal residue than C, and $N^a$ is a more reactive N-terminal residue than N.

Certain embodiments of the invention provide a method of convergent synthesis of a polypeptide using peptides whose internal residues are unprotected. In some embodiments, neither the first $N$—$C^a$ peptide, the first $N^a$—$C$ peptide, the second $N$—$C^a$ peptide, nor the second $N^a$—$C$ peptide contain any internal residues with protected side chains. In other embodiments, one or more of the first $N$—$C^a$ peptide, the first $N^a$—$C$ peptide, the second $N$—$C^a$ peptide, or the second $N^a$—$C$ peptide contain internal residues with protected side chains.

In certain embodiments, one or more of the $N$—$C$ ligation products is formed under kinetic control. In other embodiments, none of the $N$—$C$ ligation products are formed under kinetic control. In some embodiments, one or more of the $N$—$C$ ligation products is formed under thermodynamic control.

In some embodiments, "$C^a$" is more reactive than "C" because "$C^a$" has a more easily substituted C-terminal leaving group. In other embodiments, "$C^a$" is more reactive than "C", despite not having a leaving group at all. In certain embodiments of the invention, the ligation reaction used to form one or more of the $N$—$C$ ligation products is not a substitution reaction involving a leaving group, but an addition reaction, involving no leaving groups.

In some embodiments, "$N^a$" is more reactive than "N" because "$N^a$" is a deprotected cysteinyl residue and "N" is a protected cysteinyl residue. In other embodiments, one or both of "$N^a$" and "N" is not a cysteinyl residue.

In some embodiments, the reacting of (1) a first $N$—$C^a$ peptide with a first $N^a$—$C$ peptide to form a first $N$—$C$ ligation product, (2) a second $N$—$C^a$ peptide with a second $N^a$—$C$ peptide to form a second $N$—$C$ ligation product, or (3) the $N$—$C^a$ ligation product with the $N^a$—$C$ ligation product to form a third $N$—$C$ ligation product, occurs in the presence of an exogenous catalyst. In certain of these embodiments, the exogenous catalyst is thiophenol or a substituted thiophenol. In some of these embodiments, the exogenous catalyst is 4-mercaptophenyl acetic acid. In some embodiments, an exogenous catalyst is used when the ligation reaction would not occur in the absence of a catalyst. In some embodiments an exogenous catalyst can be used when the underlying ligation reaction is not under kinetic control. In some embodiments, an exogenous catalyst is used when one of the two peptides to be joined does not have a weak C-terminal thioester-based leaving group.

In certain embodiments, a polypeptide is synthesized from three peptides, wherein the side chains of the internal residues of each of the three peptides is unprotected. In some embodiments, the synthesis occurs using one or more kinetically controlled native-chemical ligation reactions. In some embodiments the sequential synthesis proceeds in the N to C direction along the peptide backbone. In other embodiments, the sequential synthesis proceeds in the C to N direction.

The following method provides a non-limiting example: First, three peptides are obtained: (1) a first C-activated peptide, having an N-terminal-protected cysteinyl residue and a good C-terminal thioester-based leaving group, (2) a first N-deprotected peptide, having an N-terminal unprotected cysteinyl residue and a weak C-terminal thioester-based leaving group, and (3) a second C-activated peptide, having an N-terminal-protected cysteinyl residue or an N-terminal non-cysteinyl residue and a good C-terminal thioester-based leaving group, wherein the good C-terminal thioester-based leaving groups are the same or different. Second, the first C-activated peptide is combined with the first N-deprotected peptide to form a first ligation product having an amide bond between the α-carbon of the C-terminal residue of the first C-activated peptide and the α-carbon of the N-terminal of the first N-deprotected peptide. Third, the N-terminal-protected cysteinyl residue of the first ligation product is deprotected to form an N-deprotected ligation product. Fourth, the second C-activated peptide is combined with the N-deprotected ligation product to form a second ligation product having an amide bond between the α-carbon of the C-terminal residue of the second C-activated peptide and the α-carbon of the N-terminal of the N-deprotected ligation product, whereby the second ligation product is a polypeptide. In certain embodiments, the side chains of the internal residues of the first C-activated peptide, the first N-deprotected peptide, and the second C-activated peptide are unprotected. In other embodiments, only the side chains of the internal cysteinyl residues of one or more of the C-activated peptide, the first N-deprotected peptide, and the second C-activated peptide are protected. In certain embodiments, one or more of the peptides can be a prior ligation product. In certain embodiments, this four step synthesis of a polypeptide, may be accomplished in less than four steps or more than four steps. One, two, three, or four of the steps may occur in a one-pot reaction.

In some embodiments, the second ligation product may undergo further deprotections, replacements, ligations, derivatizations, or purifications. Furthermore, in some embodiments, the synthesized polypeptide can then be used in any additional convergent and non-convergent synthetic schemes to produce larger polypeptides and/or proteins.

The following example provides an alternative non-limiting example: First, three peptides are obtained: (1) a first C-activated peptide, having an N-terminal-protected cysteinyl residue or an N-terminal non-cysteinyl residue and a good C-terminal thioester-based leaving group, (2) a first N-deprotected peptide, having an N-terminal unprotected cysteinyl residue and a weak C-terminal thioester-based leaving group, and (3) a second N-deprotected peptide, having an N-terminal unprotected cysteinyl residue and a weak C-terminal thioester-based leaving group, wherein the weak C-terminal thioester-based leaving groups are the same or different. Second, the first C-activated peptide is combined with the first N-deprotected peptide to form a first ligation product having an amide bond between the α-carbon of the C-terminal residue of the first C-activated peptide and the α-carbon of the N-terminal of the first N-deprotected peptide. Third, the weak C-terminal thiol-based leaving group of the first ligation product is replaced with a good C-terminal thiol-based leaving group to form a C-activated ligation product. Fourth, the second N-deprotected peptide is combined with the C-activated ligation product to form a second ligation product having an amide bond between the α-carbon of the C-terminal residue of the C-activated ligation product and the α-carbon of the N-terminal of the second N-deprotected peptide, whereby the second ligation product is a polypeptide. In certain embodiments, the side chains of the internal residues of the first C-activated peptide, the first N-deprotected peptide, and the second N-deprotected peptide are unprotected. In other embodiments, only the side chains of the internal cysteinyl residues of one or more of the C-activated peptide, the first N-deprotected peptide, and the second N-deprotected peptide are protected. In certain embodiments, one or more of the peptides can be a prior ligation product. In certain embodiments, this four step synthesis of a polypeptide, may be accomplished in less than four steps or more than four steps. One, two, three, or four of the steps may occur in a one-pot reaction.

In some embodiments, the second ligation product may undergo further deprotections, replacements, ligations, derivatizations, or purifications. Furthermore, in some embodiments, the synthesized polypeptide can then be used in any in additional convergent and non-convergent synthetic schemes to produce larger polypeptides and/or proteins.

In certain embodiments of either of the examples described above, one or both of the first C-activated peptide and the second C-activated peptide is a C-activated ligation product, formed in a convergent or sequential synthesis.

In other embodiments, sequential methods of the above examples can be repeated with peptides, polypeptides, and ligation products formed in a previous application of a sequential synthesis. That is, the weak C-terminal thioester-based leaving group of the second ligation product can be replaced with a good C-terminal thioester-based leaving group, thereby forming peptide that would function a first C-activated peptide or a second C-activated peptide in a subsequent kinetically controlled convergent or non-convergent synthesis of a polypeptide.

In other embodiments, the N-terminal-protected cysteinyl residue of the second ligation product can be deprotected, thereby forming a peptide that would function as a first N-deprotected peptide or a second N-deprotected peptide in a subsequent kinetically controlled convergent or non-convergent synthesis of a polypeptide. In certain embodiments, one or both of the first N-deprotected peptide and the second N-deprotected peptide is an N-deprotected ligation product, having been formed in a prior iteration of one of the convergent or non-convergent methods of this invention.

The term "thioester-based leaving group" refers to a leaving group that has the structure —S—R, wherein "R" represents a $C_1$-$C_{10}$-alkyl, $C_2$-$C_{10}$-alkenyl, $C_2$-$C_{10}$-alkynyl, $C_6$-$C_{10}$-aryl, $C_7$-$C_{10}$-aralkyl, $C_1$-$C_{10}$-heteroaryl, $C_2$-$C_{10}$-heteroaralkyl, $C_1$-$C_{10}$-acyl, alkyl, aralkyl, aryl, or heterocyclic group.

In some embodiments, a polypeptide is selectively desulfurized by obtaining a polypeptide containing both cysteinyl residues with protected side chains and cysteinyl residues with unprotected side chains, and reacting said polypeptide with a desulfurizing agent to convert the cysteinyl residues with unprotected side chains into alanyl residues, whereby the cysteinyl residues with protected side chains are not desulfurized, and wherein the protected side chains are protected with a protection group selected from the group consisting of Acm, Tacm, and Phacm. In certain embodiments, some protected cysteinyl residues are converted into alanyl residues. For example, under certain selective desulfurization conditions, thiazolidine-protected cysteinyl residues are converted into alanyl residues. In some of these embodiments, Acm-protected cysteinyl residues are not converted into alanyl residues. In some embodiments, thiol-based leaving groups or thioester-based leaving groups are not desulfurized under selective desulfurization conditions. In certain embodiments, selective desulfurization is accomplished using Raney nickel as a catalyst.

A variety of definitions are employed herein to define a word, term, or phrase. The definition for a particular work, term, or phrase will be understood to apply to it in the context of any embodiment, unless otherwise indicated.

As used herein, the terms amino acid and amino acid residue refers to an α-amino acid and an α-amino acid residue, respectively. They may have protected or unprotected side chains. The twenty-standard amino acids and amino acid residues are referred to herein by their standard single-letter or three-letter notations. (see Voet, 1995). An amino acid sequence set forth herein, such as "DKLLM" (SEQ ID NO:5) orders the amino acid residues from the N-terminus to the C-terminus in a left-to-right manner, unless otherwise indicated from the context. As used herein, the term "side chain" refers to the substituent at the α-carbon atom of an amino acid.

The terms "peptide" or "polypeptide" as used herein refers to a compound made up of a single unbranched chain of amino acid residues linked by peptide bonds. Because the invention concerns methods of synthesizing longer lengths of amino acid residues by joining shorter lengths, the term "peptide" in the context of synthesis generally refers to a fragment that is joined to be part of the ultimate end-product, while the end product of the synthesis is generally referred to as a "polypeptide" or "protein." Peptides or polypeptides may be modified or unmodified at their C-terminals or N-terminals. Unmodified peptides or polypeptides contain unmodified amino acid residues at the C and N terminals. Modified peptides or polypeptides contain modified C- or N-terminal amino acid residues. A modified N-terminal or C-terminal amino acid residue has a protecting group or an activating group attached to its backbone or side chain. The number of amino acid residues in such compounds varies widely; however, peptides referred to herein have from 4 to 600 amino acid residues. Polypeptides referred to herein have from 8 up to 800 or more amino acid residues.

The term "leaving group," as used herein, refers to chemical groups attached to the carbonyl group of the C-terminal amino acid residue of a peptide or polypeptide by means a heteroatom, which is capable of being displaced under the mild aqueous conditions described in this patent. This term includes groups which form α-thiocarboxylic acids (α-COSH) and α-thioesters (α-COSR) (where R represents alkyl, aryl, aralkyl, or heterocyclic groups) when covalently bonded to the carbonyl group of the C-terminus. The term does not include groups which are not displaced under the mild aqueous conditions described in this patent. For example, this term does not include hydroxyl, alkoxyl, and amino groups.

The term "protein," as used herein, may be used synonymously with the term "polypeptide" or may refer to, in addition, a complex of two or more polypeptides that may be linked by bonds other than peptide bonds, for example, such polypeptides making up the protein may be linked by disulfide bonds. The term "protein" may also include a family of polypeptides having identical amino acid sequences but different post-translational modifications, such as phosphorylations, acylations, glycosylations, and the like, particularly as may be added when such proteins are expressed in eukaryotic hosts.

As used herein except where otherwise defined, the term "heteroatom" refers to an atom selected from O, N, S and P.

As used herein except where otherwise defined, the term "heterocyclic group" refers to an optionally substituted, aromatic or non-aromatic hydrocarbon ring of 4, 5, 6, 7, 8, 9, 10, 11, 12, 13, 14, 15, 16 17, 18, 19, or 20 (4-20), more preferably 5-10 carbon atoms and 1 to 4 heteroatoms. As used herein except where otherwise defined, the term "heteroaromatic" refers to an optionally substituted, aromatic hydrocarbon ring of 4, 5, 6, 7, 8, 9, 10, 11, 12, 13, 14, 15, 16 17, 18, 19, or 20 (4-20), more preferably 5-10 carbon atoms and 1 to 4 heteroatoms. A heterocyclic or heteroaromatic group may be substituted with 0-3 substituents selected from groups including, but not limited to, halo—(especially mono and poly (including di- and tri-) chloro, bromo and fluoro), cyano, nitro, carbonyl, carboxy, carboxyester, carboxyamide, amidocarboxy, amidocarbonyl, sulfoxy, sulfone and quaternary ammonium salts, alkyl alkenyl methoxy, thiol, hydroxyl, amino, alkylamino, methylthio, alkylthio, aryl, heterocyclic, aralkyl as comprising 1 to 8 alkyl aliphatic atoms attached to an aryl group (such as benzyl) or alkyl groups from 1 to 3 carbon atoms bearing any of the above moieties.

As used herein except where otherwise defined, the term "alkyl" refers to a branched or unbranched, optionally substituted, saturated or unsaturated (i.e. including alkenyl and alkynyl) hydrocarbon chain of, of at least, or of at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 carbon atoms, or any range derivable therein, including, such as 1-100, 1-20, 1-6, 1-3 or 1 carbon atom(s). An alkyl group may be substituted with 0-3 substituents selected from groups including, but not limited to, halo—(especially mono and poly (including di- and tri-) chloro, bromo and fluoro), cyano, nitro, carbonyl, carboxy, carboxyester, carboxyamide, amidocarboxy, amidocarbonyl, sulfoxy, sulfone and quaternary ammonium salts, alkenyl, methoxy, thiol, hydroxyl, amino, alkylamino, methylthio, alkylthio, aryl, heterocyclic, heteroaromatics with 1 to 4 heteroatoms, aralkyl as comprising 1 to 8 alkyl aliphatic atoms attached to an aryl group (such as benzyl) or aryl groups bearing any of the above moieties. It will be appreciated that as used herein the term "alkyl" includes, as the context requires, reference to either or both monovalent alkyl groups and divalent alkyl or alkylene groups As used herein except where otherwise defined, the term "aryl" refers to an optionally substituted, aromatic hydrocarbon ring of 5-60, preferably 5-20, more preferably 5-10 carbon atoms. Preferred aryl groups include phenyl and naphthyl groups. An aryl group may be substituted with 0-3 substituents selected from groups including, but not limited to, halo—(especially mono and poly (including di- and tri-) chloro, bromo and fluoro), cyano, nitro, carbonyl, carboxy, carboxyester, carboxyamide, amidocarboxy, amidocarbonyl, sulfoxy, sulfone and quaternary ammonium salts, alkenyl, alkoxy, thiol, hydroxyl, amino, alkylamino, methylthio, alkylthio, aryl, heterocyclic, heteroaromatics with 1 to 4 heteroatoms, aralkyl as comprising 1 to 8 alkyl aliphatic atoms attached to an aryl group (such as benzyl) or alkyl groups from 1 to 10 carbon atoms bearing any of the above moieties. It will be appreciated that as used herein the term "aryl" includes as the context requires reference to either or both monovalent aryl groups and divalent aryl or arylene groups.

As used herein except where otherwise defined, the term "aralkyl" refers to a group in which an aryl group is linked to an alkyl group and may be linked to the rest of a molecule via either the aryl or alkyl group. The term includes a benzyl group.

Any embodiment discussed with respect to one aspect of the invention applies to other aspects of the invention as well.

The embodiments in the Example section are understood to be embodiments of the invention that are applicable to all aspects of the invention.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Figure 1:
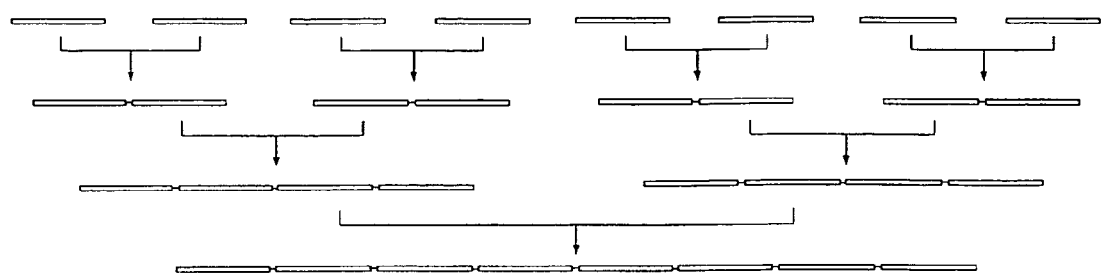
FIG. 1. Convergent chemical synthesis of a protein molecule. Each bar represents a peptide segment. A convergent strategy makes more efficient use of both the peptide building blocks and the intermediate products, and gives products of higher purity. Convergent chemical ligation is essential for the practical synthesis of large proteins and glycoproteins.

A shows the kinetically-controlled ligation of [Thz$^4$-Ala$^{15}$]-$^\alpha$thiophenylester (SEQ ID NO: 2) and [Cys$^{16}$-Leu$^{25}$]-$^\alpha$ thioester (SEQ ID NO:9), followed by conversion of the [Thz$^4$-Leu$^{25}$]-$^\alpha$thioester peptide (SEQ ID NO:8) to the [Cys$^4$-Leu$^{25}$]-$^\alpha$thioester peptide (SEQ ID NO:8). A(1) shows time zero point. The ligation gave almost exclusively the [Thz$^4$-Leu$^{25}$]-$^\alpha$thioester (SEQ ID NO:8), and the reaction was completed in one hour (A(2)). Observed mass of the product peak (2529.8±0.4 Da) was consistent with calculated mass (2530.0 Da). Arrow (i) indicates the byproduct cyclized [Cys$^{16}$-Leu$^{25}$]-$^\alpha$thioester (cyclic-[Cys$^{16}$-Leu$^{25}$], observed mass=1137.7±0.6 Da. calculated mass=1138.3 Da.). Arrow (ii) indicates the byproduct [Thz$^4$-Leu$^{25}$]-[Cys$^{16}$-Leu$^{25}$]$^\alpha$ thioester (SEQ ID NO:4) (observed mass=3567.6±0.9 Da. calculated mass=3568.2 Da.) (A(3)), Quantitative conversion of [Thz$^4$-Leu$^{25}$]-$^\alpha$thioester (SEQ ID NO:8) to [Cys$^4$-Leu$^{25}$]-$^\alpha$ thioester (SEQ ID NO:8) was carried out without affecting the thioester moiety, using 0.2M methoxyamine•HCl added directly to the ligation reaction mixture (compare A(2) with A(3)). The reaction was completed in two hours. The desired [Cys$^4$-Leu$^{25}$]-$^\alpha$thioester (SEQ ID NO:8) (Observed mass of 2517.8±0.3 Da, calculated mass=2518.0 Da) was purified for use in ligation #2.

B shows the crude ligation product from ligation #2, i.e. reaction of [Thr$^1$-Cys$^3$]-$^\alpha$thiophenylester and [Cys$^4$-Leu$^{25}$]-$^\alpha$ thioester (SEQ ID NO:8). The ligation product formed a peptide-$^\alpha$thiolactone from the transthioesterification with an internal cysteine residue. Addition of 200 mM MES-Na into the reaction mixture converted the peptide-$^\alpha$thiolactone to the peptide-$^\alpha$thioester shown, [Thz$^1$-Leu$^{25}$]-$^\alpha$thio(ethanesulfonate)ester (SEQ ID NO:31), (Observed mass=2746±1.0 Da.; calculated mass=2746.9 Da.).

C shows the crude products from the ligation #3 obtained from the reaction of [Thz$^{26}$-Gly$^{31}$]-$^\alpha$thiophenylester (SEQ ID NO:27) and [Cys$^{32}$-Thr$^{39}$]-$^\alpha$thioester (SEQ ID NO:28), (Observed mass=1596.5±1.0 Da.; calculated mass 1596.6 Da.) (SEQ ID NO:41). Note that these kinetically-controlled native chemical ligation reactions (A(2), B, and C) were performed at normal concentrations (2 mM for each peptide).

D shows the final step of the synthesis, the native chemical ligation of [Thr$^1$-Leu$^{25}$]-$^\alpha$-thioester (SEQ ID NO:31) and [Cys$^{26}$-Asn$^{46}$] (SEQ ID NO:32). D(1) shows the starting point (i.e. before the addition of thiophenol). Overnight reaction under standard native chemical ligation condition gave the full-length crambin polypeptide. D(2) shows the total crude products from folding and disulfide formation of the unpurified full-length polypeptide ligation product by dilution to 1M guanidinium•HCl and in the presence of 8 mM Cys and 1 mM cysteine. In one hour, the folded crambin molecule was formed in near quantitative yield. D(3) shows the folded crambin molecule after purification by preparative HPLC (observed mass=4702.0±0.8 Da. calculated mass=4702.4 Da.). Reverse phase HPLC analyses were performed on a Vydac $C_4$ column using a linear gradient (1-61%) of buffer B in buffer A over 15 min (buffer A=0.1% TFA in water; buffer B=0.08% TFA in acetonitrile).

Figure 8:
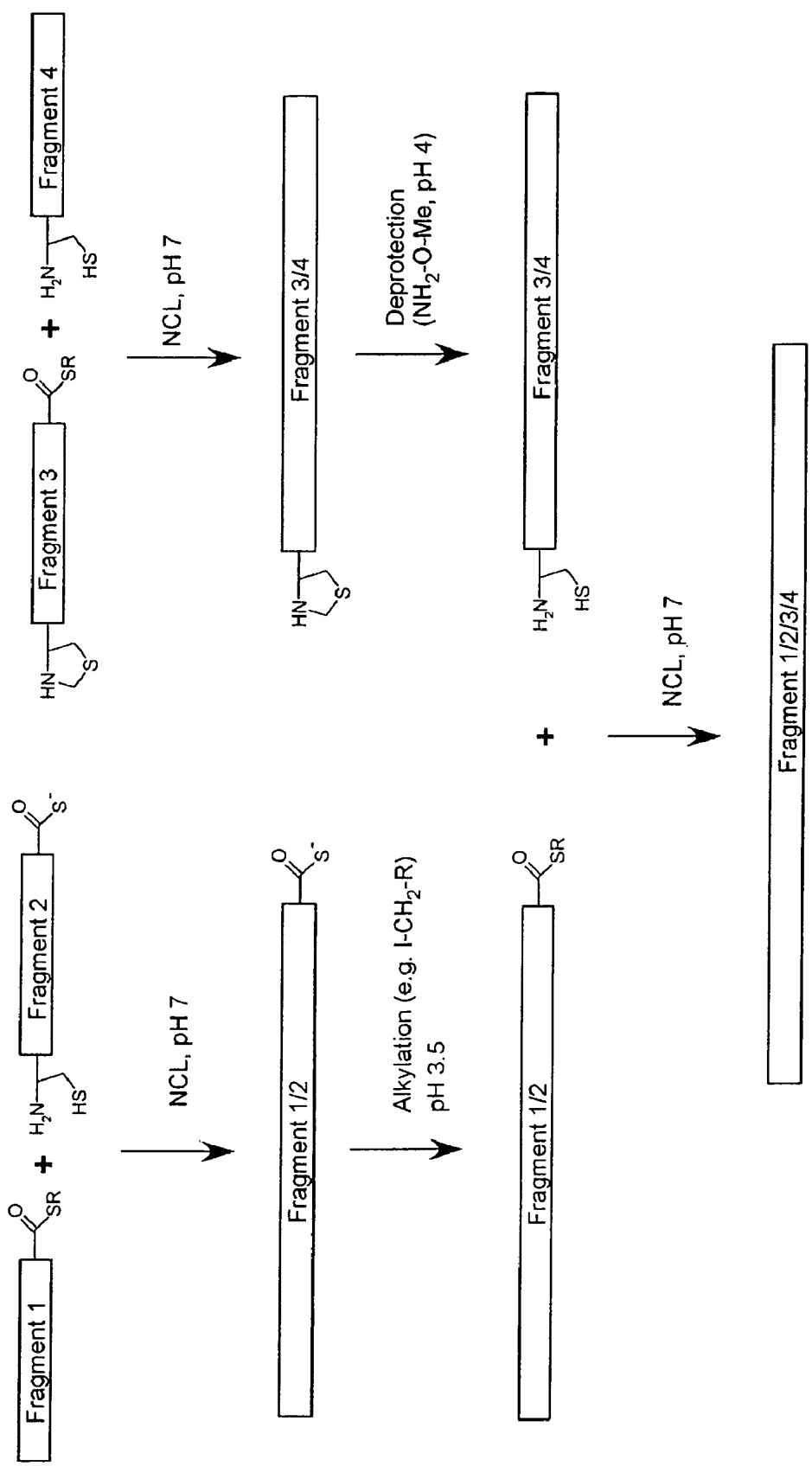

FIG. 8. Convergent assembly of Hen egg-white lysozyme from 4 polypeptide segments (each about 30 amino acids).

FIG. 9A-D. Conversion of fragment 2 thioester into a thioacid. A. HPLC chromatogram of starting material. B. Esi-MS spectrum of the starting material thioester. C. HPLC chromatogram of crude product. D. Esi-MS spectrum of product.

FIG. 10A-C. Ligation of fragment 1-thioester with fragment 2. A. HPLC chromatogram of the ligation mixture after 22 h. The asterisk indicates the desired product. B. ESI-MS of the desired product (Fragment 1/2-thioacid). C. ESI-MS of the product following alkylation with iodoacetic acid to give fragment 1/2-thioester.

FIG. 11A-B. Ligation of fragment 1/2-thioester with fragment 3/4. A. HPLC chromatogram of the ligation mixture after 30 h. The asterisk indicates the desired full-length lysozyme polypeptide. B. ESI-MS of the ligation product.

Figure 12:
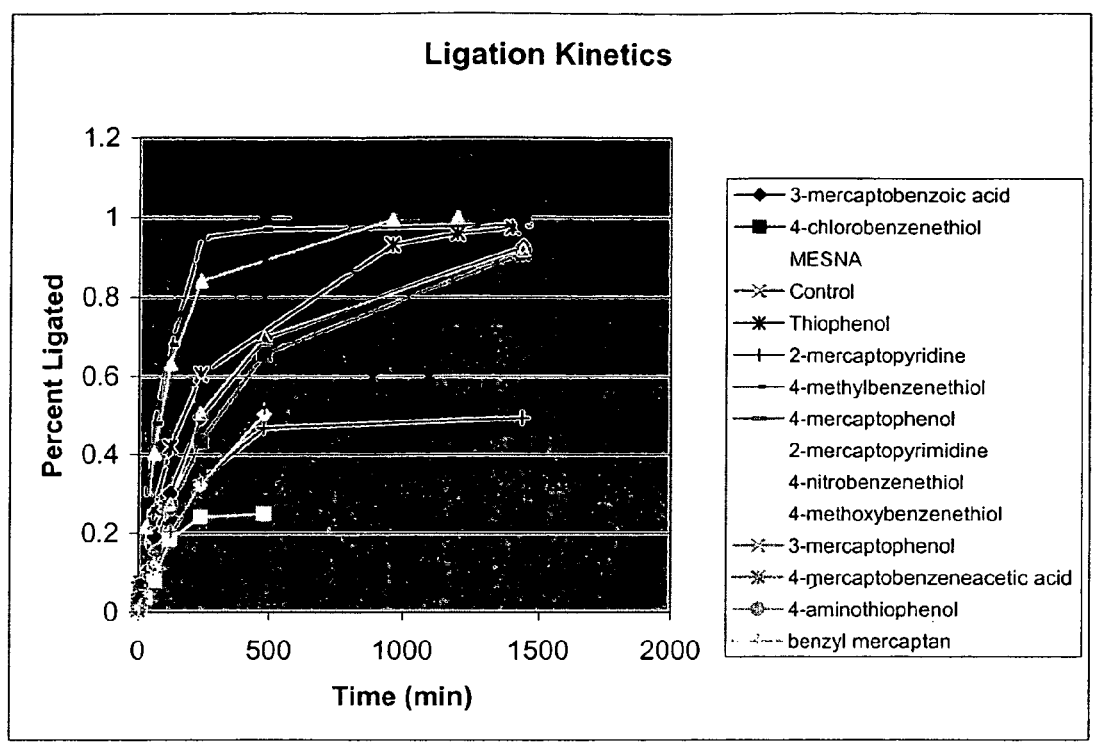

FIG. 12. Rate of ligation using various thiol catalysts

Figure 13:
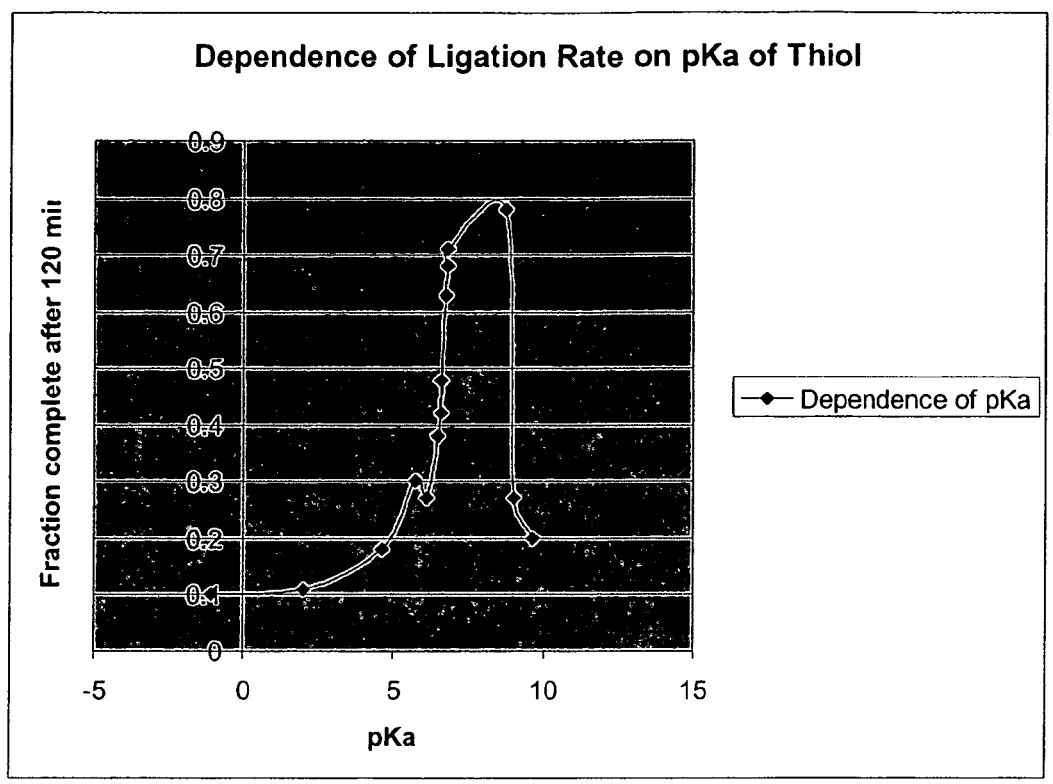

FIG. 13. Dependence of ligation rate on pKa of thiol catalyst.

Figure 14:
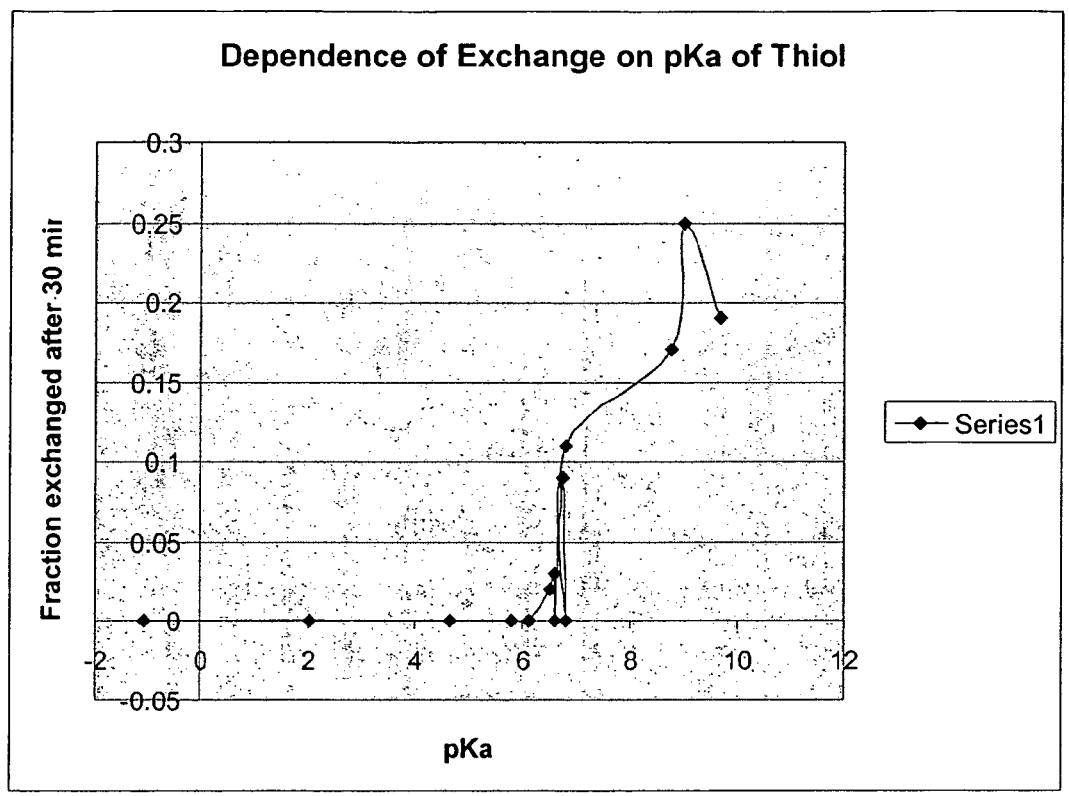

FIG. 14. Dependence of exchange rate on pKa of thiol catalyst.

Figure 15:
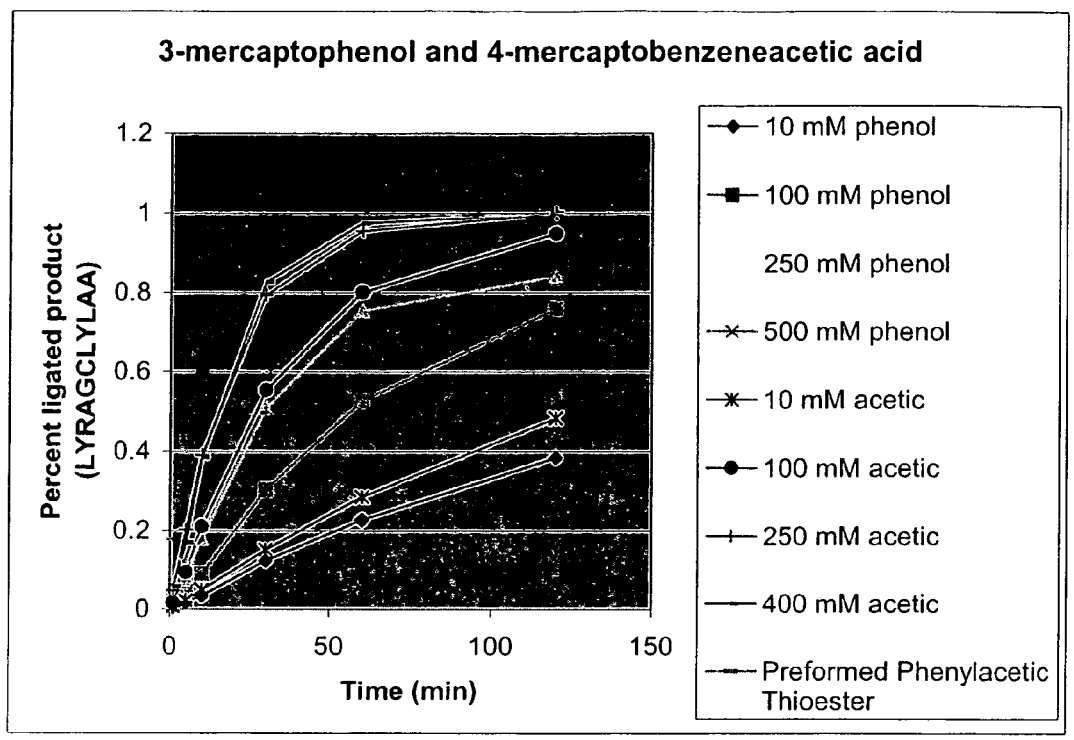

FIG. 15. Concentration dependence on ligation rates of two water-soluble thiols.

Figure 16:
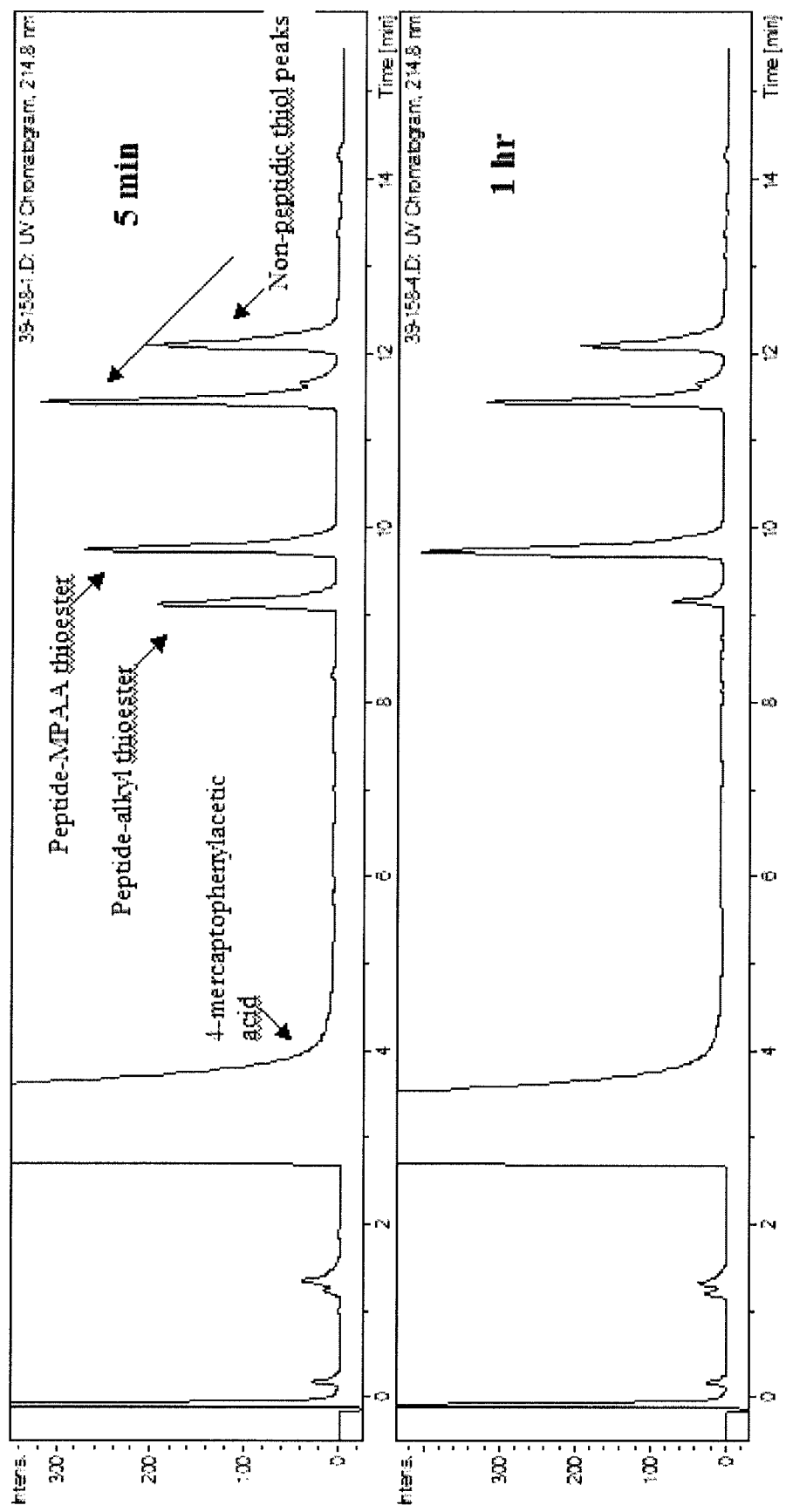

FIG. 16. Thiol-thioester exchange kinetics using 4-mercaptophenylacetic acid. Peptide alkyl thioester (6.3 mM) was incubated with 250 mM 4-mercaptophenylacetic acid for 1 hour, and the extent of exchange determined by RP-HPLC (gradient of 5-45% B over 10 minutes where A: H2O/0.1% TFA and B: ACN+0.08% TFA on a 2.1/50 mm C18 column).

Figure 17:
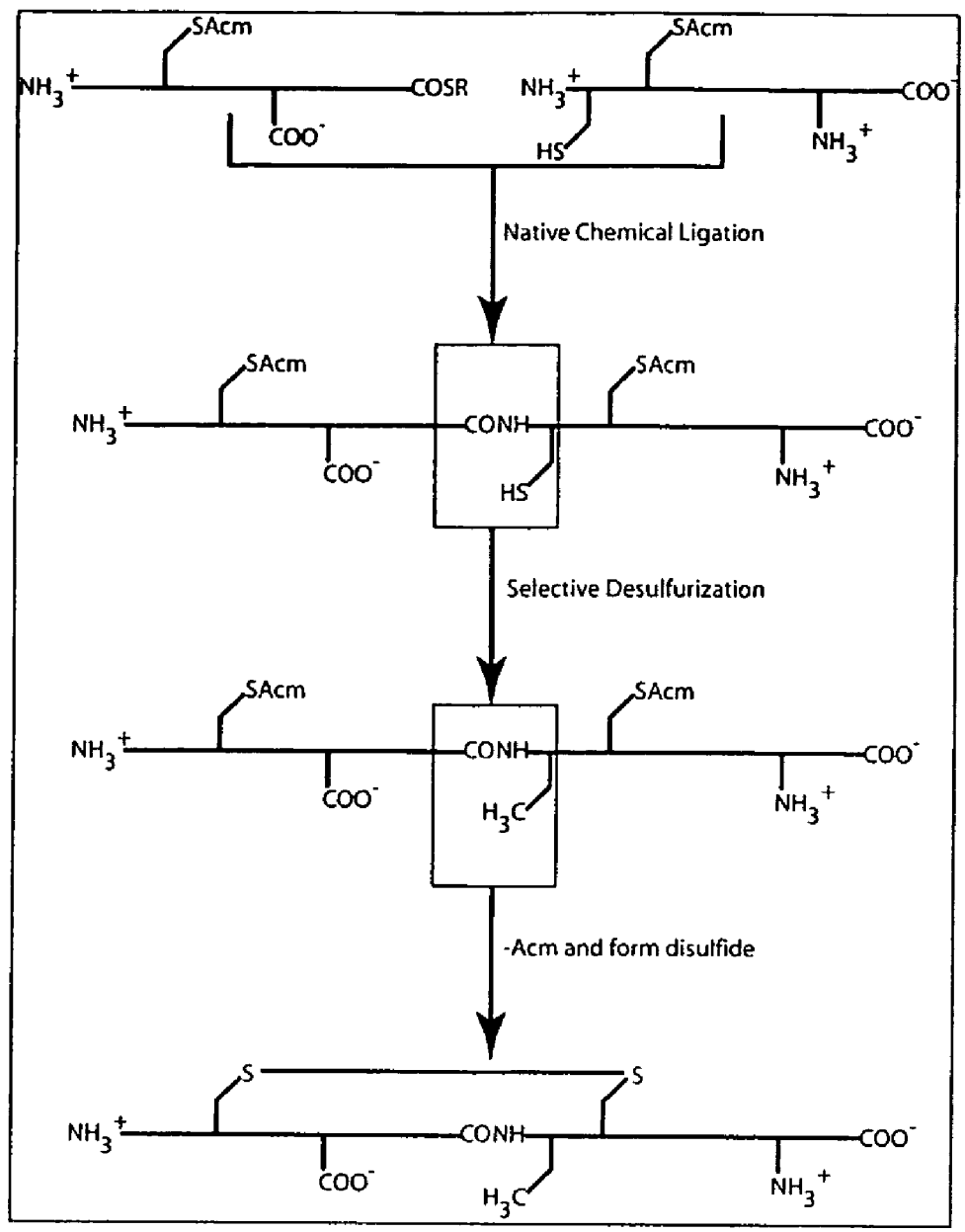

FIG. 17. General synthetic strategy for Cys-containing targets using native chemical ligation combined with selective desulfurization.

Figure 18:
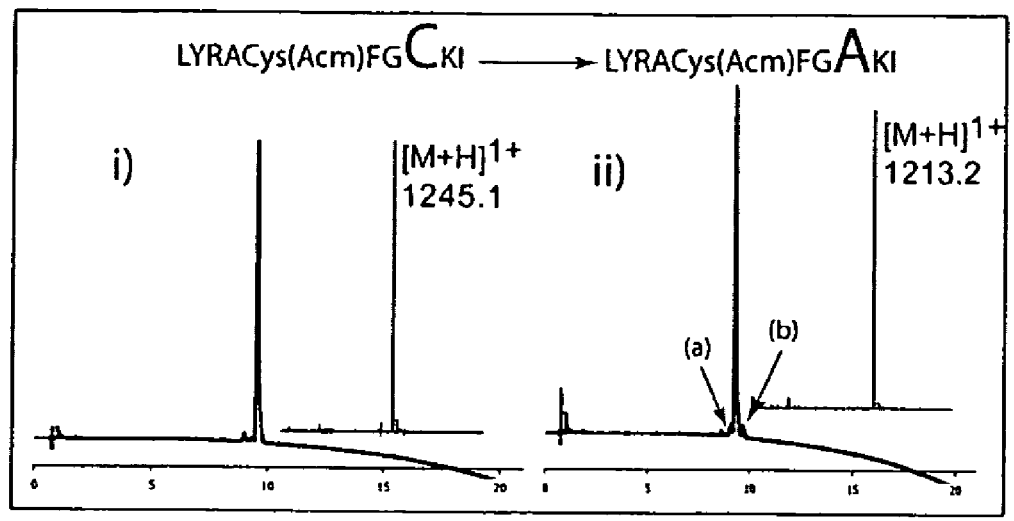

FIG. 18. Model study for the selective desulfurization of Cys to Ala in the presence of Cys(Acm) (SEQ ID NOS:13 and 40). The reaction was monitored by RP-HPLC at 214 nm with on-line LCMS. The chromatographic separations were carried out on a Vydac $C_4$ 2.1X150 mm column using a linear gradient of 5-65% buffer B over 15 mm (buffer A=0.1% TFA in $H_2O$; buffer B 0.08% TFA in acetonitrile). The peak labelled (a) is desulfurized Cys(Acm) and (b) is starting material. The calculated (using average isotopes) and observed masses for each step were: i) observed (ob)=1244.1±0.5 Da, calculated (ca)=1244.4 Da; ii) ob=1212.2±0.5 Da, ca=1212.4 Da.

Figure 19:
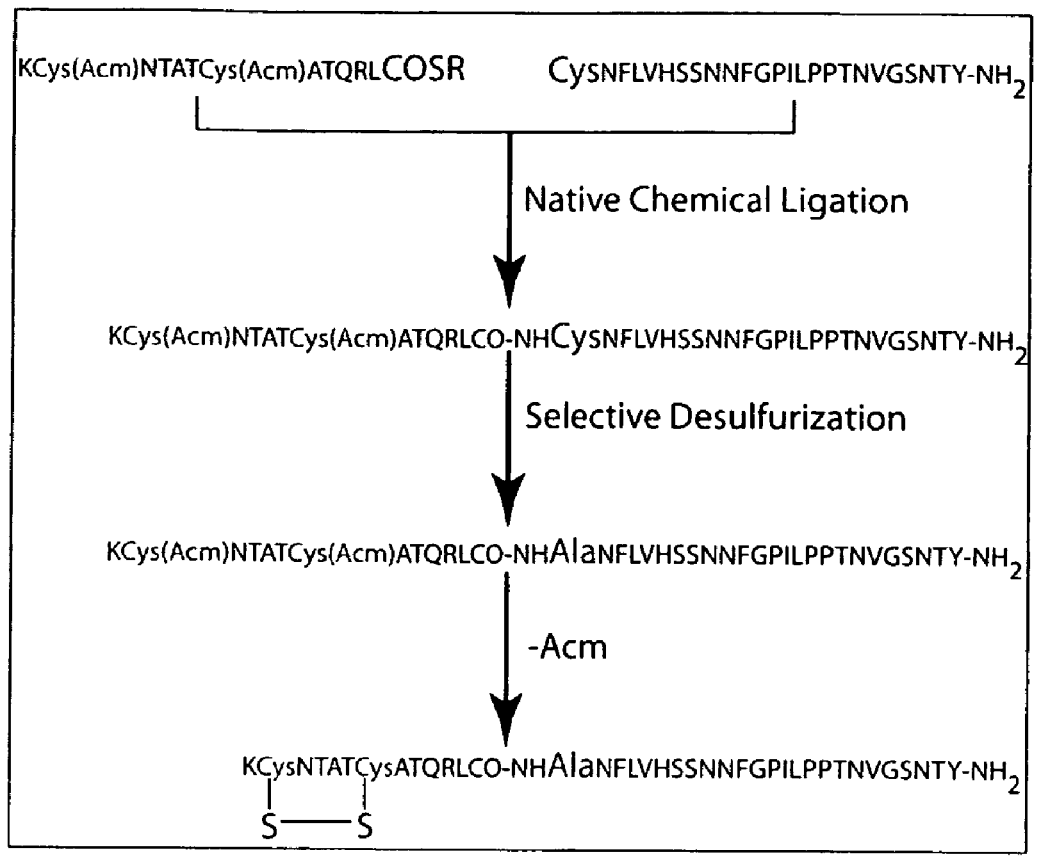

FIG. 19. Synthetic strategy used for the synthesis of [A24P, S27P, S28P]amylin. The sequences from top left to bottom right are SEQ ID NOS:16, 17, 14, 15 and 15, respectively.

FIGS. 20A-B. Ligation data for the synthesis of amylin. A(i) shows t=0 h for the ligation reaction (SEQ ID NO:38 and SEQ ID NO:39), A(ii) shows t=8 h reaction complete. The calculated (using average isotopes) and observed masses for each step were: A(ii) ob=4125.9±0.5 Da, ca=4125.3 Da (SEQ ID NO:14). Data for the selective desulfurization of amylin: B(i) shows t=0 for the desulfurization reaction (SEQ ID NO:14); B(ii) shows t=6 h for the desulfurization product (SEQ ID NO:15), showing complete reduction (peak (a) is a column contaminant from a previous analysis). The calculated (using average isotopes) and observed masses for each step were: B(i) ob=4125.9±0.5 Da, ca=4125.3 Da; B(ii) ob=4093.8±5 Da ca=4093.3 Da.

Figure 21:
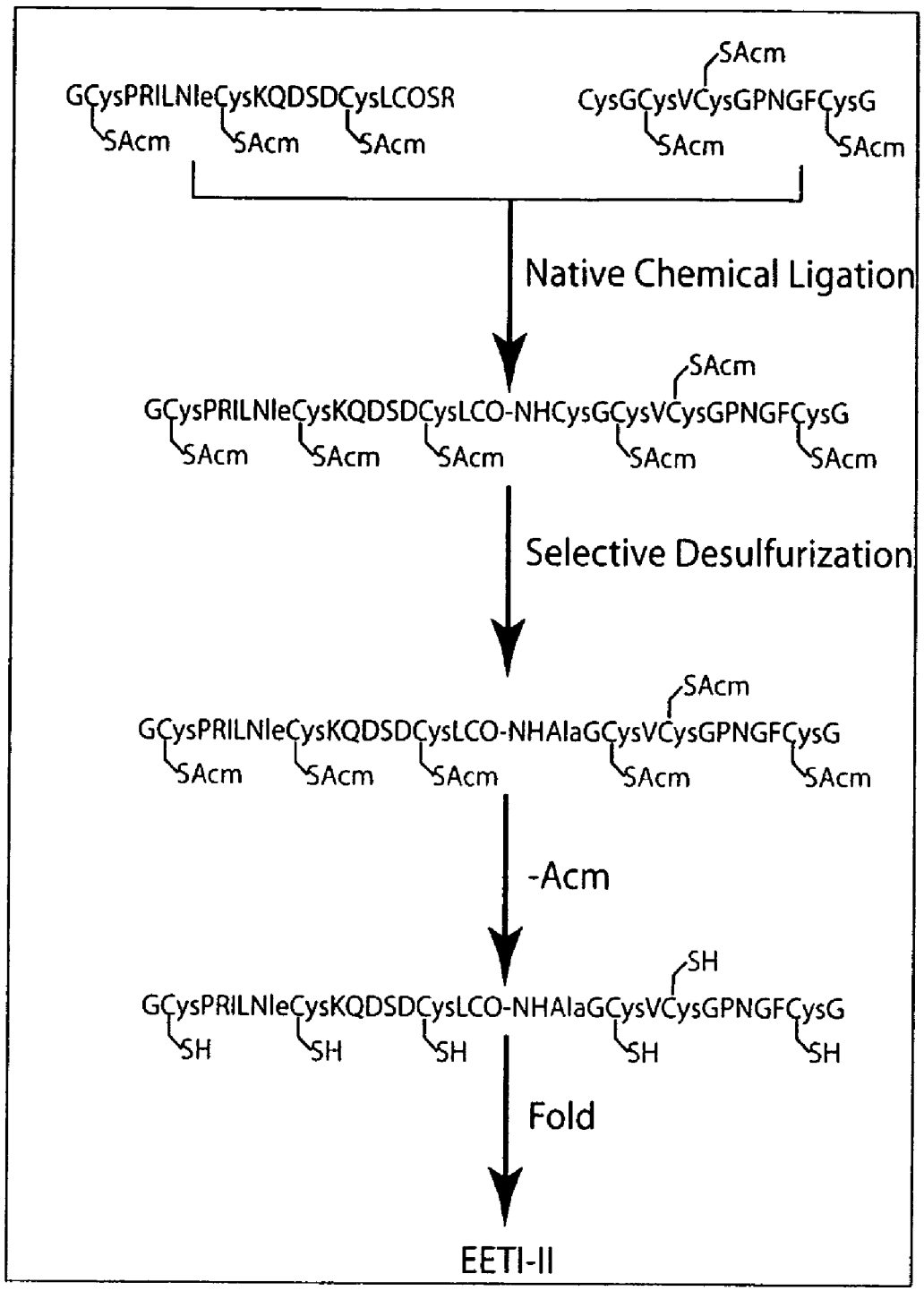

FIG. 21. Synthetic Strategy used for the total synthesis of Met7Nle EETI-II[1-28] (SEQ ID NO:18). Note: there is an arginine residue missing between each Nle-Cys pair shown in the figure. The corrected sequences are from top left (SEQ ID NO:19) to top right (SEQ ID NO:20); and through to the bottom (SEQ ID NO: 37 and SEQ ID NO:18 (twice)).

FIGS. 22A-B. Ligation data for the synthesis Met7Nle EETI-II[1-28]. A(i) shows t=0 h for the ligation reaction (SEQ ID NO:20 and SEQ ID NO:19), A(ii) shows t=8 h reaction complete (SEQ ID NO:37). The calculated (using average isotopes) and observed masses for A(ii) were ob=3344.5±0.4 Da, ca=3344.4 Da. Data for the selective desulfurization of amylin: B(i) shows t=0 for the desulfurization reaction (SEQ ID NO:37), B(ii) shows t=6 h 30 mm for the desulfurization reaction (SEQ ID NO:18). (a) is loss of Acm and (b) is starting material. The calculated (using average isotopes) and observed masses for each step were: B(i) ob=3344.5±0.4 Da, ca=3344.4 Da; B(ii) ob=3312.6±0.4 Da ca=3312.4 Da.

DESCRIPTION OF ILLUSTRATIVE EMBODIMENTS

The present invention concerns a versatile synthesis method for polypeptides based on improved yields as a result of kinetically controlled ligation of fragments of the desired polypeptide. It is particularly attractive because it also can involve a native chemical ligation. A "native chemical ligation" is the chemoselective reaction of unprotected or N-terminal cysteine protected peptide segments with another unprotected peptide segment resulting in the formation of a ligated peptide with an amide bond at the ligation site.

A convergent strategy for the chemical synthesis of a protein molecule is shown in FIG. 1. Synthesis of a ~300 residue protein will optimally use ~8 peptide segments of ~35-40 residues each. In a convergent approach, the two halves of the target polypeptide are prepared separately and reacted to give the desired full-length product. A convergent approach gives an exponential increase in yield compared to the sequential assembly of a set of peptides. For a set of eight peptide building blocks, sequential assembly would involve seven consecutive reactions and, with a recovered yield of 70% per step, would give an overall yield of approximately 8% (i.e., $(0.7)^7$); by contrast, a fully convergent strategy (FIG. 1) with the same yield per step would give an overall yield of approximately 34% (i.e., $(0.7)^3$)—more than a four-fold increase in yield! A convergent approach to the synthesis of proteins has other advantages including the preparation of more homogeneous protein constructs and substantial timesavings.

Because of its versatility and the potential for improved yields, convergent synthesis is an important current methodology challenge for the synthesis of large proteins (Casi and Hilvert; Schnolzer and Kent, 1992; Canne et al., 1995; Nilsson et al., 2005) and glycoproteins (Nilsson et al., 2005; Davis, 2002; Warren et al., 2004). The objective is the routine chemical synthesis of proteins using modern native ligation methods in conjunction with a convergent strategy.

I. SYNTHESIS REACTIONS AND PRODUCTS

The present invention concerns a number of different chemical reactions including, but not limited to: preparation of a peptide thiophenyl ester; preparation of a peptide with a protected chemical group on the residue at the amino terminus; deprotection of the same peptide; preparation of a peptide that no longer has a thiophenyl ester; and kinetically controlled ligation of two peptides having different chemical groups on the residues at their terminal ends.

The inventors have described certain of these reactions, chemical groups, and concepts, as well as other embodiments previously, but not with respect to implementing a fully convergent synthesis. See U.S. Pat. Nos. 6,642,357; 6,476,190; 6,326,468; 6,307,018; 6,184,344; 5,854,389; 5,186,898; 4,816,513; 4,668,476, all of which are hereby incorporated by reference.

The direct on-resin synthesis of peptide-$\alpha$thioesters for use in native chemical ligation is discussed in Bang et al. (2006), which is hereby incorporated by reference.

A. Creation of More Reactive Upstream Peptides

The present invention concerns methods in which two peptides involved in a ligation reaction have different chemical groups at their C-terminal residues to provide for a kinetically controlled ligation reaction. In many embodiments of the invention, this takes place in the absence of any exogenous catalyst, such as thiophenol.

With native chemical ligation, until the present invention, relatively unreactive peptide-$SCH_2CH_2CO$-Leu (i.e., alkyl) thioesters were routinely prepared as described by Dawson (Hackeng et al., 1999). Typically, native chemical ligation of the peptide-thioester and Cys-peptide has been carried out in the presence of thiophenol as a catalyst (Dawson et al., 1997); the reactive species is assumed to be the peptide-thiophenylester.

The present invention concerns in some embodiments a preformed peptide thiophenylester. There are a variety of ways to achieve this peptide. This peptide may or may not already have a protected N-terminal amino acid residue.

For instance, a lyophilized peptide-$\alpha$thioester after HF cleavage may be used for the exchange reaction. Generally, the crude peptide may be dissolved in an aqueous buffer containing guanidine hydrochloride and thiophenol. The concentration of the guanidine hydrochloride may be about, at least about, or at most about 4, 5, 6, 7, or 8 M, or any range derivable therein. The concentration of the thiophenol may be about, at least about, or at most about 0.05, 0.1, 0.15, 0.2, 0.25, 0.3, 0.35, 0.4, 0.45, 0.5% (vol/vol) or more, or any range derivable therein.

In some embodiments, the crude peptide may be dissolved in pH 6.8 aqueous buffer containing 6 M guanidine hydrochloride and 0.2% thiophenol (vol/vol). Peptide concentration in the solution may be ca. 0.2 mM. The reaction mixture should be vigorously stirred for 12 hours with exclusion of air, and analyzed by LC-MS. After the conversion, the reaction can be quenched (acidified to pH 3) by the addition of aqueous 6N HCl.

Residual thiophenol and oxidized thiophenol (diphenyl disulfide) can be removed by extraction with diethyl ether. Acid quenching is necessary before the diethyl ether extraction procedure in order to prevent transthioesterification with residual $HSCH_2CH_2CO$-Leu that cannot be extracted.

One can start by creating a peptide-thioester, such as described in U.S. Pat. No. 6,184,344, which is hereby incorporated by reference. That patent eliminates the need for an elaborate protecting group strategy since the oligopeptide-thioester moiety is derived from a precursor thioacid. This precursor thioacid (peptide-$\alpha$-COSH) is synthesized by a standard stepwise solid-phase peptide synthesis on an aminomethyl resin support, equipped with a thioester resin linker. The precursor thioacid is cleaved from the linker/resin almost quantitatively (99%) in liquid HF at 0° C. for 1 hour. The thioester peptide (peptide-α-COSR) can be synthesized in two general ways: (1) Reaction of a crude lyophilized thioacid peptide (peptide-α-COSH) with Ellman's reagent (5,5'-dithiobis-2-nitrobenzoic acid, available from Aldrich company) at pH 5.5 (2.0 equivalents), 6M Guanidine in 100 mM Na acetate buffer. This gives the SNB-thioester peptide (peptide-α-COSNB), which is subsequently purified by reversed phase high performance liquid chromatography (RPHPLC). (2) Reaction of a crude lyophilized thioacid peptide (peptide-α-COSH) with benzyl bromide at pH 4.0, 6M guanidine and 100 mM Na acetate buffer. The benzyl thioester (peptide-α-COSBn) is then purified by RPHPLC. The conditions stated above, permit the formation of an unprotected peptide that is equipped with the activated thioester.

Subsequently, the peptide-thiophenylester can be obtained by treating a ca. 0.2 mM solution of crude synthetic peptide-thioester with 0.2% thiophenol (vol/vol) in pH 6.8 aqueous buffer containing 6 M guanidinium hydrochloride for 12 hours at room temperature. The converted peptide-thiophenylester can be purified by use of preparative HPLC. Detailed procedures for the quantitative conversion of a peptide-thioester to a peptide-thiophenylester and the purification are described below.

In other embodiments, a thioacid represents a reversible protecting group for thioesters that may be used in convergent protein synthesis. Therefore, in certain embodiments, an α-thiocarboxylic acid (α-COSH) is contemplated for use in the invention as the reacting or leaving group on an upstream peptide.

B. Protected N-Terminal Chemical Group

A variety of ways to protect the N-terminal residue, including a cysteyl residue, are known to those of skill in the art. A protected residue refers to a residue with a chemical moiety capable of protecting a functional group from reacting with another functional group, and removable without damage to the formed amino acid or peptide.

For example, peptides may be prepared manually by "in situ neutralization" Boc chemistry stepwise solid phase peptide synthesis (Dawson and Kent, 2000). In certain embodiments, this may involve —OCH$_2$-Pam-resins (free $^\alpha$carboxyl peptides) or HSCH$_2$CH$_2$CO-Leu-OCH$_2$-Pam-resin (thioester peptides) (Kochendoerfer et al., 2003). Side-chain protection for amino acids was as follows: Arg(Tos), Asn (Xan), Asp(OcHex), Cys(4-CH3Bzl), Glu(OcHex), Lys(2-Cl—Z), Ser(Bzl), Thr(Bzl), Tyr(Br—Z).

The 1,3-thiazolidine-4-carboxo (Thz) group may be introduced to protect the N-terminal Cys of the middle peptide segments, and Boc-L-thiazolidine-4-carboxylic acid may be used for peptide synthesis.

After chain assembly is complete, peptides may be deprotected and simultaneously cleaved from the resin support by treatment with anhydrous HF containing p-cresol (90:10, vol/vol) for 1 h at 0° C. After evaporation of the HF under reduced pressure, crude products may be precipitated and triturated with chilled diethyl ether, and the peptide products may be dissolved in 50% aqueous acetonitrile containing 0.1% TFA. Peptide compositions may be confirmed by LC-MS.

Any of the known protecting groups suitable for protecting the N-terminal Cys of a peptide segment can be used, provided that they are stable to ligation conditions, stable to conditions for adding the linker, and removable from the peptide segment under conditions that are not harmful to the solid-phase bound peptide, the linker, the resin, or the cleavable handle, if used. The protecting groups must also be stable to stepwise solid phase peptide synthesis conditions. An example of a protecting group is ACM (Acetamidomethyl), which provides cysteine side chain protection (—SCH2NHCOCH3), and can be cleaved with mercury(II) acetate, or other suitable reagents. Fmoc (9Fluorenylmethylcarbamate) provides alpha amino protection, can be cleaved in 20% piperidine in DMF and works well with hydrophilic peptides. DNPE (2-(2,4-dinitrophenyl)ethyl) provides cysteine side chain protection and cleaves in 50% piperidine in DMF. Para-nitrobenzenesulfonyl provides alpha-amino protection, and is cleaved in 1 M DBU/1 M beta-mercaptoethanol in DMF. Additional cysteine protecting groups include, but are not limited to, Sulfmoc, NSC, Dde, Boc-Cys(Acm)-OH, Fmoc-Cys-(Mob)-OH, Boc-Cys(Fm)-OH, and Boc-Cys(DNPE)-OH, wherein Acm=acetamidomethyl, Mob=methoxybenzyl, Dnpe=2-(2,4-dinitrophenyl)ethyl, Fm=9-fluorenylmethyl. See Green and Wuts (1991), particularly p. 293-294, 318-319; Merrifield (1978); Samukov et al. (1994); Bycroft et al. (1993); Royo et al. (1992); Miller (1997). Certain protecting groups can make peptide segments insoluble. For example, certain hydrophobic peptide segments may become insoluble upon addition of a protecting group. One of ordinary skill in the art can readily ascertain the suitability of any particular protecting group for a peptide segment.

In certain embodiments, the N-terminal residue of a downstream peptide need not be a cysteine, as discussed in U.S. Pat. No. 6,307,018 and U.S. Patent Publication 2005/0113563, which are hereby incorporated by reference. These references further discuss unmasking a protected group.

C. Conversion of a Peptide with a Protected N-terminal Chemical Group

As discussed in the previous section, a peptide with a protected N-terminal chemical group can be readily converted to an unprotected chemical group. In certain embodiments, a Thz-peptide-thioester is converted into the corresponding Cys-peptide-thioester without affecting the thioester moiety. Thioesters are susceptible to attack by amine nucleophiles such as the methoxyamine-hydrochloride used to convert the Thz to Cys (Jencks, 1987). Methoxyamine-hydrochloride at approximately pH 4 in aqueous buffer can be used to rapidly convert a Thz-peptide-thioester to a Cys-peptide-thioester, such as has been described for the conversion of a non-thioester peptide (Bang and Kent, 2004; Villain, 2001, which is hereby incorporated by reference). It is also feasible to carry out the native chemical ligation of a peptide-αthioester and a Cys-peptide in the presence of 0.2 M methoxyamine-hydrochloride at pH 7, without significant damage to the thioester moiety even over prolonged time periods (Bang and Kent, 2004).

D. Kinetically Controlled Ligation

A typical kinetically-controlled ligation (based on the nature of the thioester) may be performed in pH 6.8 with 200 mM phosphate buffer containing 6 M guanidine hydrochloride, at a concentration of 2 mM for each peptide.

Alternatively, one of the peptides can be titrated into the reaction. For example, a kinetically-controlled ligation (based on the titration of {peptide1-$^\alpha$thioester} by {Cys-peptide2-$^\alpha$thioester} can be employed. A peptide1-$^\alpha$thioester may be dissolved to a concentration of approximately 20 mM in 0.5 M Bis-Tris buffer containing 6 M guanidine hydrochloride and 1% thiophenol (vol/vol), and the reaction mixture may be stirred at room temperature. The Cys-peptide2-$^\alpha$thioester may be maintained in unbuffered aqueous 6 M guanidine hydrochloride (pH 4~5) to prevent any ligation reaction before its titration (i.e., slow addition) into the ligation mixture. This unbuffered solution of Cys-peptide 2-$^\alpha$thioester may be added slowly to the peptide1-$^\alpha$thioester solution. The titration rate may be controlled to be finished in several hours.

Native chemical ligation may be carried out under the same conditions used for the kinetically-controlled ligation, except 1% (v/v) thiophenol may be added to the reaction mixture.

Kinetically controlled ligation is further discussed in Johnson et al. (2006), which is hereby incorporated by reference. Insights into the mechanism and catalysis of native chemical ligation reactions is discussed in Johnson and Kent (2006), which is hereby incorporated by reference.

E. Converting C-Terminal End to a Carboxylate Group

In methods of the invention, a step of converting a chemical group on C-terminal residue of a ligation product into a carboxylate group is included. To do this, a base may be added to achieve the conversion.

F. Other Chemical Reactions

The current invention contemplates combining the methods and compositions of kinetically controlled ligation with other chemical tactics. For example, use of the one-pot ligation principle (Bang and Kent, 2004) will enable multiple sets of three peptide segments to be stitched together for use in convergent synthesis. The advantage rendered by a one-pot strategy is that three peptide segments can be joined prior to a purification step. A one-pot strategy is also known as a three-segment ligation strategy. This strategy involves ligating an upstream peptide, a middle peptide and a downstream peptide. In one embodiment, the downstream peptide having an N-terminal cysteyl residue is combined with the middle peptide having a protected N-terminal cysteyl residue and a C-terminal thioester group to form an initial ligation product having an amide bond between the $\alpha$-carbon of the C-terminal of the middle peptide and the $\alpha$-carbon of the N-terminal of the downstream peptide. In a subsequent step, the protected N-terminal cysteyl residue is deprotected. In certain embodiments, the deprotection can be achieved through the addition of methoxyamine-HCl to the reaction mixture at a pH around 4. In a subsequent step, the upstream peptide having a protected N-terminal cysteyl residue or a N-terminal non-cysteyl residue and a C-terminal thioester group is combined with the reaction mixture at an approximately neutral pH. In a further step, the upstream peptide reacts with the initial ligation product to form a subsequent ligation product having an amide bond between the $\alpha$-carbon of the C-terminal of the upstream peptide and the $\alpha$-carbon of the N-terminal of the initial ligation product. In a further step, the subsequent ligation product is purified using reverse phase HPLC, recrystallization, or a combination of purification strategies. It is contemplated that the subsequent ligation product may be modified, as previously described, for further use in convergent or non-convergent kinetically controlled ligation. For example, the subsequent ligation product may be modified with a better leaving group at the C-terminal to give a C-activated ligation product. Alternatively, if the subsequent ligation product has a protected N-terminal cysteyl or other protected N-terminal $\beta$- or $\gamma$-thiol amino acid residue, as described below, this protected residue can be deprotected to yield a N-activated ligation product. In certain embodiments, the ligation product, the modified ligation product, or the C-activated ligation product from a kinetically-controlled ligation can serve as either the upstream or the middle peptide in a one-pot synthesis. Likewise, the ligation product, the modified ligation product, or the N-activated ligation product from a kinetically-controlled ligation can serve as either the downstream, or the middle peptide in a one-pot synthesis.

Ligation at non-cysteyl residues facilitates convergent synthesis and protein synthesis in general. One advantage of using non-cysteyl-based ligation reactions in combination with cysteyl-based ligation methods and compositions is greater synthetic flexibility, especially when the target peptide, polypeptide, or protein doesn't contain many, any, or few conveniently spaced cysteyl residues. Furthermore, it is contemplated using non-cysteyl-based ligation methods and compositions when the peptide fragments to be joined don't have a cysteyl residue at the N-terminal of the downstream peptide.

The set of chemical methods and compositions based on kinetically-controlled ligation are compatible with the use of thiol-containing auxiliary groups (Canne et al., 1996; Low et al., 2001). In certain embodiments, this technique using thiol containing auxiliary groups is used to make peptide or polypeptide chains with native or modified backbone structures. The advantage of this method is in expanding the amino acid residues amenable to native chemical ligation, and lifting the requirements that the downstream peptide have an N-terminal cysteyl residue.

In certain embodiments, an upstream peptide having the structure [peptide$_3$]$^\alpha$COSR is combined with a downstream peptide having the structure HS-D-N$^\alpha$[peptide$_4$] to form first an initial ligation product which later rearranges to a rearranged ligation product having an amide bond between the upstream and downstream peptides and the amide having a N$^\alpha$-D-SH group. In this paragraph, D represents an alkyl or an aralkyl group and R represents an alkyl, aryl, aralkyl, or heterocyclic group. In certain embodiments, this invention contemplates that the upstream peptide also has a N-terminal protected thiol-containing auxiliary group, which may then be deprotected prior to a subsequent ligation reaction. (US 2005/0113563 A1).

In one embodiment, an upstream peptide having the structure [peptide$_1$]$^\alpha$COSR is combined with a downstream peptide having the structure HSCH$_2$CH$_2$O—N$^\alpha$[peptide$_2$] to form a rearranged ligation product having an amide bond between the upstream and downstream peptides and a secondary amide having a N$^\alpha$-oxyethanethiol group. In another example, an upstream peptide having the structure [peptide$_3$]$^\alpha$ COSR is combined with a downstream peptide having the structure HSCH$_2$CH$_2$—N$^\alpha$[peptide$_4$] to form a rearranged ligation product having an amide bond between the upstream and downstream peptides and the amide having a N$^\alpha$-ethanethiol group. In yet another example, an upstream peptide having the structure [peptide$_3$]$^\alpha$COSR is combined with a downstream peptide containing the auxiliary group 1-phenyl-2-mercaptoethyl at the N-terminal $\alpha$-amino group to form a rearranged ligation product having an amide bond between the upstream and downstream peptides and the amide having a N$^\alpha$-1-(4-methoxyphenyl)-2-mercaptoethyl group. In certain embodiments, the alkylthiol, the ethanethiol, the 1-(4-methoxyphenyl)-2-mercaptoethyl, or the oxyethanethiol group of the rearranged ligation product is removed with Zn/acid treatment to give an auxiliary-group-free-ligation product having a native backbone structure. In other embodiments, the group is removed from the rearranged ligation product with HF treatment to form the auxiliary-group-free-ligation product.

Furthermore, it is contemplated that the rearranged ligation product or the auxiliary-group-free-ligation product may be further modified, as previously described, for further use in convergent or non-convergent kinetically controlled ligation. For example, the rearranged ligation product or the auxiliary-group free-ligation product may be modified with a better leaving group at the C-terminal to give a C-activated ligation product. Alternatively, if the rearranged ligation product or the auxiliary-group free-ligation product has a protected N-terminal cysteyl or other protected N-terminal β- or γ-thiol amino acid residue, as described below, this protected residue can be deprotected to yield a N-activated ligation product. In another embodiment, the ligation product, the modified ligation product, or the C-activated ligation product from a kinetically-controlled ligation may serve as the upstream peptide in the above described method which uses thiol-containing auxiliary groups. Likewise, the ligation product, the modified ligation product, or the N-activated ligation product from a kinetically-controlled ligation may serve as the downstream peptide in the above described method which uses thiol-containing auxiliary groups. It is further contemplated that the method using thiol-containing auxiliary groups may be modified to be a kinetically-controlled ligation by using different leaving groups at the C-terminals of the peptides to be joined. In certain embodiments, the method using thiol-containing auxiliary groups is kinetically-controlled and fully convergent.

In certain embodiments, this invention contemplates combining convergent synthetic methods and compositions with sequential methods. One of the advantages of combing convergent and sequential methods is synthetic flexibility. Such an approach may be termed semi-convergent.

The invention also contemplates further steps to modify the peptide or polypeptide products to synthesize proteins, lipoproteins, or glycoproteins. In certain embodiments, the pH buffer is adjusted to promote efficient folding. In other embodiments, redox reagents are added to promote the formation of intra- or intermolecular covalent cross-linkages, for example disulfide bonds. By combining these methods and compositions, the secondary, tertiary, and quaternary structure of simple and complex polypeptides and protein is created and ordered. In addition, the formation of protein domains, the substructure produced by any part of a polypeptide chain that can fold independently in to a stable structure, can be facilitated.

In addition to facilitating the formation of the correct conformation and three-dimensional structure of the target proteins, this invention contemplates further modifying the peptide, polypeptide, or protein through the covalent or non-covalently binding of non-amino acid molecules. In certain embodiments, these non-amino acid molecules comprise one or more heme groups, rhodopsin molecules, vitamins, biotins, fatty acids, lipids, carbohydrates, polymers, or inorganic elements, ions, or clusters.

The invention combines the chemical methods and compositions based on kinetically-controlled ligation using cysteyl residues with the method of selectively desulfurizing cysteyl residues to alanyl residues for synthesizing target proteins or polypeptides containing either no cysteyl residues, few cysteyl residues, or few conveniently spaced cysteyl residues (Yan and Dawson, 2001). This combination method takes advantage of the fact that (1) alanyl residues are more abundant than cysteyl residues in most proteins and (2) cysteyl residues can be converted into alanyl residues using selective desulfurization. In one embodiment, a downstream peptide having an N-terminal cysteyl residue is combined with an upstream peptide having a protected N-terminal cysteyl residue or a N-terminal non-cysteyl residue and a C-terminal thioester group to form an initial ligation product having an amide bond between the α-carbon of the C-terminal of the upstream peptide and the α-carbon of the N-terminal of the downstream peptide. In a subsequent step, the initial ligation product is treated with hydrogen and a catalyst to convert the cysteyl residues into alanyl residues forming a subsequent ligation product. In certain embodiments the catalyst is Raney nickel. In other embodiments the catalyst is platinum, palladium, or other transitions metals. In further embodiments the catalyst is a metal alloy, or a transition metal complex. In certain embodiments, the catalyst is supported on alumina. In other embodiments the catalyst is supported on carbon. In other embodiments the support is barium sulfate. It is contemplated that hydrogenolytic desulfurization can be performed in a wide variety of solvents. In certain embodiments the solvent is aqueous acetic acid; in other embodiments the solvent is a phosphate buffer containing guanidine. The pH of the buffer can vary widely. In a certain embodiments, the pH is between 4 and 8.

It is furthermore contemplated that the selective desulfurization method can be performed on peptides or polypeptides containing protected side chains as well as unprotected side chains. In certain embodiments, the methionyl residues are protected prior to the hydrogenolytic desulfurization step. In a step subsequent to the hydrogenolytic desulfurization, the protected methionyl residues are deprotected.

The invention contemplates combining the chemical methods and compositions based on kinetically-controlled ligation with a native chemical ligation method using N-terminal β- or γ-thiol amino acid residues, other than cysteyl, followed by selective desulfurization. This combination provides the advantage of a fully or partially convergent method of protein or polypeptide synthesis with even greater sequence flexibility at the ligation sites. Not only can cysteyl residues be converted to alanyl residues, as described above, but β- or γ-thiol amino acid residues can be converted to valyl, leucyl or isoleucyl residues. Furthermore, other β- or γ-thiol amino acid residues can be converted into unnatural amino acid residues having unsubstituted alkyl side chain, e.g. an amino acid residue with an ethyl side chain.

In certain embodiments, the downstream peptide has a N-terminal β- or γ-thiol amino acid residue. For example, in one embodiment, a downstream peptide having an N-terminal amino acid residue with the side chain —CH(CH$_3$)CH$_2$SH is combined with an upstream peptide having a protected N-terminal cysteyl residue, a protected N-terminal β- or γ-thiol amino acid residue, or a N-terminal non-thiol containing residue and a C-terminal thioester group to form an initial ligation product having an amide bond between the α-carbon of the C-terminal of the upstream peptide and the α-carbon of the N-terminal of the downstream peptide. In a subsequent step, the initial ligation product is treated with hydrogen and a catalyst, as previously described, to convert the amino acid residue with the side chain —CH(CH$_3$)CH$_2$SH into a valyl residue thereby forming a subsequent ligation product.

In another embodiment, a downstream peptide having a N-terminal amino acid residue with either the side chain —CH(CH$_3$)CH(CH$_3$)SH or the side chain —CH(CH$_2$SH)CH$_2$CH$_3$ is combined with an upstream peptide having a protected N-terminal cysteyl residue, a protected N-terminal β- or γ-thiol amino acid residue, or a N-terminal non-thiol containing residue and a C-terminal thioester group to form an initial ligation product having an amide bond between the α-carbon of the C-terminal of the upstream peptide and the α-carbon of the N-terminal of the downstream peptide. In a subsequent step, the initial ligation product is treated with hydrogen and a catalyst, as described previously, to convert the amino acid residue with either the side chain —CH(CH$_3$)CH(CH$_3$)SH or the side chain —CH(CH$_2$SH)CH$_2$CH$_3$ into an isoleucyl residue thereby forming a subsequent ligation product.

In another embodiment, a downstream peptide having a N-terminal amino acid residue with a side chain —CH$_2$CH(CH$_3$)CH$_2$SH is combined with an upstream peptide having a protected N-terminal cysteyl residue, a protected N-terminal β- or γ-thiol amino acid residue, or a N-terminal non-thiol containing residue and a C-terminal thioester group to form an initial ligation product having an amide bond between the α-carbon of the C-terminal of the upstream peptide and the α-carbon of the N-terminal of the downstream peptide. In a subsequent step, the initial ligation product is treated with hydrogen and a catalyst, as described previously, to convert the amino acid residue with the side chain —CH$_2$CH(CH$_3$)CH$_2$SH into a leucyl residue thereby forming a subsequent ligation product.

In certain embodiments, the invention contemplates that the subsequent ligation product is purified using reverse phase HPLC, recrystallization, or a combination of purification strategies. It is contemplated that the subsequent ligation product may be further modified, as previously described, for further use in convergent or non-convergent kinetically controlled ligation. For example, the subsequent ligation product may be modified with a better leaving group at the C-terminal to give a C-activated ligation product. Alternatively, if the subsequent ligation product has a protected N-terminal cysteyl or other protected N-terminal β- or γ-thiol amino acid residue, this residue can be deprotected to yield a N-activated ligation product. In other embodiments, the ligation product, the modified ligation product, the C-activated ligation product, or the N-activated ligation product from a kinetically-controlled ligation can be the initial ligation product in the selective desulfurization method.

It is further contemplated that the native chemical ligation method using N-terminal β- or γ-thiol amino acid residues, other than cysteyl, followed by selective desulfurization may be modified to be a kinetically-controlled ligation by using different leaving groups at the C-terminals of the peptides to be joined. In certain embodiments, the native chemical ligation method using N-terminal β- or γ-thiol amino acid residues, other than cysteyl, followed by selective desulfurization is kinetically-controlled and fully convergent.

In certain embodiments, the invention allows for ligations at alanyl residues when combined with selective desulfurization. For example, unprotected cysteinyl residues can be desulfurized in the presence of Cys(Acm) and methionyl residues, without desulfurizing the Cys(Acm) or methionyl residues. In certain embodiments, protected cysteinyl residues, such as a thiazolidine-protected N-terminal cysteinyl residue can be desulfurized in the in the presence of Cys(Acm) and methionyl residues, without desulfurizing the Cys(Acm) or methionyl residues. In certain embodiments, protected cysteinyl residues, such as a thiazolidine-protected N-terminal cysteinyl residue can be desulfurized in the in the presence of a thioether, without desulfurizing the thioether. In some embodiments, cysteinyl residues can be desulfurized in the presence of C-terminal thiol-based or thioester-based leaving groups, without desulfurizing the thiol-based or thioester based leaving groups, and without desulfurizing any Cys(Acm) or methionyl residues.

In certain embodiments, in order to expand the scope of Native Chemical Ligation (NCL), the methods of this invention can be used to synthesize a polypeptide via ligation chemistry at sites other than Xxx-Cys. A person of knowledge in the prior art will appreciate that Xxx-Cys positions in a protein sequence are oftentimes limiting in terms of their position, thus requiring the synthesis of long peptides. For example, some embodiments allow larger proteins to be prepared from smaller peptides resulting in a more efficient synthesis. In certain embodiments, polypeptides or proteins can be synthesized by a combination of ligation reactions at Xxx-Cys and non Xxx-Cys sites. For example, peptides are obtained that contain cysteinyl residues in positions corresponding to alanyl residues in the target polypeptide or protein that is to be synthesized. Thereby junctions can be created for NCL. In certain embodiments, polypeptides can be synthesized using the convergent and non-convergent ligation methods of this invention combined with the selective desulfurization methods of this invention; thereby polypeptides and proteins can be built by native chemical ligation from disconnections at the more common Xxx-Ala ligation sites, in addition to Xxx-Cys sites, even in polypeptide and protein targets that contain other Cys residues.

The invention also contemplates combining the chemical methods and compositions based on kinetically-controlled ligation with alkylation methods to convert cysteyl residues to either pseudo-aspartyl, pseudo-glutamyl, pseudo-asparaginyl, or pseudo-glutaminyl residues as discussed by Kochendoerfer et al., 2003, which is hereby incorporated by reference. In one embodiment, for example, a downstream peptide having an N-terminal cysteyl residue is combined with an upstream peptide having a protected N-terminal cysteyl residue, a protected N-terminal β- or γ-thiol amino acid residue, or a N-terminal non-thiol containing residue and a C-terminal thioester group to form an initial ligation product having an amide bond between the α-carbon of the C-terminal of the upstream peptide and the α-carbon of the N-terminal of the downstream peptide. In a subsequent step, the initial ligation product is treated with bromoacetic acid to convert the cysteyl residues into pseudo-glutamyl residues, thereby forming a subsequent ligation product, wherein the side chains of the pseudo-glutamyl residues have the structure —CH$_2$SCH$_2$C(O)OH. The advantage of this combination method is the ability to convert a cysteyl residue into a residue that is electronically and sterically similar to a glutamyl residue. It is contemplated that a peptide may be alkylated in the manner described both prior to and subsequent to a kinetically controlled ligation. It is contemplated that the subsequent ligation product may be further modified, as previously described, for further use in convergent or non-convergent kinetically controlled ligation. For example, the subsequent ligation product may be modified with a better leaving group at the C-terminal to give a C-activated ligation product. Alternatively, if the subsequent ligation product has a protected N-terminal cysteyl or other protected N-terminal β- or γ-thiol amino acid residue, as described above, this protected residue can be deprotected to yield a N-activated ligation product. In other embodiments, the ligation product, the modified ligation product, the C-activated ligation product, or the N-activated ligation product from a kinetically-controlled ligation can be the initial ligation product in the alkylation method.

The invention also contemplates combining the chemical methods and compositions based on kinetically-controlled ligation with chemoselective amide ligations by decarboxylative condensations of N-alkylhydroxylamines and α-ketoacids as discussed in Bode et al. (2006).

In certain embodiments, the synthetic products made using the methods and compositions of kinetically controlled ligation, either alone or in combination with the other methods described above, have a N-terminal cysteyl, N-terminal β- or γ-thiol amino acid residue, or a N-terminal amino acid residue. In these certain embodiments the synthetic products also have a C-terminal thioester and can thus be joined at either end to a recombinantly expressed peptide or polypeptide (Muir, 2003; Gentle et al., 2004.

G. Implementation of Reactions

Reactions may be conducted under a number of different conditions so long as the desired end product and yield are obtained. It is contemplated that reactions may occur in batch, though other implementations are also included. For example, a fed-batch process may be used for reactions. The term "fed-batch process" means that there is an initial reaction mixture in which all of the components are present (batch reaction) and that the reaction is then occasionally supplemented with one or more components thereafter. Thus, a component introduced by the fed-batch process refers to the supplementation of that component in discrete amounts to a reaction after the reaction has commenced.

Moreover, embodiments of the invention may involve the use of a solid support, including one that is non-reactive with respect to the reaction at issue. It is contemplated that one or more components of the reaction may be immobilized on the support.

Reactions may be conducted at an initial temperature of about, at least about, or at most about, 15, 16, 17, 18, 19, 20, 21, 22, 23, 24, 25, 26, 27, 28, 29, 30, 31, 32, 33, 34, 35, 36, 37, 38, 39, or 40° C., or any range derivable therein. In certain embodiments, the reaction occurs at room temperature, which is understood to refer to a temperature between about 20 and about 27° C.

Moreover, reactions take initially take place at a pH between about, at least about, or at most about 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0 or more (or any range derivable therein). In certain embodiments, conversion of a Thz-peptide-thioester to a Cys-peptide-thioester occurs at a pH of about 4.0. In other embodiments, formation of a peptide-thiophenylester from a peptide-thioester was conducted in a reaction having a pH of about 6.8. A ligation reaction can occur, in particular embodiments, at a pH of about 6.8.

It is contemplated that the concentration of each and/or both peptides can be about, at least about or at most about 0.2, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0 mM or more, or any range derivable therein. Peptides may initially be in a lyophilized form.

It is also contemplated that reactions may be scaled up from what is described herein by 2×, 3×, 4×, 5×, 6×, 7×, 8×, 9×, 10×, 11×, 12×, 13×, 14×, 15×, 16×, 17×, 18×, 19×, 20×, 25×, 30×, 40×, 45×, 50×, 55×, 60×, 70×, 80×, 85×, 90×, 95×, 100×, or more, or any range derivable therein.

Reactions may be performed in the absence or presence of an exogenous catalyst, depending on the chemical groups being reacted.

Thiophenol, or benezenethiol, has been used as the standard catalyst for Native Chemical Ligation (NCL) since development of the concept in the early 1990s. While it seems to work reasonably well for most NCL reactions, drawbacks include its poor solubility in the aqueous solvents used for NCL, an unpleasant odor, and the fact that it is a liquid at room temperature and pressure. The poor solubility of thiophenol limits the amount of thiol-thioester exchange that can occur in a typical NCL reaction, which is the rate-limiting step in most NCL reactions. Consequently, ligation reactions often require incubation for extended periods of time before reaching completion, with the possibility of side reactions occurring during this incubation that decrease purity and yield of the final product. Therefore, in embodiments involving an exogenous catalyst, it is contemplated that in some cases the catalyst is not a thiophenol.

An ideal catalyst for NCL would be able to quantitatively exchange the alkyl thioester to a more active aryl thioester in a short period of time in the volume of a typical NCL reaction, and the resulting peptide thioester would be equally or more reactive than a thiophenyl thioester. This would allow for greatly reduced reaction times, and potentially cleaner NCL reactions. One could also use such a catalyst to pre-form the peptide-thioester rather than as an in situ reagent during NCL, which would speed up the ligation reactions and make convergent ligations more straightforward. The thiol should be a solid and not malodorous.

A model ligation reaction was used to test different potential catalysts for NCL. A peptide alkyl thioester LYRAL-COSR'-L (SEQ ID NO:6), where R'=propionic acid, was reacted with an N-terminal cysteine peptide CLYLAA (SEQ ID NO:7) in 6M GdmCl, 200 mM phosphate, 20 mM TCEP, 10 mM thiol catalyst, at pH 7.0. CLYLAA (SEQ ID NO:7) was present in two-fold excess (2 mM) over the thioester peptide (1 mM). Thiol-thioester exchange and ligation rates were determined by withdrawing samples of the ligations at various time points, quenching with acid, and analyzing by RP-HPLC. Based on this set of experiments, in certain embodiments water-soluble phenyl thiols that have a pKa near 7.0, such as 4-mercaptophenylacetic acid, can be used to increase the rate of NCL by increasing the rate of thiol-thioester exchange with peptide-alkyl thioesters. Preformation of peptide-phenyl thioesters is also more straightforward with such water-soluble thiols compared to thiophenol. Therefore, water-soluble thiols such as 4-mercaptophenylacetic acid and other such thiols in Table 3 should be useful in both sequential and convergent ligations.

H. Purification

A number of purification methods can be employed to purify peptides for use in ligation reactions or the desired polypeptide once synthesis is complete. See, for example, Cutler, 2003 and Aguilar, 2004, which are both incorporated by reference.

For instance, HPLC, such as reverse phase HPLC, can be implemented. One or more columns may be used in any purification procedure to isolate the desired protein.

Following purification, a peptide or polypeptide may be lyophilized.

II. POLYPEPTIDES AND PEPTIDES

The present invention concerns polypeptide fragments (peptides) that can be used to synthesize a polypeptide. The length of the peptide or resulting polypeptide need not be a limitation of the present invention. Therefore, peptides may be, be at least, or be at most 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 350, or 400 residues in length, or any range derivable therein. Polypeptides may be, be at least, or be at most, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 350, 400, 450, 500, 550, 600, 650, 700, 750, or 800 residues in length, or any range derivable therein. Longer lengths are possible, though few such polypeptides are known in nature.

The synthesized polypeptide may be active or functional with respect to the native protein. It may exhibit about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%, or any range derivable therein of any activity or function of the native protein based on a specific assay or measurement. Moreover, it is contemplated that more than one polypeptide may be incubated under appropriate folding conditions to form an active or functional protein. The protein ma be composed of homopolymers (same polypeptides) or heteropolymers (different polypeptides). Such conditions are well known to those of skill in the art.

The peptides and polypeptides are disclosed herein as amino acid residue sequences. Those sequences are written left to right in the direction from the amino to the carboxy terminus. In accordance with standard nomenclature, amino acid residue sequences are denominated by either a single letter or a three letter code as indicated below.

The invention is not limited by the amino acid sequence of the desired polypeptide, though in particular embodiments, that polypeptide has one or more cysteine residues.

Accordingly, the peptides and polypeptides disclosed herein will be understood to encompass amino acid residue sequences comprising at least one of the 20 common amino acids in naturally synthesized proteins.

TABLE 1

| Amino Acid Residue | 3-Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Amino acids include the L and D isoforms of chiral amino acids.

Moreover, in some embodiments it is contemplated that a peptide or polypeptide may contain at least one modified or unusual amino acid, including but not limited to those shown on Table 2 below. In certain embodiments, however, the modified or unusual amino acid residue will not be located at either the C-terminus, N-terminus or both of the peptide or polypeptide.

TABLE 2

| Abbr. | Amino Acid |
|---|---|
| Modified and Unusual Amino Acids | |
| Aad | 2-Aminoadipic acid |
| Baad | 3-Aminoadipic acid |
| Bala | β-alanine, β-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| Baib | 3-Aminoisobutyric acid |

TABLE 2-continued

| Abbr. | Amino Acid |
|---|---|
| Modified and Unusual Amino Acids | |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| AIle | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

III. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

A set of chemical tactics are described below based on a novel principle—"kinetically controlled ligation"—that enables a highly practical, fully convergent strategy for the synthesis of a target protein.

Example 1

Materials and Methods for Example 2

Peptide Segment Synthesis (Peptide-$^\alpha$carboxylate or Peptide-$^\alpha$thioester)

Peptides were prepared manually by "in situ neutralization" Boc chemistry stepwise solid phase peptide synthesis (Dawson and Kent, 2000), on —OCH$_2$-Pam-resins (free $^\alpha$ carboxyl peptides) or on HSCH$_2$CH$_2$CO-Leu-OCH$_2$-Pam-resin ($^\alpha$thioester peptides) (Kochendoerfer et al., 2003). Side-chain protection for amino acids was as follows: Arg(Tos), Asn(Xan), Asp(OcHex), Cys(4-CH3Bzl), Glu(OcHex), Lys (2-Cl—Z), Ser(Bzl), Thr(Bzl), Tyr(Br—Z). The 1,3-thiazolidine-4-carboxo (Thz) group was introduced to protect the N-terminal Cys of the middle peptide segments, and Boc-L-thiazolidine-4-carboxylic acid was used for peptide synthesis. After chain assembly was complete, peptides were deprotected and simultaneously cleaved from the resin support by treatment with anhydrous HF containing p-cresol (90:10, vol/vol) for 1 h at 0° C. After evaporation of the HF under reduced pressure, crude products were precipitated and triturated with chilled diethyl ether, and the peptide products were dissolved in 50% aqueous acetonitrile containing 0.1% TFA. Peptide compositions were confirmed by LC-MS. [Thr$^1$-Cys$^3$]-$\alpha$thioester (observed mass (ob.) 525.4±0.4 Da, calculated average mass (ca.) 524.6 Da); [Thz$^4$-Ala$^{15}$]-$\alpha$thioester (SEQ ID NO:8), (ob. 1491.4±0.5 Da, ca. 1491.8 Da); [Cys$^{16}$-Leu$^{25}$]-$\alpha$thioester (SEQ ID NO:9), (ob. 1257.2±0.5 Da, ca. 1257.6 Da); [Thz$^{26}$-Gly$^{31}$]-$\alpha$thioester (SEQ ID NO:27), (ob. 827.5±0.5 Da, ca. 828 Da); [Cys$^{32}$-Thr$^{39}$]-$\alpha$thioester (SEQ ID NO:28), (ob. 987.8±0.5 Da, ca. 988.3 Da); and [Cys$^{40}$-Asn$^{46}$] (ob. 738.4±0.5 Da, ca. 738.8 Da) (SEQ ID NO:29).

Preparation of Peptide-$\alpha$thiophenylester from Peptide-$\alpha$thioester

Lyophilized peptide-$\alpha$thioester after HF cleavage was used for the exchange reaction. The crude peptide was dissolved in pH 6.8 aqueous buffer containing 6 M guanidine hydrochloride and 0.2% thiophenol (vol/vol). Peptide concentration in the solution was ca. 0.2 mM. The reaction mixture was vigorously stirred for 12 hours with exclusion of air, and analyzed by LC-MS. After the conversion, the reaction was quenched (acidified to pH 3) by addition of aqueous 6N HCl. Residual thiophenol and oxidized thiophenol (diphenyl disulfide) were removed by extraction with diethyl ether. Acid quenching was necessary before the diethyl ether extraction procedure in order to prevent transthioesterification with residual HSCH$_2$CH$_2$CO-Leu that could not be extracted. The peptide-$\alpha$thiophenylester was purified by preparative HPLC, confirmed by mass spectrometry, and lyophilized.

Ligation Reactions

Kinetically-controlled ligation (based on the nature of the thioester) was performed in pH 6.8, 200 mM phosphate phosphate buffer containing 6M guanidine hydrochloride, at a concentration of 2 mM for each peptide.

Kinetically-controlled ligation (based on the titration of {peptide1-$\alpha$thioester} by {Cys-peptide2-$\alpha$thioester} in our earlier scheme ('titration strategy'), which was employed with limited success. A peptide1-$\alpha$thioester was dissolved to a concentration of approximately 20 mM in 0.5 M Bis-Tris buffer containing 6 M guanidine hydrochloride and 1% thiophenol (vol/vol), and the reaction mixture was stirred at room temperature. The Cys-peptide2-$\alpha$thioester was maintained in unbuffered aqueous 6 M guanidine hydrochloride (pH 4~5) to prevent any ligation reaction before its titration (i.e., slow addition) into the ligation mixture. This unbuffered solution of Cys-peptide2-$\alpha$thioester was added slowly to the peptide1-$\alpha$thioester solution. The titration rate was controlled to be finished in several hours.

Native Chemical Ligation was carried out under the same conditions used for the kinetically-controlled ligation, except 1% (v/v) thiophenol was added to the reaction mixture.

Preparative Reverse Phase HPLC Purification.

To purify synthetic peptides and ligation products, preparative HPLC was performed on a Waters Prep LC 4000 system by use of preparative Vydac C8 column (12 μm, 2.2×25 cm) at flow rate of 10 mL/min and by use of semi-preparative Vydac C4 and C8 columns (1 cm×25 cm) at a flow rate of 5 mL/min, with a gradient of 10-40% buffer B in buffer A over 60 min. Buffer A: 0.1% TFA in water; Buffer B: 0.08% TFA in acetonitrile. Fractions were collected across the expected elution time and combined based on HPLC and LC-MS analysis.

Example 2

Convergent Synthesis

Figure 2:
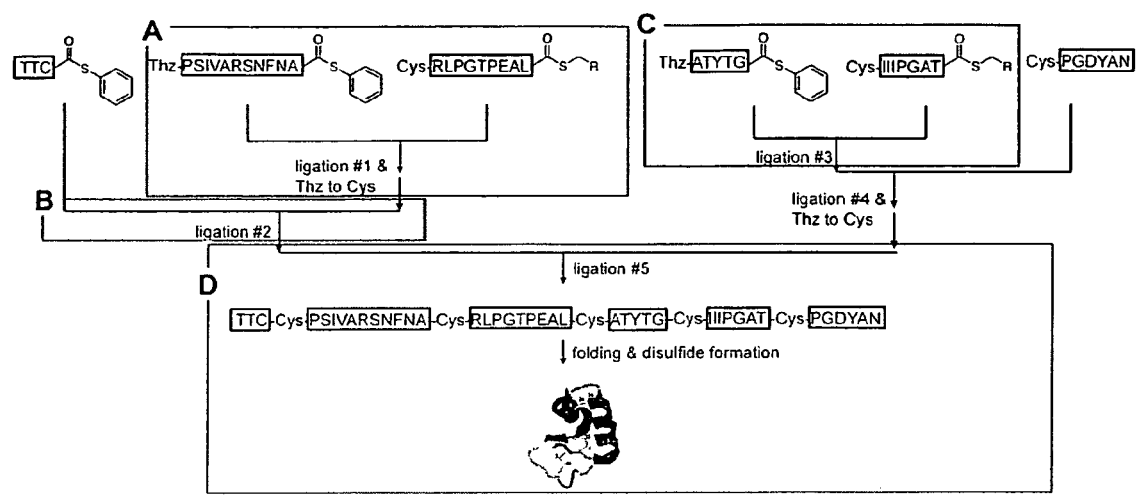
FIGS. 2A-D. Total chemical synthesis of the model protein crambin by the fully convergent ligation of six unprotected peptide segments. Key aspects of the chemical tactics are exemplified in different steps, as follows: A highlights a regioselective native chemical ligation, followed by unmasking of the cryptic Cys-residue at the N-terminal of the ligation product (SEQ ID NOS: 11 and 9); B & C are also regioselective native chemical ligation steps (SEQ ID NOS: 27, 28 and 29); D highlights the final convergent step in which the two halves of the polypeptide are joined to give the full length product (SEQ ID NO:30).

Synthesis of the model protein crambin (Bang and Kent, 2004; Bang and Kent, 2005; Teeter et al., 1981; Jelsch et al., 2000; Bang et al., 2004) with fully convergent approach was attempted from six unprotected peptide segments. The sequence of the target molecule and the synthetic design are shown in FIG. 2. This synthesis presents concrete examples of the challenges involved in making a protein from multiple peptide segments by a fully convergent route.

Key aspects of the chemical tactics for the convergent synthesis are exemplified at various points in this synthesis. Thus, ligations #1, #2, and #3 in FIG. 2 require the regioselective reaction of a peptide1-$\alpha$thioester with a Cys-peptide2-$\alpha$thioester to give a single product, the desired peptide1-Cys-peptide2-$\alpha$thioester. Also the Thz-peptide-$\alpha$thioester product from ligation #1 must be converted to the corresponding Cys-peptide-$\alpha$thioester so that it can be used for the next convergent ligation step (ligation #2 in FIG. 2). A practical means for accomplishing these chemical transformations will enable a general convergent synthesis of proteins.

Figure 3:
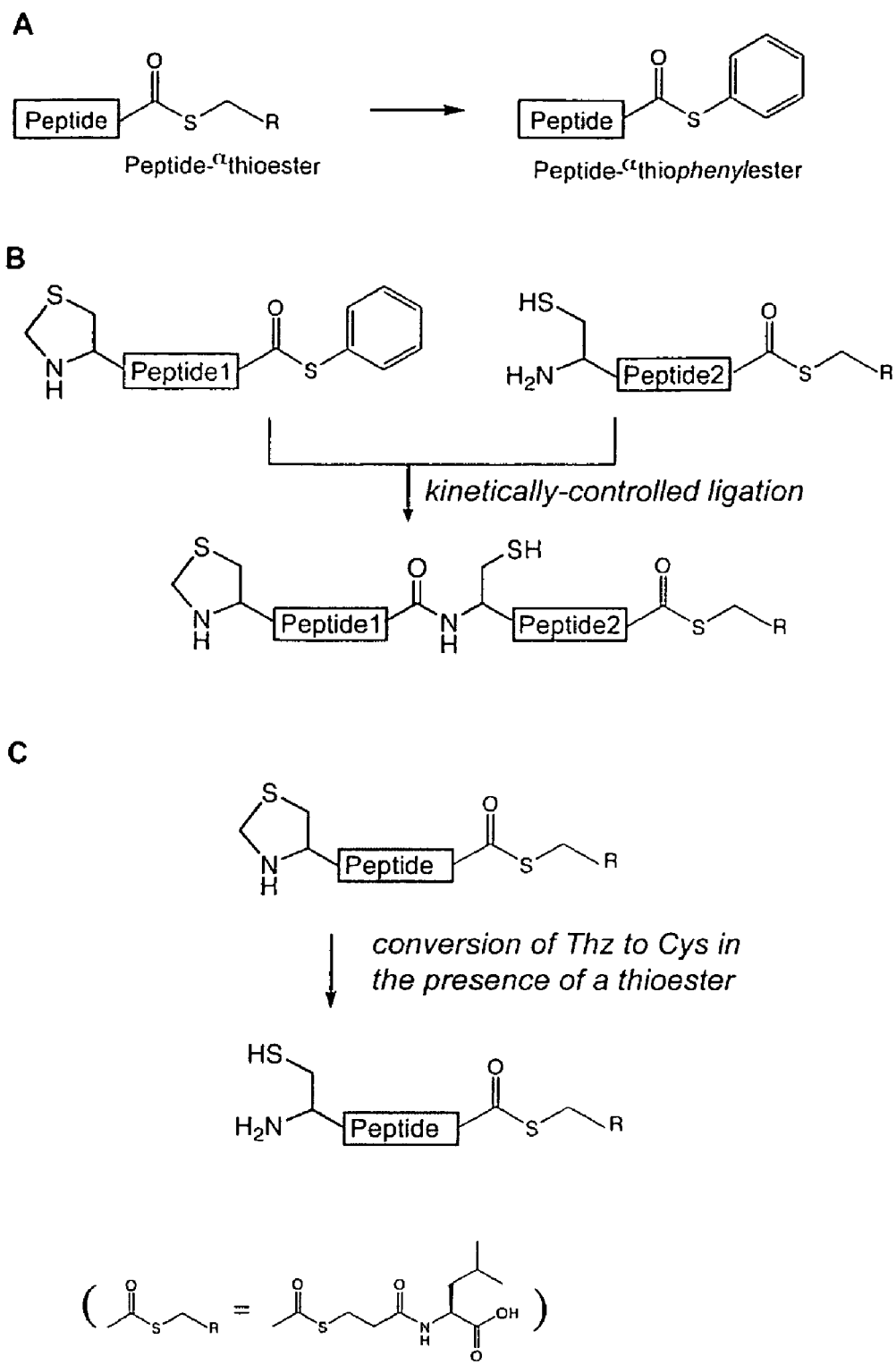
FIG. 3A-C. Key steps for the realization of convergent chemical ligation. A. Conversion of a peptide-αthioester to a peptide-αthiophenylester. B. Kinetically-controlled ligation of a Thz-peptide1-αthioester and a Cys-peptide2-αthioester to give only the desired product, Thz-peptide1-peptide2-αthioester. C. Conversion of a Thz-peptide-αthioester to the Cys-peptide-αthioester.

The chemical tactics are formulated around the use of Native Chemical Ligation, the thioester-mediated covalent joining of unprotected peptide segments at a cysteine residue (Dawson et al., 1994). The three key chemical transformations that must be carried out in order to use native chemical ligation in convergent synthesis are shown in FIG. 3. The major challenge is to control the intrinsic dual reactivity of the bifunctional Cys-peptide2-$\alpha$thioester under native chemical ligation reaction conditions, so that it will react with a peptide1-$\alpha$thioester to yield only a single product (see FIG. 2B).

A Cys-peptide2-thioester under native chemical ligation conditions will undergo multiple reactions to form cyclic{Cys-peptide2}, Cys-peptide2-Cys-peptide2-thioester, and other products of oligomerization and cyclization (Zhang and Tam, 1997; Evans et al., 1999). Prior to this work, a Cys-peptide2-thioester could not be seriously considered for use in convergent synthesis because of the intrinsic dual reactivity of this type of bifunctional molecule; reaction with a peptide1-thioester would give a series of products from competing reactions of the two thioester moieties. In preliminary studies, we attempted to take advantage of the dependence of native chemical ligation rates on the nature C-terminal amino acid residue of a peptide-thioester. We also tried another scheme that made use of the titration of a high concentration of peptide1-thioester with a Cys-peptide2-thioester. These concepts turned out to be of limited use for practical chemical protein synthesis by a convergent route.

Figure 4:
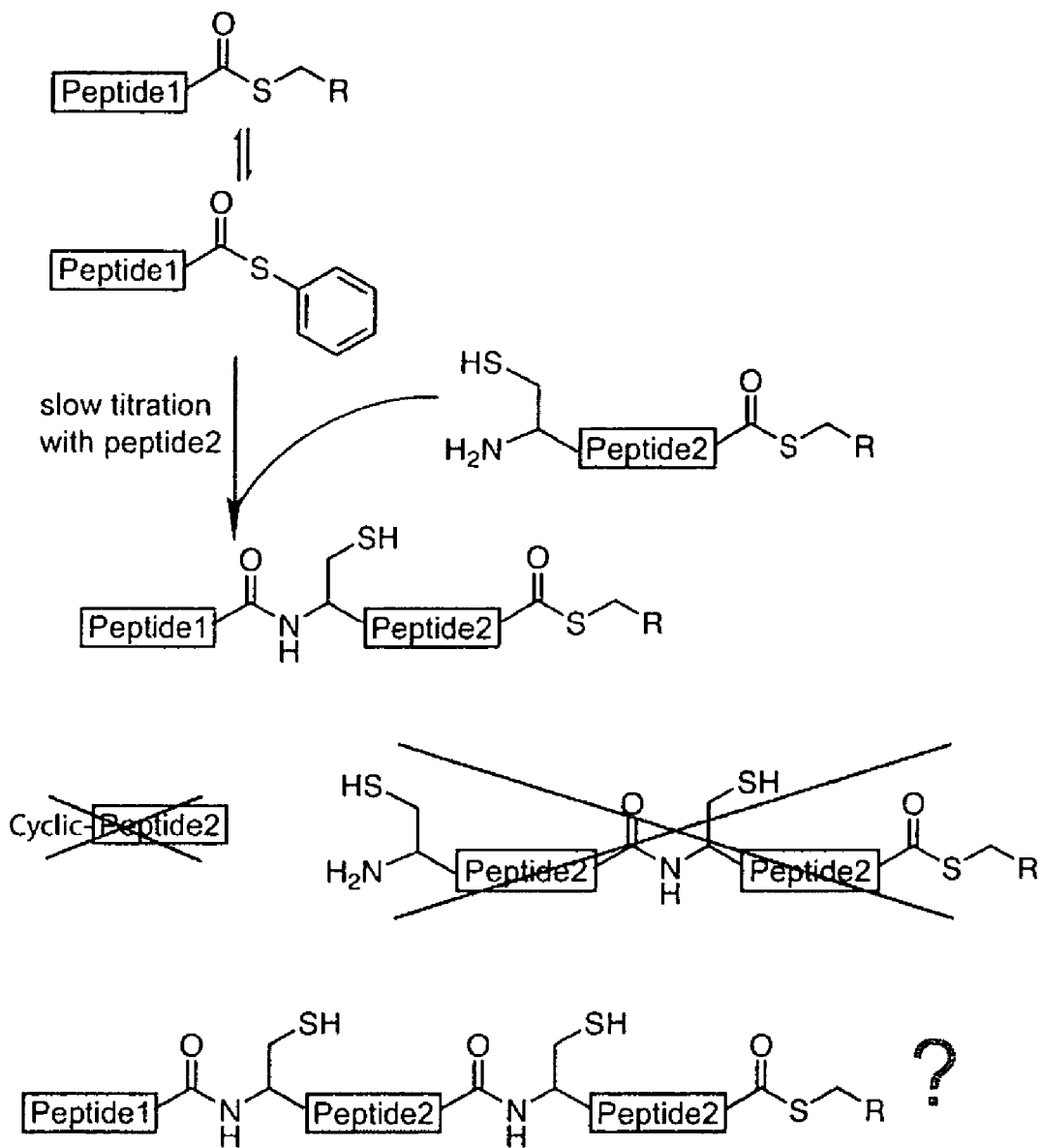
FIG. 4. An earlier scheme ('titration strategy') for the native chemical ligation of two peptide-αthioesters that minimizes the formation of the undesired by-products.

A scheme ('titration strategy') for the native chemical ligation of two peptide-$\alpha$thioesters that minimizes the formation of the undesired by-products was also investigated (FIG. 4). A high concentration of peptide1-$\alpha$thioester was dissolved in aqueous buffer containing 6M guanidine hydrochloride and 1% thiophenol (vol/vol), and the ligation mixture was stirred. The Cys-peptide2-$\alpha$thioester was maintained at low pH in unbuffered aqueous solution containing 6M guanidine hydrochloride to prevent any reaction before its titration (i.e., slow addition) into the ligation mixture. The titration rate was controlled to be finished in several hours.

Figure 5:
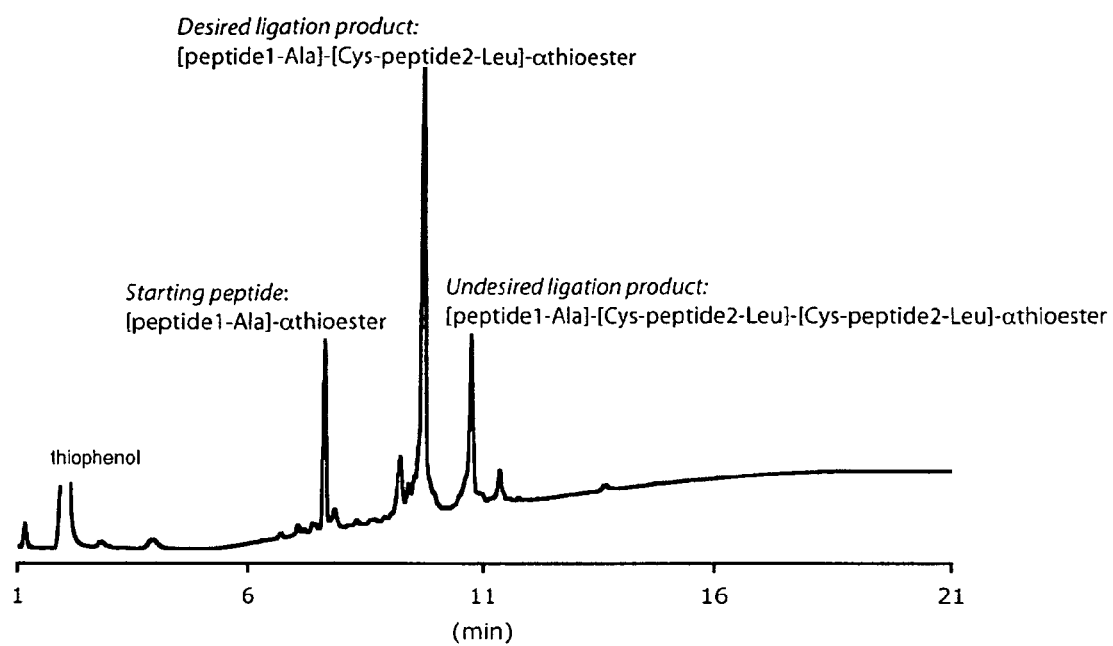
FIG. 5. Titration strategy applied to a model ligation.

This titration strategy was applied to a model ligation (FIG. 5). Two separate peptide solutions were prepared. A peptide1-Ala-$\alpha$thioester (Thz-PSIVARSNFNA-$\alpha$thioester) (SEQ ID NO:8) (9 μmol) was dissolved in 0.5 ml of pH 6.7, 0.5 M Bis-Tris buffer containing 6M guanidine hydrochloride and 1% (v/v) thiophenol (18 mM peptide concentration). A Cys-peptide2-$\alpha$thioester (Cys-RLPGTPEAL-$\alpha$thioester) (SEQ ID NO:9) (10 μmol) was maintained in 0.2 ml water containing 6 M guanidine hydrochloride (pH 4-5) to prevent any ligation reaction before its titration (50 mM peptide concentration). The Cys-peptide2-$\alpha$thioester solution was slowly added to the peptide1-Ala-$\alpha$thioester solution mixture over 4 hours. It was necessary to use excess peptide1-Ala-$^\alpha$thioester to suppress the formation of peptide1-peptide2-peptide2-$^\alpha$thioester The ligation products spontaneously formed a peptide-$^\alpha$thiolactone by transthioesterification with the internal cysteine residues at the ligation site. Thus, the resulting mixture was treated with 200 mM sodium 2-mercaptoethanesulfonate (MES-Na) to convert the peptide-$^\alpha$thiolactone to a peptide-$^\alpha$thioester. Desired product, Thz-PSIVARSNFNA-Cys-RLPGTPEAL-$^\alpha$thio(ethanesulfonate)ester (SEQ ID NO:4) eluted at 9.2 min. (observed mass of 2452.5±0.9 Da. calculated mass=2451.7 Da). Undesired product, Thz-PSIVARS-NFNA-Cys-RLPGTPEAL-Cys-RLPGTPEAL-$^\alpha$thio(ethanesulfonate)ester (SEQ ID NO:10) was eluted at 10.3 min. (observed mass=3490.6±0.9 Da. calculated mass=3489.9 Da). The chromatographic separations were performed on an analytical Vydac C4 column using a linear gradient (5-65%) of buffer B in buffer A over 15 min with a flow rate of 0.5 ml/min (buffer A=0.1% TFA in water; buffer B=0.08% TFA in acetonitrile).

In order to control the outcome of the reaction, a way was devised to obtain a peptide-αthiophenylester from the widely used peptide-αalkylthioester (see FIG. 2A). The inventors proposed that a preformed peptide-αthiophenylester, in the absence of exogenous thiophenol, would react with a Cys-peptide much more rapidly than a standard peptide-αthioester. In the same solution under competitive reaction conditions, this large rate difference would make the standard -αthioester effectively unreactive. This turned out to be the case.

The peptide-thiophenylester was obtained by treating a ca. 0.2 mM solution of crude synthetic peptide-thioester with 0.2% thiophenol (vol/vol) in pH 6.8 aqueous buffer containing 6 M guanidinium hydrochloride for 12 hours at room temperature. The converted peptide-thiophenylester was purified by use of preparative HPLC.

Figure 6:
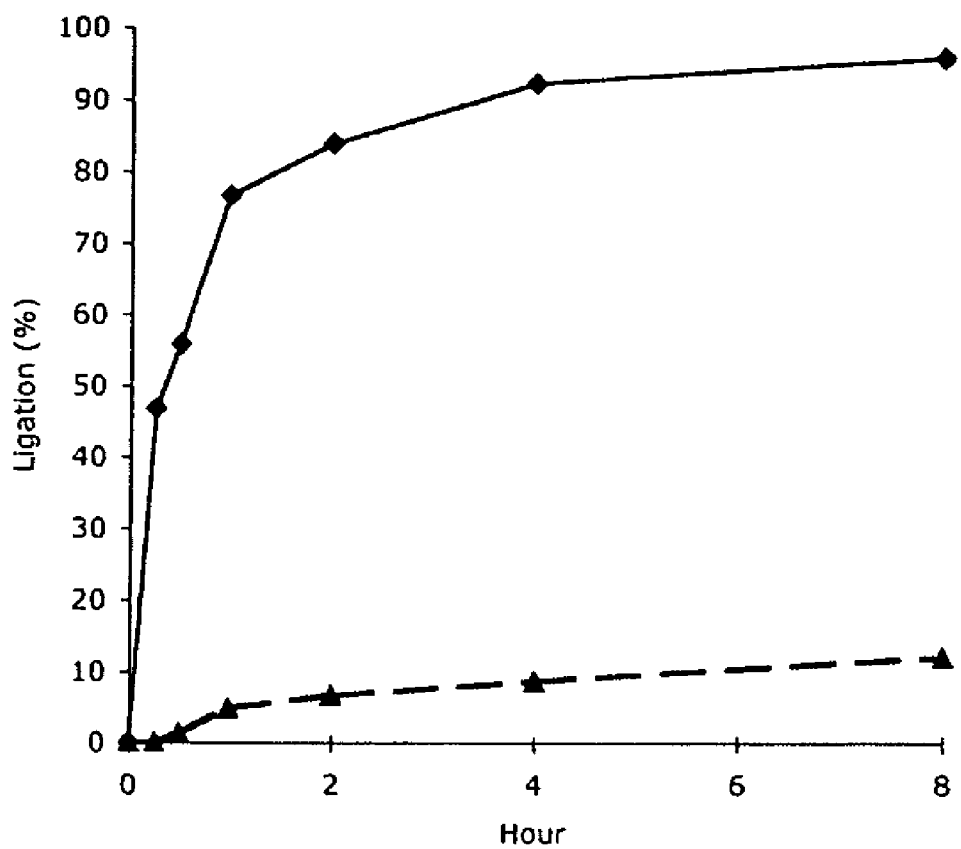
FIG. 6. Comparison of the ligation rates for the reaction of either peptide 1-Ala-αthiophenylester (solid line) or peptide1-Ala-αthioester (dashed line) with a Cys-peptide under identical reaction conditions.

A comparison was done of the ligation rates for the reaction of either peptide1-Ala-$^\alpha$thiophenylester (solid line) or peptide1-Ala-$^\alpha$thioester (dashed line) with a Cys-peptide under identical reaction conditions (FIG. 6). Two separate ligation reactions between 1 mM concentrations of each peptide were carried out in 200 mM phosphate buffer, pH 6.8, containing 6 M guanidine hydrochloride. No thiol additive was present during the ligation reactions. At each time point, an aliquot (20 μl) from the ligation reaction was quenched by addition of 5% trifluoroacetic acid (8 μl ). The aliquot was characterized by analytical HPLC. Analysis of ligated species was done by integrating the area from analytical HPLC profiles at each time point. The model peptides used were: YKMDFHIAA-$^\alpha$thioester (ob. 1296.0±0.6 Da, ca. 1296.5 Da) (SEQ ID NO:1); YKMDFHIAA-$^\alpha$thiophenylester (ob. 1187.1±0.5 Da, ca. 1187.5 Da) (SEQ ID NO:2); and Cys-NVRSGTEPWQL (ob. 1389.3±0.5 Da, ca. 1389.5 Da) (SEQ ID NO:3).

Figure 7:
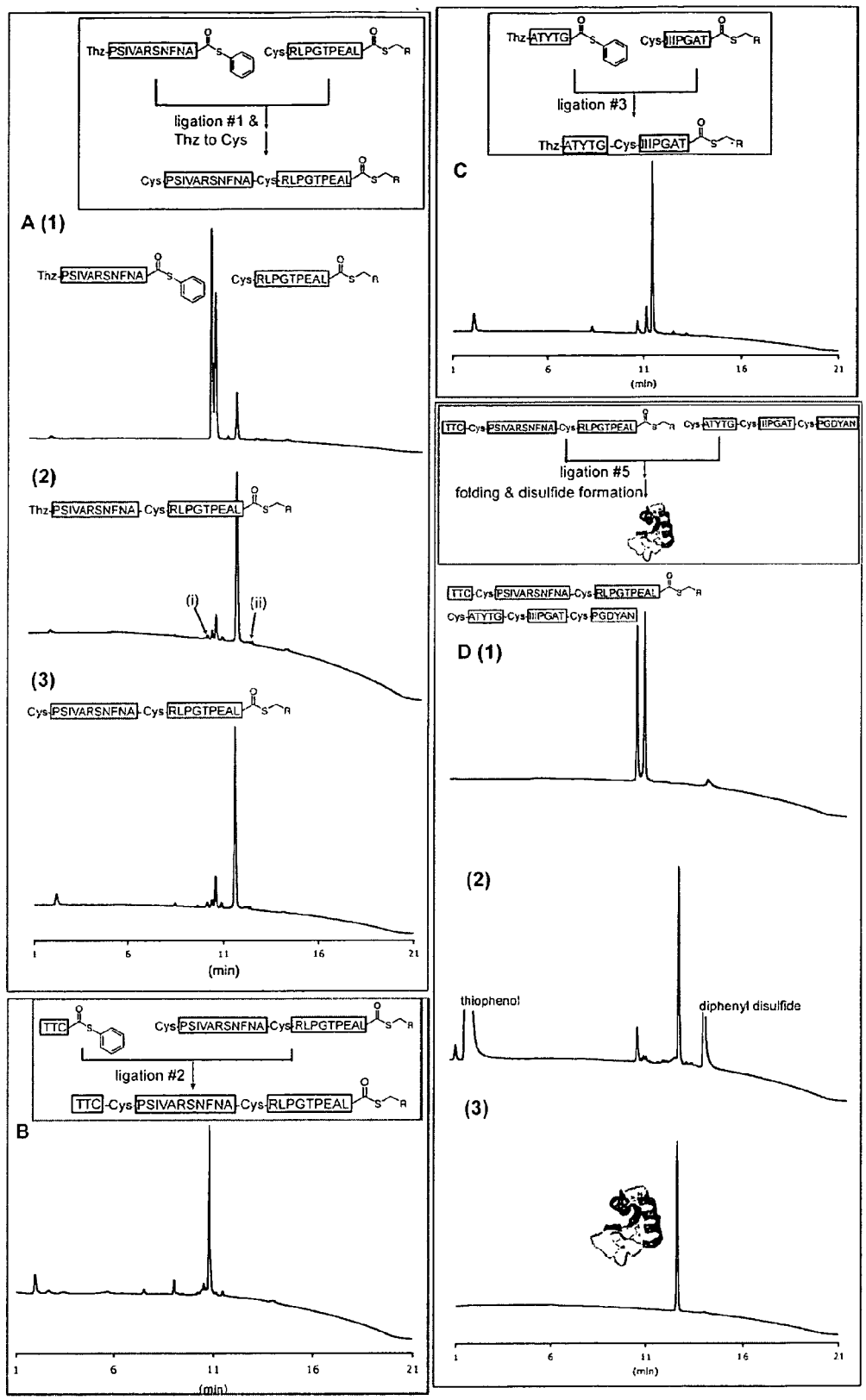
FIG. 7A-D. Analytical reverse phase HPLC data for key chemical transformations in the convergent synthesis of crambin from six peptide segments (SEQ ID NO:30).

The efficacy of this tactic for kinetic control of the outcome of a ligation reaction was shown in ligation #1 in the crambin synthesis (see FIG. 2, Box A), the reaction of Thz ProSerIleValAlaArgSerAsnPheAsnAla-αthiophenylester (SEQ ID NO:11) with Cys-ArgLeuProGlyThrProGluAlaLeu-αthioester (SEQ ID NO:12), in pH 6.6 aqueous buffer in the absence of thiophenol additive. The results are shown in FIG. 7 A(1)&(2). The ligation reaction was complete in one hour and gave the desired product Thz-ProSerIleValAlaArgSerAsnPheAsnAlaCysArgLeuProGlyThrProGluAlaLeu-αthioester (SEQ ID NO:4) in near quantitative yield. (Native chemical ligation reactions are typically performed overnight. With the peptides and concentrations used, a typical native chemical ligation (i.e., a peptide-thioester and a Cys-peptide with 1% thiophenol) would take 10+ hours to go to completion (Hackeng et al., 1999). Only traces of byproducts from undesired reaction of the alkyl thioester were formed (arrows in FIG. 7A(2)). Other attempts to prevent side reactions were only partially successful. It is instructive to compare and contrast the outcomes of two reactions that differ only in the use of a preformed-thiophenylester in one but not the other (cf. FIG. 7A(2) with FIG. 5). With the -thiophenylester, the suppression of the by-products was highly effective; only trace amounts of the previously observed byproducts were detected (arrowed peaks, FIG. 1A(2)). Similar results were obtained for ligations #2 and #3 in the crambin synthesis (FIG. 2 Boxes B & C; results in FIG. 7 B & C).

Another key transformation for the convergent route is to unmask the Thz-peptide-thioester to give a Cys-peptide-αthioester (see FIG. 3C). For the crambin synthesis strategy shown in FIG. 2, the product of ligation #1 from the N-terminal needs to be extended. Thus, the product Thz-ProSerIleValAlaArgSerAsnPheAsnAla-CysArgLeuProGlyThrProGluAlaLeu-αthioester (SEQ ID NO:4) needed to be converted to the corresponding Cys-peptide-αthioester without affecting the thioester moiety. Thioesters are susceptible to attack by amine nucleophiles such as the methoxyamine•hydrochloride used to convert the Thz to Cys (Jencks, 1987). It was conjectured that the quantitative conversion of a Thz-peptide-αthioester to a Cys-peptide-αthioester could be carried out with impunity using methoxyamine-hydrochloride at pH 4. The thioester moiety was unaffected during the quantitative conversion from the Thz-peptide-αthioester to the Cys-peptide-αthioester. Compare the products shown in FIG. 7 A(3) with the starting mixture in FIG. 7 A(2).

All the chemical tools to use native chemical ligation in convergent protein synthesis were achieved: (i) the ability to convert a peptide-αthioester to a peptide-αthiophenylester (FIG. 3A); (ii) the kinetic control of product formation in the ligation of two thioester-containing segments (FIG. 3B); (iii) the ability to effect the quantitative conversion of a Thz-peptide-α thioester to the Cys-peptide-αthioester (FIG. 3C). Thus, we can use distinct forms of the key Cys-peptide-αthioester intermediate to extend a synthesis by ligation at either the N-terminal or C-terminal, at will, in a controlled fashion.

These chemical tools were used to carry out the convergent synthesis of crambin from six peptide segments according to the strategy shown in FIG. 2. The last step was the native chemical ligation of the two halves of the polypeptide chain, followed by folding and disulfide formation to give the synthetic crambin protein. The data are shown in FIG. 1D (1&2). A final purification gave high purity crambin (FIG. 1D (3)) in good yield. Recovered yields were: 71% for ligation #1 and subsequent conversion of Thz to Cys in the same reaction mixture; 50% for ligation #2; 80% for ligation #3 alone; 40% for ligation #3 & subsequent ligation #4 in one-pot; 62% for ligation #5 and subsequent folding in the same reaction mixture.

Example 3

Thioacids as a Reversible Protecting Group for Thioesters

α-Thiocarboxylic acid (α-COSH) under typical native chemical ligation conditions are less activated than α-Thioesters (α-COSR, where R represents aryl or alkyl substituents) towards nucleophilic attack onto the α-carbonyl functionality. Thus this group could be envisaged as a temporary protecting group for thioesters, provided it can be reactivated selectively following the first (N-terminal) ligation reaction. Due to the low pKa value of the thioacid moiety, this functionality remains sufficiently nucleophilic (even) under mildly acidic conditions (e.g., pH 3.5) and can therefore be selectively alkylated with electrophiles, such as α-halocarbonyls. The direct synthesis on a solid support of α-thiocarboxylic acid containing peptides has been described, but is not commonly used and is not straightforward. An elegant alternative for obtaining α-thiocarboxylic acids makes use of α-thioesters as a starting material, which are typically more readily available and can be handled easily. Conversion of the thioester to the thioacid is than achieved by treatment with hydrosulfides (NaSH or KSH) at around neutral pH in aqueous solution (FIG. 9) Thus interconversion of thioacids and thioesters is fully possible. More importantly both reactions appear to be sufficiently specific, giving rise to only a few side reactions under certain conditions. The approach could also be applied to thioester carrying proteins generated by the recently developed expressed protein ligation methodology, which should open up new possibilities in the field of peptide-to-protein ligation.

The utility of this approach is demonstrated by the fully convergent chemical protein synthesis of hen egg-white lysozyme (HEWL, 129 amino acids), which is assembled from four polypeptide segments, each with a length of about 30 amino acids (FIG. 8). The C-terminal portion of the molecule (Fragment 3/4) is generated in a NCL reaction using a thiazolidine (Thz) protected cysteine on the N-terminus of fragment 3.

Figure 9:
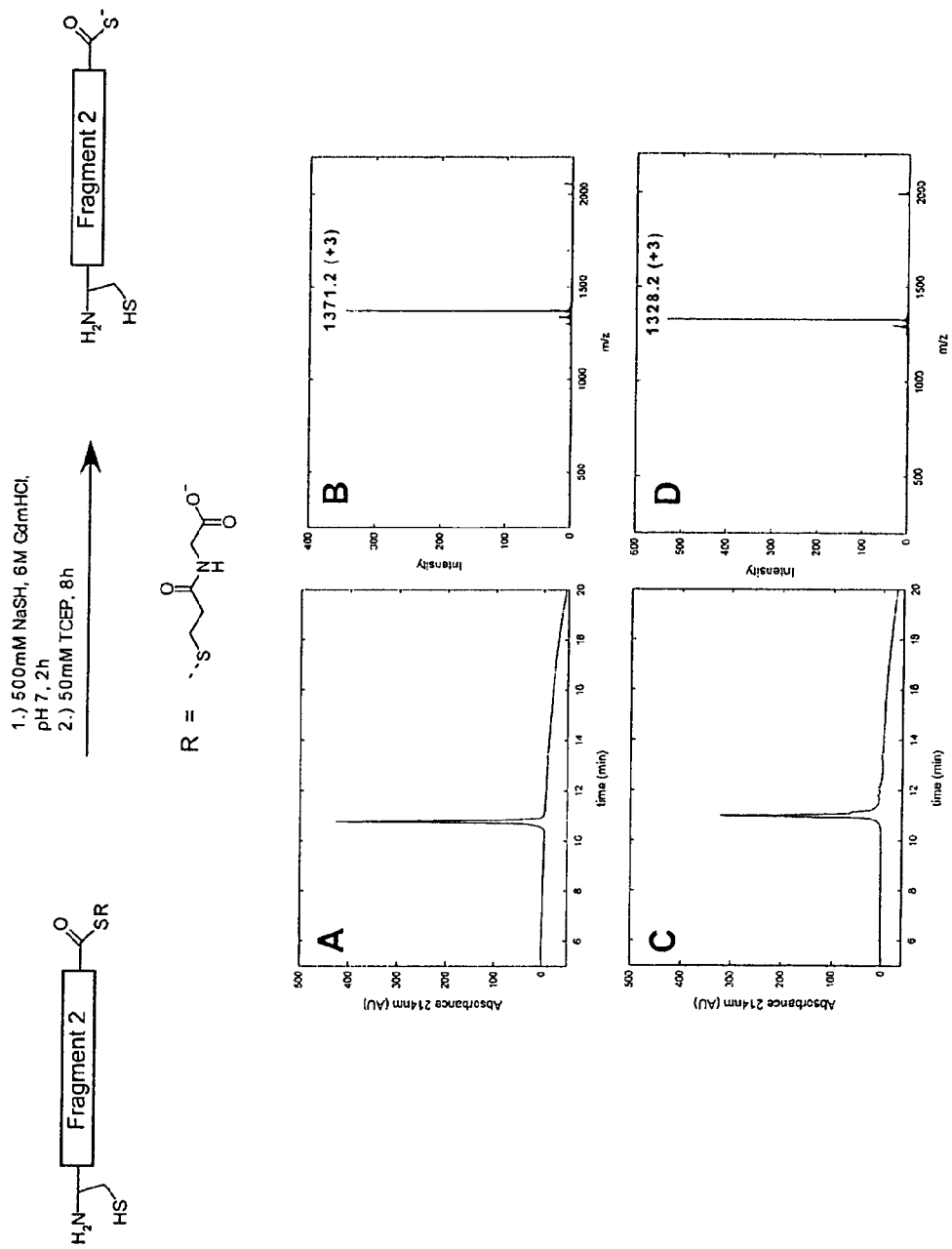
Figure 10:
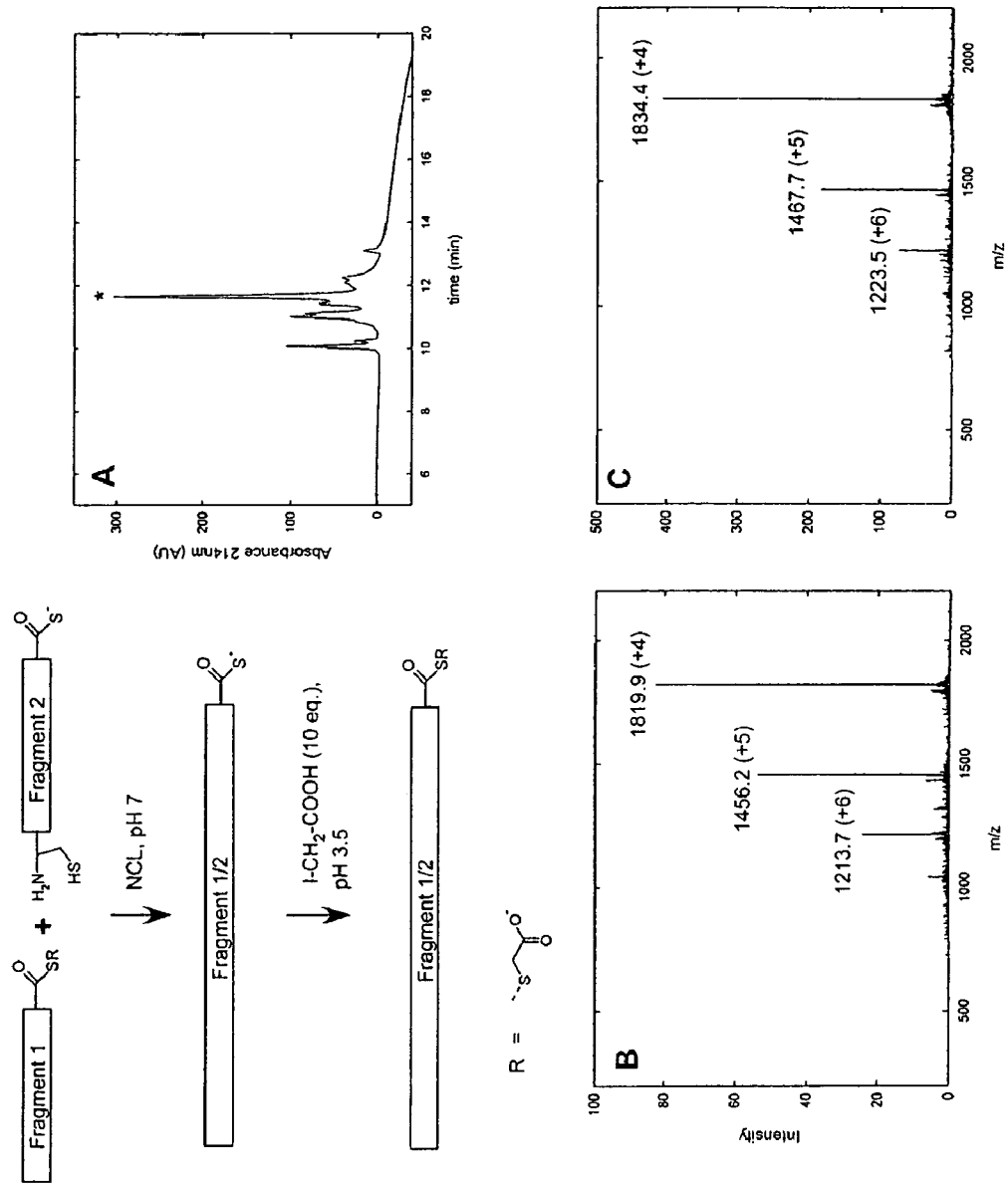
Figure 11:
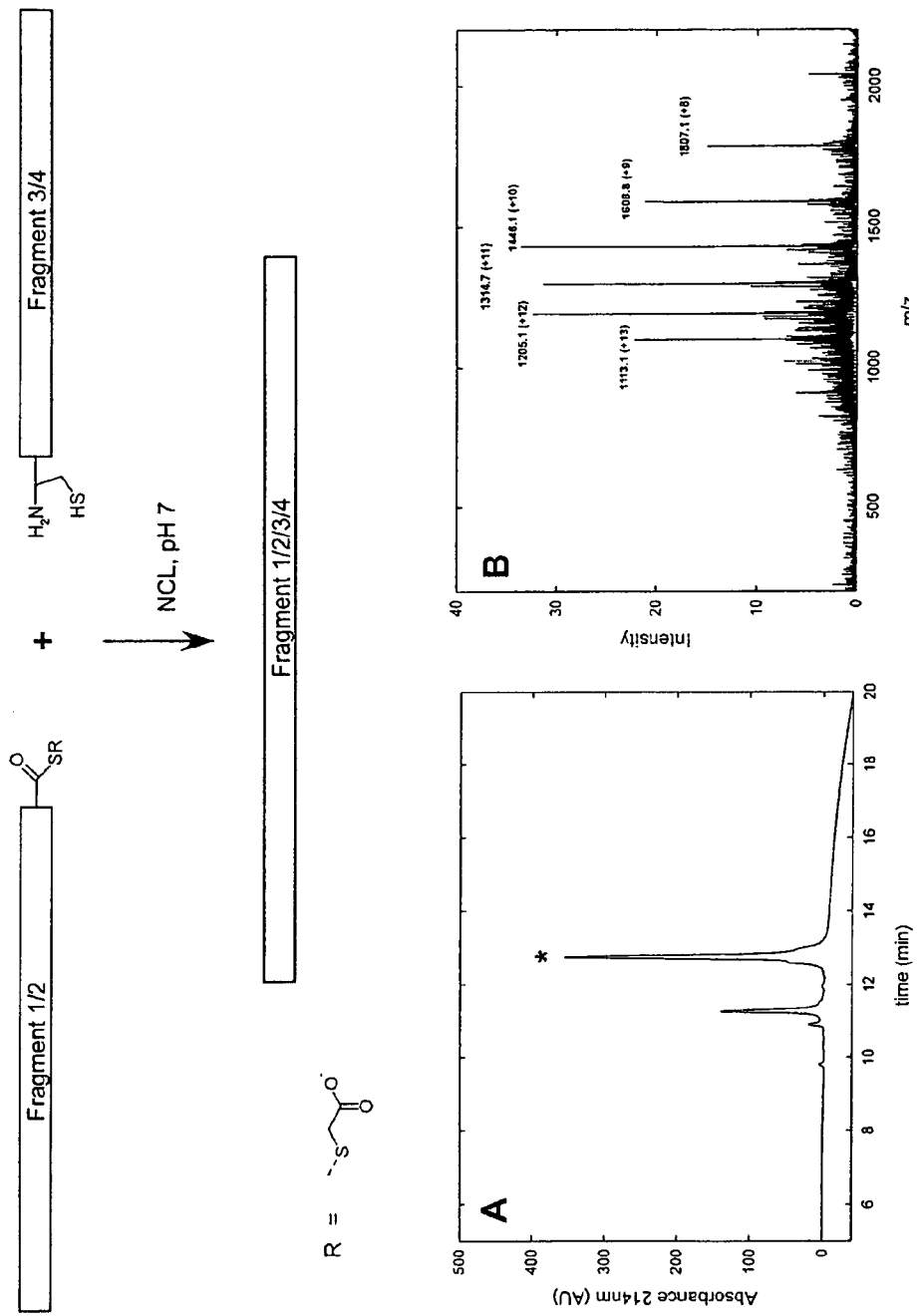

The protecting group ensures regioselectivity of the first ligation reaction and will be removed prior to ligation with Fragment 1/2 representing the N terminal portion of the molecule. Fragment 1/2 is assembled using a temporary thioacid protection of Fragment 2 in order to prevent undesired oligomerization/cyclization reactions when this fragment is subjected to ligation conditions with fragment 1. Thus fragment 2 was assembled as a (activated) thioester using standard SPPS protocols and converted to the corresponding α-thiocarboxylic acid using 500 mM sodium hydrosulfide (NaSH) in 6 M GdmHCl, pH 7.2 for 2 h (FIG. 9). This was followed by a reduction step by adding tris-carboxyethylphosphine to 50 mM and a further incubation for 8 h at 4° C. Following a short solid-phase extraction purification step the material was directly used in a native chemical ligation reaction with thioester carrying fragment 1 under standard conditions (6 M GdmHCl, 100 mM sodium phosphate, pH 7.2, 1% thiophenol, FIG. 10). Once the reaction reached completion, the mixture was acidified to give a pH of 3.5 and 10 eq. of iodoacetic acid were added. Alkylation of the thioacid was complete after a short incubation (2 h) at 4° C. (FIG. 10). The purified N-terminal segment (fragment 1/2) was than ligated to fragment 3/4 using standard ligation conditions to furnish full-length HEWL (FIG. 11).

Example 4

Effects of Thiol Catalysts

The effects of various thiol catalysts (Table 3) on the rates of NCL are shown in FIG. 12. All thiols increased the rate of NCL except for 4-nitrobenzenethiol and the heterocycles 2-mercaptopyridine and 2-mercaptopyrimidine, which either slowed the reaction rate or were no faster than the control. From these data, ligation rates and exchange rates were plotted as a function of the pKa of the thiol (FIG. 13 and FIG. 14). In general, the extent of thiol-thioester exchange increased with increasing pKa, with the alkyl thioesters MESNA and benzyl mercaptan showing the most exchange. However, ligation rates showed a bell-shaped dependence on pKa of the thiol, with a maximum around pKa 7. Two of the most water-soluble thiols that showed catalytic activity and clean ligation reactions, 3-mercaptophenol and 4-mercaptophenylacetic acid, were tested at higher concentrations. The results are shown in FIG. 15. Both showed dramatically increased ligation rates when used at concentrations that are well-beyond the saturation limit of thiophenol in water, with 4-mercaptophenylacetic acid showing better catalytic activity than 3-mercaptophenol. At high concentrations of 4-mercaptophenylacetic acid, ligation rates were essentially identical to that of the pre-formed phenylacetic acid thioester peptide (no thiol added).

TABLE 3

| Thiol | pKa | Solubility at pH 7 |
|---|---|---|
| 2-mercaptopyridine | −1.07 | Soluble |
| 2-mercaptopyrimidine | 2.03 | Very soluble |
| 4-nitrothiophenol | 4.67 | Soluble |
| 3-mercaptobenzoic acid | 5.78 | Very soluble |
| 4-chlorothiophenol | 6.11 | Sparingly soluble |
| 3-mercaptophenol | 6.5 | Very soluble |
| 4-mercaptophenylacetic acid | 6.6 | Very soluble |
| Thiophenol | 6.6 | Slightly soluble |
| 4-methoxythiophenol | 6.75 | Slightly soluble |
| 4-methylthiophenol | 6.8 | Sparingly soluble |
| 4-mercaptophenol | 6.8 | Soluble |
| 4-aminothiophenol | 8.86 | Very soluble |
| MESNA | 9.08 | Very soluble |
| Benzyl mercaptan | 9.67 | Sparingly soluble |

For kinetically-controlled convergent ligations, a pre-formed thioester peptide is desirable to maximize the kinetic differences between potential ligation sites. Preforming the phenyl thioester using thiophenol is not straightforward because of its low water solubility. However, a water-soluble thiol such as 4-mercaptophenylacetic acid should be superior to thiophenol in pre-forming phenyl thioesters. To test this, 1 ml of a 250 mM 4-mercaptophenylacetic acid solution in ligation buffer (6 M GdmCl, 200 mM phosphate), pH 7.0, was added to 5.3 mg of LYRAL-COSR-L (SEQ ID NO:6) (final concentration of 6.3 mM peptide). Exchange was monitored by removing aliquots, quenching with acid, and analyzing by RP-HPLC. Results are shown in FIG. 16. Exchange was nearly complete within 1 hour in a small volume of highly concentrated peptide.

Therefore, water-soluble phenyl thiols that have a pKa near 7.0, such as 4-mercaptophenylacetic acid, can be used to increase the rate of NCL by increasing the rate of thiol-thioester exchange with peptide-alkyl thioesters. Preformation of peptide-phenyl thioesters is also more straightforward with such water-soluble thiols compared to thiophenol. Therefore, water-soluble thiols such as 4-mercaptophenylacetic acid should be useful in both sequential and convergent ligations.

Example 5

Selective Desulfurization

The peptide LYRACys(Acm)FGCKI (SEQ ID NO: 13) (FIG. 18) was synthesized using Boc chemistry and was subjected to reduction using freshly prepared Raney nickel in aqueous 6M guanidine hydrochloride, pH 4, room temperature, 20 mM TCEP. Cys was converted to Ala quantitatively in less than 2 hours as determined by LCMS. Only trace amounts of desulfurization of Cys(Acm) were observed.

The synthesis of the 37 amino acid peptide hormone [A24P, S27P, S28P]amylin (SEQ ID NO:14) was also explored. Amylin has a C-terminal carboxyamide and has one disulfide bond between residues 2 and 7. The synthetic strategy for the total chemical synthesis of this target peptide is shown in FIG. 19.

Figure 20:
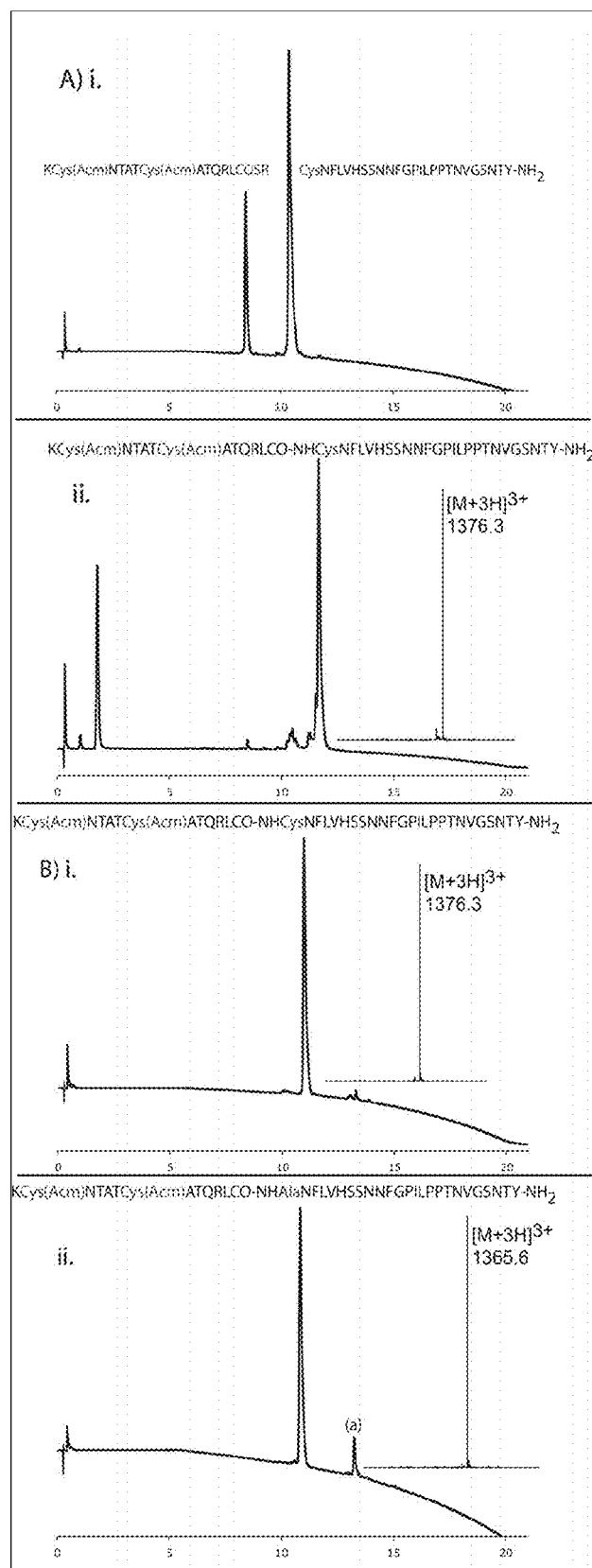

FIG. 20 shows the data for the synthesis of the [A24P, S27P, S28P]amylin polypeptide (SEQ ID NO:14). Native chemical ligation of the two peptides Amylin[1-12] $^\alpha$thioester (SEQ ID NO:16) and Amylin[C13A-37] (SEQ ID NO:17) gave the full-length polypeptide (SEQ ID NO: 15) in near quantitative yield. The purified ligation product (SEQ ID NO:15), that contained a single Cys residue in the presence of two Cys (Acm) residues, was subjected to Raney nickel reduction. After 6 hours, the reduction was complete and the product appeared as a single symmetrical peak with a mass decrease of 32.1 Da. Solid phase extraction (SPE) was used to isolate the desulfurized product, eluting with 0.1% TFA 50/50 acetonitrile/water. The Cys(Acm) protecting groups were removed and the disulfide bond formed by oxidation with iodine (see SI), giving a high yield of [A24P, S27P, S28P]Amylin (SEQ ID NO:14).

The total chemical synthesis of the protein EETI-II using native chemical ligation and selective desulfurization was also explored.

Figure 22:
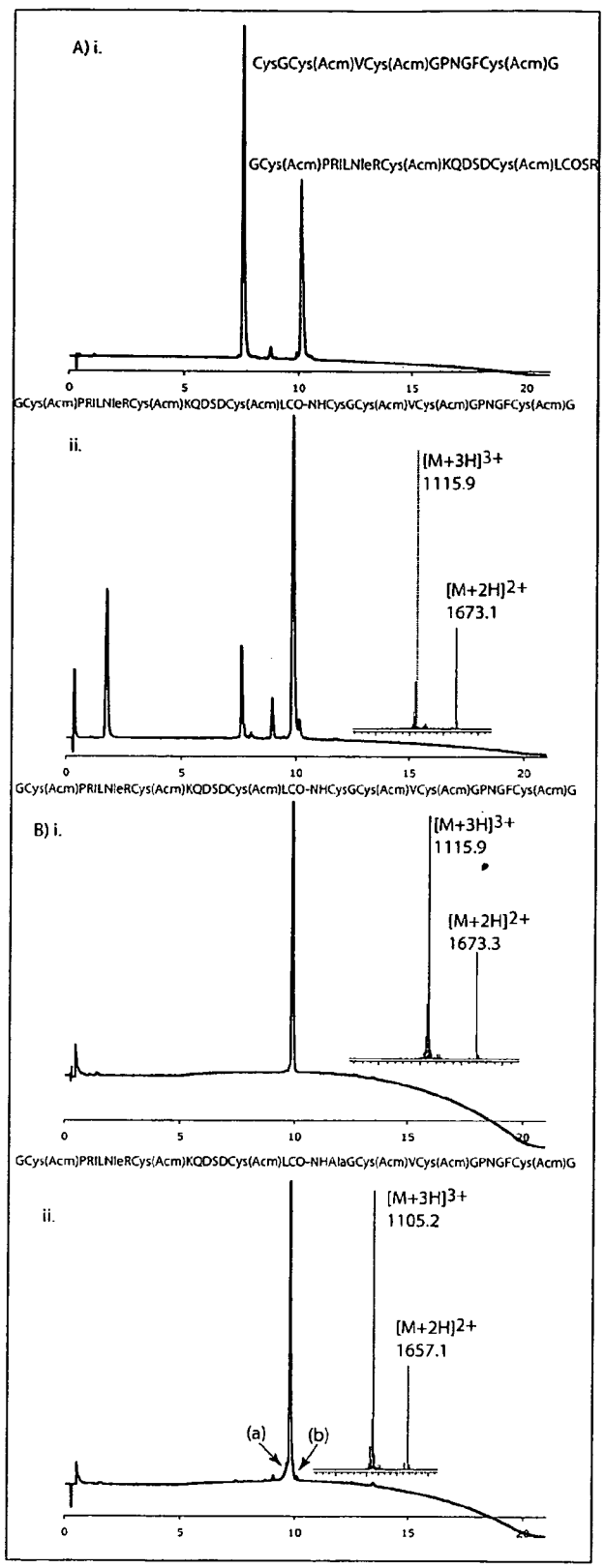

EETI-II is a small trypsin inhibitor that contains three disulfide bonds. This system is an excellent model to demonstrate the exquisite selectivity of the desulfurization reactions presented in this invention. The synthetic route for EETI-II [1-28] (SEQ ID NO:18) involves the selective desulfurization of one Cys residue in the presence of six Cys(Acm) residues, after the ligation of EETI-II[1-16]-$^\alpha$thioester and EETI-II [A17C-28] (see FIG. 21). Subsequently, the Acm protecting groups were removed and the product folded to form three disulfide bonds. The analytical data for the synthesis of the EETI-II polypeptide chain (SEQ ID NO:18) by native chemical ligation followed by selective desulfurization is shown in FIG. 22. The ligation between EETI-II[1-16]-$^\alpha$thioester (SEQ ID NO:19) and EETI-II[A17C-28] (SEQ ID NO:20) took approximately 8 hours and after purification resulted in a 58% isolated yield. The ligation product was then desulfurized and isolated in 89% yield. After the selective desulfurization, the Acm protecting groups were removed with iodine using the same procedure as above, and the kinetically-formed disulfides were reduced with DTT and the protein folded with formation of native disulfides using a glucathione redox couple. The folding reaction was monitored with LCMS and the mass decreased by six Daltons and eluted earlier on RP-HPLC.

In a related study, the selective reduction of Cys in the presence of Met was explored. It was found that Cys can be quantitatively reduced to Ala in the presence of Met and Cys(Acm) using the mild conditions reported above. This finding was demonstrated using a small model peptide EETI-II[1-30] polypeptide (SEQ ID NO:23) that contained both Met and Cys(Acm).

In a related study, suggesting that it is possible to selectively desulfurize an internal cysteinyl residue in the presence of a thioester, a peptide with a C-terminal thioester-based leaving group and with Acm protected cysteinyl residues was added to Raney nickel under selective desulfurization conditions. The peptide was monitored over time and found to be stable; neither the Acm protected cysteinyl residues, nor the C-terminal thioester-based leaving group was desulfurized or chemically modified. The peptide used was a mercaptopropionic Leu thioester and the sequence was KTYQCys(Acm) QYCys(Acm)EYRSCO-SCH2CH2CO-LeuCOOH (SEQ ID NO:26). Approximately 3 mg of peptide was added to the reduction conditions that we already reported in the drafted manuscript that we provided and was done at room temperature. The reaction was monitored for 4 hours.

Peptide Segment Synthesis (peptide-$^\alpha$carboxylate or peptide-$^\alpha$thioester): Peptides were prepared manually by "in situ neutralization" Boc chemistry stepwise solid phase peptide synthesis as discussed in Schnolzer et al. (1992) which is hereby incorporated by reference. Peptides were also prepared on —OCH$_2$-Pam-resins (free $^\alpha$carboxyl peptides) or on HSCH$_2$CH$_2$COLeu-OCH$_2$-Pam-resin ($^\alpha$thioester peptides) as discussed in Hackeng et al. (1999), which is hereby incorporated by reference. Peptides were also prepared on MBHA resin. Side-chain protection for amino acids was as follows: Arg(Tos), Asn(Xan), Asp(OcHex), Cys(4-CH$_3$Bzl), Cys (Acm), His(Bom), Glu(OcHex), Lys(2-Cl—Z), Ser(Bzl), Thr (Bzl), Tyr(Br—Z). (Tos=tosyl, Xan=xanthyl, OcHex=cyclohexyl, 4-CH$_3$Bzl=4-methylbenzyl, Bom=benzyloxymethyl, 2-Cl—Z=2-chlorobenzyloxycarbonyl, Bzl=benzyl, Br—Z=Bromobenzyloxycarbonyl.) After completing chain assembly peptides were deprotected and cleaved from the resin support by treatment with anhydrous HF containing p-cresol (90:10, vol/vol) for 1 h at 0° C. After evaporation of the HF under reduced pressure, crude products were precipitated and triturated with chilled diethyl ether, and the peptide products were dissolved in 50% aqueous acetonitrile containing 0.1% TFA. Peptide compositions were confirmed by LC-MS.

Preparative HPLC: Peptides were purified on C4, C8, or C18 silica with columns of dimension 22×250 mm, 10×250 mm, or 10×100 mm. The silica used was TP Vydac or self-packed Varian Microsorb.

Native Chemical Ligation: Ligation reactions were carried out under standard conditions, as discussed in Dawson et al., (1997), which is hereby incorporated by reference. The reactions were carried out in 200 mM sodium phosphate buffer containing 6 M guanidine hydrochloride, 20 mM TCEP, pH=6.8, 2-4 mM for each peptide, 0.5% (v/v) thiolphenol, purged and sealed.

Selective Desulfurization: Raney nickel was prepared by the slow addition of 100 mg of NaBH$_4$ to 600 mg of Ni(OAc)$_2$ dissolved in 3 mL of deionized water while stirring. After 5 minutes, the reaction was filtered with a medium sintered glass frit and washed with 200 mL of 18 megOhm water. Wet Raney nickel was added to 2-4 mg of peptide dissolved in 3 mL of 200 mM sodium phosphate buffer containing 6 M guanidine hydrochloride and 30 mg of TCEP. The final pH ranged from 3-4 and was not adjusted. Each reaction was monitored by analytical LC and worked up once the starting material was consumed. The identity of the product was verified by LCMS. The product was isolated by spinning down the Raney nickel and recovering the supernatant. The pellet was washed three times with 200 mM sodium phosphate buffer containing 6 M guanidine hydrochloride to insure maximum yields.

EETI-II Folding: Reduced [Met7Nle]EETI-II(1-28) (SEQ ID NO:18).

was dissolved in 50 mM TRIS buffer containing 6 M guanidine hydrochloride at pH 7.8 The solution was diluted over 5 minutes with 20 mM TRIS buffer, 10 mM oxidized glutathione, 2 mM reduced glutathione, until a final concentration of 0.7 mg/mL of protein was reached. The folding was followed by LCMS and the mass changed by 6 Da. The folding is further discussed in Johnson et al. (2006), which is hereby incorporated by reference.

Selective Desulfurization of Cys in the Presence of Met: LACAPMLF (SEQ ID NO:21) was used as a crude peptide and converted into LAAAPMLF (SEQ ID NO:22). Standard desulfurization conditions were used as described above; the reaction was complete in less than 3 hours.

Preparative HPLC: Peptides were purified on C4, C8, or C18 silica with columns of dimension 22'250 mm, 10×250 mm, or a 10×100 mm. The columns used were either Vydac or self-packed using in-house protocols.

Desulfurization of EETI-II (1-30): EETI-II (1-30) (SEQ ID NO:23) was prepared from the ligation of EETI-II (1-16)-(SEQ ID NO:24)$^{\alpha}$thioester-Leu-Leu-Leu-Pro-COOH (SEQ ID NO:25) and Cys$^{17}$-30 (SEQ ID NO:33). The ligation product was purified by RP-HPLC. Chromatogram i) is T=0 for the selective desulfurization reaction of Cys$^{17}$ to native Ala$^{17}$ in the presence of both Met and Cys(Acm). The desulfurization was complete after 3 hours as verified by a mass change of 3 1.3 Da.

REFERENCES

The following references, to the extent that they provide exemplary procedural or other details supplementary to those set forth herein, are specifically incorporated herein by reference.

U.S. Pat. No. 4,668,476
U.S. Pat. N. 4,816,513
U.S. Pat. No. 5,186,898
U.S. Pat. No. 5,854,389
U.S. Pat. No. 6,307,018
U.S. Pat. No. 6,476,190
U.S. Pat. No. 6,642,357
U.S. Pat. No. 6,184,344
U.S. Pat. No. 6,326,468
U.S. Pub. 2005/0113563
Aguilar, In: *Hplc of Peptides and Proteins: Methods and Protocols*, Methods in Molecular Biology, Humana Press, 2004.
Bang and Kent, *Angew. Chem., Int. Ed.*, 43:2534, 2004.
Bang and Kent, *Proc. Natl. Acad. Sci. USA*, 102:5014, 2005.
Bang et al., *J. Am. Chem. Soc.*, 126:1377, 2004.
Bang et al., *Organic Ltrs.*, 8(6):1049-1052, 2006.
Bange et al., *Nat. Med.*, 7(5):548-552, 2001.
Bode et al., *Angewandte Chemie-Intl. Ed.*, 45(8):1248-1252, 2006.
Bycroft et al., *J. Chem. Soc. Chem. Comm.*, 776-777, 1993.
Canne et al., *J. Am. Chem. Soc.*, 117:2998, 1995.
Canne et al., *J. Am. Chem. Soc.*, 118:5891, 1996.
Canne et al., *J. Am. Chem. Soc.*, 121:8720, 1999.
Casi and Hilvert, *Curr. Opin. Struc. Biol.*, 13:589, 2003.
Cutler, *Proteomic*, 3(1):3-18, 2003
Davis, *Chem. Rev.*, 102:579, 2002.
Dawson and Kent, *Annu. Rev. Biochem.*, 69:923, 2000.
Dawson et al., *J. Am. Chem. Soc.*, 119:4325, 1997.
Dawson et al., *J. Am. Chem. Soc.*, 119:4325-4329, 1997.
Dawson et al., *Science*, 266:776, 1994.
Evans et al., *J. Biol. Chem.*, 274:18359, 1999.
Gentle et al., *Bioconjugate Chem.*, 15:658, 2004.
Green and Wuts, In: *Protective Groups in Organic Synthesis*, 2d Ed., 293-294, 318-319, 1991.
Hackeng et al., *Proc. Natl. Acad. Sci. USA*, 96:10068-10073, 1999.
Jelsch et al., *Proc. Natl. Acad. Sci. USA*, 97:3171, 2000.
Jencks, In: *Catalysis in Chemistry and Enzymology*, Dover Publications, Inc., 537-542, 1987.
Johnson and Kent, *J. Amer. Chem. Soc.*, 128:6640-6646, 2006.
Johnson et al., *Angewandte Chemie-Intl. Ed.*, 45:3283-3287, 2006a.
Kochendoerfer et al., *Science*, 299:884, 2003.
Low et al., *Proc. Natl. Acad. Sci. USA*, 98:6554, 2001.
Merrifield, *J. Org. Chem.*, 43:4808-4816, 1978.
Miller, *J. Am. Chem. Soc.*, 119:2301-2302, 1997.
Muir, *Ann. Rev. Biochem.*, 72:249, 2003.
Nilsson et al., *Annu. Rev. Biophys. Biomol. Struc.*, 34:91, 2005.
Royo et al., *Tetrahedron Lett.*, 33:2391-2394, 1992.
Samukov et al., *Tetrahedron Lett.*, 35:7821-7824, 1994.
Schnolzer and Kent, *Science*, 256:221, 1992.
Schnolzer et al., *Int. J. Peptide Protein Res.*, 40: 180-193, 1992.
Teeter et al., *Biochemistry*, 20:5437, 1981.
Villain, *Proc. Second Int. Seventeenth Am. Peptide Symp.*, 107, 2001.
Voet, In: *Biochemisty*, John Wiley, 2nd ed., 58-59, 1995.
Warren et al., *J. Am. Chem. Soc.*, 126:6576-6578, 2004.
Yan and Dawson, *J. Am. Chem. Soc.*, 123:526, 2001.
Zhang and Tam, *J. Am. Chem. Soc.*, 119:2363, 1997.

What is claimed is:

1. A method of synthesizing a polypeptide comprising:
obtaining
- a first C-activated peptide, having (1) an N-terminal-protected cysteinyl residue or an N-terminal non-cysteinyl residue and (2) a good C-terminal thiol-based leaving group;
- a first N-deprotected peptide, having an N-terminal unprotected cysteinyl residue and a weak C-terminal thiol-based leaving group;
- a second C-activated peptide, having an N-terminal-protected cysteinyl residue and a good C-terminal thiol-based leaving group, wherein the good C-terminal thiol-based leaving groups are the same or different;
- a second N-deprotected peptide, having (1) an N-terminal unprotected cysteinyl residue and (2) a C-terminal α-carboxylate, α-carboxamide, or a weak C-terminal thiol-based leaving group, wherein the weak C-terminal thiol-based leaving groups are the same or different;

combining the first C-activated peptide with the first N-deprotected peptide to form a first ligation product having an amide bond between the α-carbon of the C-terminal residue of the first C-activated peptide and the α-carbon of the N-terminal of the first N-deprotected peptide;

combining the second C-activated peptide with the second N-deprotected peptide to form a second ligation product having an amide bond between the α-carbon of the C-terminal residue of the second C-activated peptide and the α-carbon of the N-terminal of the second N-deprotected peptide;

replacing the weak C-terminal thiol-based leaving group of the first ligation product or the second ligation product with a good C-terminal thiol-based leaving group to form a C-activated ligation product, and deprotecting the N-terminal-protected cysteinyl residue of the first ligation product or the second ligation product to form a N-deprotected ligation product;

combining the C-activated ligation product with the N-deprotected ligation product to form a third ligation product having an amide bond between the α-carbon of the C-terminal residue of the C-activated ligation product and the α-carbon of the N-terminal of the N-deprotected ligation product;

whereby the third ligation product is a polypeptide.

2. The method of claim 1 wherein one or more of the first C-activated peptide, the first N-deprotected peptide, the second C-activated peptide, the second N-deprotected peptide, the first ligation product, the second ligation product, the N-deprotected ligation product, the C-activated ligation product, the third ligation product, or the polypeptide each independently contain one or more internal residues with protected side chains.

3. The method of claim 2, wherein the internal residues with protected side chains are protected cysteinyl residues.

4. The method of claim 3, wherein the protected cysteinyl residues are protected with a protection group selected from the group consisting of acetamidomethyl (Acm), trimethylacetamidomethyl (Tacm), and phenylacetamidomethyl (Phacm).

5. The method of claim 4, wherein the protection group is Acm.

6. The method of claim 2, wherein one or more of the first C-activated peptide, the first N-deprotected peptide, the second C-activated peptide, the second N-deprotected peptide, the first ligation product, the second ligation product, the N-deprotected ligation product, the C-activated ligation product, the third ligation product, or the polypeptide is selectively desulfurized to convert cysteinyl residues into alanyl residues, whereby neither the internal residues with protected side chains nor the thiol-based leaving groups are desulfurized.

7. The method of claim 2, further comprising deprotecting the protected side chains from one or more one or more of the first C-activated peptide, the first N-deprotected peptide, the second C-activated peptide, the second N-deprotected peptide, the first ligation product, the second ligation product, the N-deprotected ligation product, the C-activated ligation product, the third ligation product, or the polypeptide.

8. The method of claim 1, wherein any of the good C-terminal thiol-based leaving groups is —$SR_1$, wherein $R_1$ is a substituted or unsubstituted $C_6$-$C_{15}$-aryl.

9. The method of claim 8, wherein $R_1$ is chosen from the group consisting of —$C_6H_4COOH$, —$C_6H_4COO^-$, —$C_6H_4Cl$, —$C_6H_4NO_2$, —$C_6H_4CH_3$, —$C_6H_4OH$, —$C_6H_4OCOCH_3$, —$C_6H_4COOCH_3$, —$C_6H_4CH_2COOH$, —$C_6H_4CH_2COO^-$, —$C_6H_4CONH_2$, and —$C_6H_4CH_2CONH_2$.

10. The method of claim 9, wherein at least one of the good C-terminal thiol-based leaving groups is $C_6H_4CH_2COOH$ or —$C_6H_4CH_2COO$.

11. The method of claim 1, wherein the weak C-terminal thiol-based leaving group is —SH, —$S^-$ or —$SR_2$, wherein $R_2$ represents a substituted or unsubstituted version of $C_1$-$C_{15}$-alkyl or $C_1$-$C_{15}$-aralkyl.

12. The method of claim 11, wherein $R_2$ is —$CH_2CH_2SO_3Na$, —$CH_2SO_3Na$, —$CH_2CH_2CONHCH(R_3)COOH$, —$CH_2CONHCH(R_3)COOH$, —$CH_2CH_2CONHCH(R_3)COO^-$, —$CH_2CONHCH(R_3)COO^-$, —$CH_2CH_2CONHCH(R_3)CONH_2$, —$CH_2CONHCH(R_3)CONH_2$, —$CH_2CH_2CO(Arg)_nOH$, or —$CH_2CH_2CO(Arg)_nNH_2$; wherein $R_3$ is H, amino, hydroxyl, halo, —$NHR_4$, —$NR_4R_5$, —$OR_4$, or a substituted or unsubstituted version of $C_1$-$C_{10}$-alkyl, $C_2$-$C_{10}$-alkenyl, $C_2$-$C_{10}$-alkynyl, $C_6$-$C_{10}$-aryl, $C_7$-$C_{10}$-aralkyl, $C_{10}$-heteroaryl, $C_2$-$C_{10}$-heteroaralkyl, or $C_1$-$C_{10}$-acyl; wherein $R_4$ and $R_5$ are each independently H or a substituted or unsubstituted version of $C_1$-$C_{10}$-alkyl, $C_2$-$C_{10}$-alkenyl, $C_2$-$C_{10}$-alkynyl, $C_6$-$C_{10}$-aryl, $C_7$-$C_{10}$-aralkyl, $C_1$-$C_{10}$-heteroaryl, $C_2$-$C_{10}$-heteroaralkyl, or $C_1$-$C_{10}$-acyl; further wherein Arg is an arginyl residue, n is an integer from 1 to 6 and $(Arg)_{4-6}$ is SEQ ID NO:34, SEQ ID NO:35, or SEQ ID NO:36, respectively.

13. The method of claim 1, wherein the N-terminal protected cysteinyl residue has a linking group connecting its thiol group to its amino group.

14. The method of claim 13, wherein the linking group is —$CH_2$—, —$CH(R_6)$—, or —$C(R_6)(R_7)$—, wherein $R_6$ and $R_7$ are each independently, amino, hydroxyl, halo, —$NHR_8$, —$NR_8R_9$, —$OR_8$, or a substituted or unsubstituted version of $C_1$-$C_{10}$-alkyl, $C_2$-$C_{10}$-alkenyl, $C_2$-$C_{10}$-alkynyl, $C_6$-$C_{10}$-aryl, $C_7$-$C_{10}$-aralkyl, $C_1$-$C_{10}$-heteroaryl, $C_2$-$C_{10}$-heteroaralkyl, or $C_1$-$C_{10}$-acyl; wherein $R_8$ and $R_9$ are each independently H or a substituted or unsubstituted version of $C_1$-$C_{10}$-alkyl, $C_2$-$C_{10}$-alkenyl, $C_2$-$C_{10}$-alkynyl, $C_6$-$C_{10}$-aryl, $C_7$-$C_{10}$-aralkyl, $C_1$-$C_{10}$-heteroaryl, $C_2$-$C_{10}$-heteroaralkyl, or $C_1$-$C_{10}$-acyl.

15. The method of claim 1, further comprising obtaining a third C-activated peptide having an N-terminal-protected cysteinyl residue and a good C-terminal thiol-based leaving group;

deprotecting the N-terminal-protected cysteinyl residue of the third ligation product to form a further N-deprotected ligation product, and combining the third C-activated peptide with the further N-deprotected ligation product to form a fourth ligation product having an amide bond between the α-carbon of the C-terminal residue of the third C-activated peptide and the α-carbon of the N-terminal of the further N-deprotected ligation product;

whereby the fourth ligation product is a polypeptide.

16. The method of claim 1, further comprising obtaining a third N-deprotected peptide having an N-terminal unprotected cysteinyl residue and one of the weak C-terminal thiol-based leaving groups;

replacing the weak C-terminal thiol-based leaving group of the third ligation product with a good C-terminal thiol-based leaving group to form a further C-activated ligation product, and combining the further C-activated ligation product with the third N-deprotected peptide to form a fifth ligation product having an amide bond between the α-carbon of the C-terminal residue of the further C-activated ligation product and the α-carbon of the N-terminal of the third N-deprotected peptide;

whereby the fifth ligation product is a polypeptide.

17. The method of claim 1, wherein one or both of the first C-activated peptide and the second C-activated peptide is a C-activated ligation product, formed prior to its use in the method of claim 1.

18. The method of claim 1, wherein one or both of the first N-deprotected peptide and the second N-deprotected peptide is a N-deprotected ligation product, formed prior to its use in the method of claim 1.

19. The method of claim 1, wherein one or more of
the combining of the first C-activated peptide with the first N-deprotected peptide to form a first ligation product,
the combining of the second C-activated peptide with the second N-deprotected peptide to form a second ligation product, or
the combining of the C-activated ligation product with the first N-deprotected peptide to form a third ligation product, occurs in an aqueous buffer having a pH between 6 and 8.

20. The method of claim 1, further comprising deprotecting one or more of the N-terminal protected cysteinyl residue of the first ligation product, the second ligation product, or the third ligation product with methoxyamine-hydrochloride, carboxymethoxylamine-hemihydrochloride, o-phenylhydroxylamine-hydrochloride, o-benzylhydroxylamine-hydrochloride, o-4-nitrobenzylhydroxylamine-hydrochloride, and hydroxylamine-hydrochloride.

21. The method of claim 20, wherein deprotecting with methoxyamine-hydrochloride occurs in aqueous buffer at a pH from 3 to 5.

22. A method for synthesizing a polypeptide comprising:
a) reacting a first N—$C^a$ peptide with a first $N^a$—C peptide to form a first N—C ligation product;
b) reacting a second N—$C^a$ peptide with a second $N^a$—C peptide to form a second N—C ligation product;
c) converting the first N—C ligation product, into a N—$C^a$ ligation product;
d) converting the second N—C ligation product, into a $N^a$—C ligation product, and
e) reacting the N—$C^a$ ligation product with the $N^a$—C ligation product to form a third N—C ligation product, whereby the third N—C ligation product is a polypeptide;
wherein:
neither the first N—$C^a$ peptide, first $N^a$—C peptide, second N—$C^a$ peptide, nor the second $N^a$—C peptide contain any internal residues with protected side chains;
N and $N^a$ represent the N-terminal residue;
C and $C^a$ represent the C-terminal residue;
$C^a$ is more reactive than C, and
$N^a$ is more reactive than N,
further wherein one or more of steps a, b and e occurs in the presence of 4-mercaptophenyl acetic acid.

23. A method of synthesizing a polypeptide comprising:
obtaining
a first C-activated peptide, having an N-terminal-protected cysteinyl residue and a good C-terminal thioester-based leaving group;
a first N-deprotected peptide, having an N-terminal unprotected cysteinyl residue and a weak C-terminal thioester-based leaving group;
a second C-activated peptide, having (1) an N-terminal-protected cysteinyl residue or an N-terminal non-cysteinyl residue and (2) a good C-terminal thioester-based leaving group, wherein the good C-terminal thioester-based leaving groups are the same or different;
combining the first C-activated peptide with the first N-deprotected peptide to form a first ligation product having an amide bond between the α-carbon of the C-terminal residue of the first C-activated peptide and the α-carbon of the N-terminal of the first N-deprotected peptide;
deprotecting the N-terminal-protected cysteinyl residue of the first ligation product to form an N-deprotected ligation product, and
combining the second C-activated peptide with the N-deprotected ligation product to form a second ligation product having an amide bond between the α-carbon of the C-terminal residue of the second C-activated peptide and the α-carbon of the N-terminal of the N-deprotected ligation product;
wherein the side chains of the internal residues of the first C-activated peptide, the first N-deprotected peptide, and the second C-activated peptide are unprotected, and
whereby the second ligation product is a polypeptide.

24. A method of synthesizing a polypeptide comprising:
obtaining
a first C-activated peptide, having (1) an N-terminal-protected cysteinyl residue or an N-terminal non-cysteinyl residue and (2) a good C-terminal thioester-based leaving group;
a first N-deprotected peptide, having an N-terminal unprotected cysteinyl residue and a weak C-terminal thioester-based leaving group;
a second N-deprotected peptide, having an N-terminal unprotected cysteinyl residue and a weak C-terminal thioester-based leaving group, wherein the weak C-terminal thioester-based leaving groups are the same or different;
combining the first C-activated peptide with the first N-deprotected peptide to form a first ligation product having an amide bond between the α-carbon of the C-terminal residue of the first C-activated peptide and the α-carbon of the N-terminal of the first N-deprotected peptide;
replacing the weak C-terminal thioester-based leaving group of the first ligation product with a good C-terminal thioester-based leaving group to form a C-activated ligation product, and
combining the second N-deprotected peptide with the C-activated ligation product to form a second ligation product having an amide bond between the α-carbon of the C-terminal residue of the C-activated ligation product and the α-carbon of the N-terminal of the second N-deprotected peptide;
wherein the side chains of the internal residues of the first C-activated peptide, the first N-deprotected peptide, and the second N-deprotected peptide are unprotected, and
whereby the second ligation product is a polypeptide.

25. A method of selectively desulfurizing a polypeptide, comprising: obtaining a polypeptide containing both cysteinyl residues with protected side chains and cysteinyl residues with unprotected side chains, and reacting said polypeptide with a desulfurizing agent to convert the cysteinyl residues with unprotected side chains into alanyl residues, whereby the cysteinyl residues with protected side chains are not desulfurized, and wherein the protected side chains are protected with a protection group selected from the group consisting of Acm, Tacm, and Phacm.

* * * * *

UNITED STATES PATENT AND TRADEMARK OFFICE
CERTIFICATE OF CORRECTION

PATENT NO. : 7,674,881 B2  Page 1 of 1
APPLICATION NO. : 11/545923
DATED : March 9, 2010
INVENTOR(S) : Stephen B. H. Kent et al.

It is certified that error appears in the above-identified patent and that said Letters Patent is hereby corrected as shown below:

In claim 10, column 81, line 59, delete "$C_6H_4CH_2COOH$" and insert -- —$C_6H_4CH_2COOH$ -- therefor.

In claim 10, column 81, line 60, delete "—$C_6H_4CH_2COO$" and insert -- —$C_6H_4CH_2COO^-$ -- therefor.

In claim 12, column 82, lines 7-8, delete "$C_{10}$-heteroaryl" and insert -- $C_1$-$C_{10}$-heteroaryl -- therefor.

Signed and Sealed this

Eighteenth Day of May, 2010

David J. Kappos
*Director of the United States Patent and Trademark Office*